US011357471B2

(12) United States Patent
Sabatino

(10) Patent No.: US 11,357,471 B2
(45) Date of Patent: Jun. 14, 2022

(54) ACQUIRING AND PROCESSING ACOUSTIC ENERGY EMITTED BY AT LEAST ONE ORGAN IN A BIOLOGICAL SYSTEM

(71) Applicant: Michael E. Sabatino, Broken Arrow, OK (US)

(72) Inventor: Michael E. Sabatino, Broken Arrow, OK (US)

(*) Notice: Subject to any disclaimer, the term of this patent is extended or adjusted under 35 U.S.C. 154(b) by 907 days.

(21) Appl. No.: 14/524,810

(22) Filed: Oct. 27, 2014

(65) Prior Publication Data

US 2015/0105695 A1 Apr. 16, 2015
US 2020/0015773 A9 Jan. 16, 2020

Related U.S. Application Data

(63) Continuation of application No. 13/430,561, filed on Mar. 26, 2012, now Pat. No. 8,870,791, which is a continuation of application No. 11/602,017, filed on Nov. 20, 2006, now Pat. No. 8,920,343.

(60) Provisional application No. 60/785,357, filed on Mar. 23, 2006.

(51) Int. Cl.
*A61B 5/00* (2006.01)
*A61B 7/04* (2006.01)
*A61B 7/00* (2006.01)

(52) U.S. Cl.
CPC ............. *A61B 7/04* (2013.01); *A61B 5/0022* (2013.01); *A61B 5/7257* (2013.01); *A61B 5/742* (2013.01); *A61B 7/00* (2013.01)

(58) Field of Classification Search
CPC . A61B 2562/0204; A61B 5/0002; A61B 7/04; A61B 5/0022; A61B 5/7257; A61B 5/742; A61B 7/00

USPC ............... 600/300, 559, 301, 529; 340/521
See application file for complete search history.

(56) References Cited

U.S. PATENT DOCUMENTS 3,990,435 A * 11/1976 Murphy ............... A61B 5/0803
600/529
4,207,622 A * 6/1980 Miller .................. G01S 3/8083
367/126
4,267,845 A 5/1981 Robertson, Jr. et al.
4,344,436 A 8/1982 Kubota
(Continued)

FOREIGN PATENT DOCUMENTS

AU 2005100352 6/2005
CA 2245788 8/1998
(Continued)

OTHER PUBLICATIONS

TX Handheld User Guide, Palm Inc., 2005, pp. 1-148, 263-305, 421-471.
(Continued)

*Primary Examiner* — May A Abouelela
(74) *Attorney, Agent, or Firm* — Hall Estill Law Firm

(57) ABSTRACT

In some embodiments, an apparatus for acquiring, processing and transmitting physiological sounds, which may include acoustic sounds from at least one organ in a biological system, may include a sensor for acquiring physiological sounds. Analogue signals representative of the physiological sounds are converted into an electrical output. The electrical output is converted to digital data. A processing unit processes the digital data in a manner selected by a user.

20 Claims, 30 Drawing Sheets

(56) References Cited

U.S. PATENT DOCUMENTS

| | | |
|---|---|---|
| 4,528,689 A * | 7/1985 | Katz .................. G01H 3/00 360/32 |
| 4,889,132 A * | 12/1989 | Hutcheson ......... A61B 5/02208 600/493 |
| 4,991,581 A | 2/1991 | Andries |
| 5,007,429 A | 4/1991 | Treatch et al. |
| 5,010,889 A | 4/1991 | Bredesen et al. |
| 5,012,815 A | 5/1991 | Bennett |
| 5,099,204 A | 3/1992 | Wheatley |
| 5,103,459 A | 4/1992 | Gilhousen et al. |
| 5,107,225 A | 4/1992 | Wheatley et al. |
| 5,155,805 A | 10/1992 | Kaasila |
| 5,159,668 A | 10/1992 | Kaasila |
| 5,187,480 A | 2/1993 | Thomas et al. |
| 5,193,094 A | 3/1993 | Viterbi |
| 5,218,969 A | 6/1993 | Bredesen et al. |
| 5,257,283 A | 10/1993 | Gilhousen et al. |
| 5,265,119 A | 11/1993 | Gilhousen et al. |
| 5,276,765 A | 1/1994 | Freeman et al. |
| 5,280,472 A | 1/1994 | Gilhousen et al. |
| 5,283,536 A | 2/1994 | Wheatley |
| 5,289,527 A | 2/1994 | Tiedemann |
| 5,307,405 A | 4/1994 | Sih |
| 5,309,474 A | 5/1994 | Gilhousen et al. |
| 5,325,479 A | 6/1994 | Kaasila |
| 5,339,046 A | 8/1994 | Kornfeld et al. |
| 5,341,456 A | 8/1994 | DeJaco |
| 5,383,219 A | 1/1995 | Wheatley et al. |
| 5,392,287 A | 2/1995 | Tiedemann et al. |
| 5,396,516 A | 3/1995 | Padovani et al. |
| 5,408,697 A | 4/1995 | Price et al. |
| 5,414,728 A | 5/1995 | Zehavi |
| 5,426,392 A | 6/1995 | Kornfeld |
| 5,437,055 A | 7/1995 | Wheatley et al. |
| 5,441,047 A | 8/1995 | David et al. |
| 5,442,322 A | 8/1995 | Kornfeld et al. |
| 5,442,627 A | 8/1995 | Viterbi et al. |
| 5,452,473 A | 9/1995 | Weiland et al. |
| 5,461,639 A | 10/1995 | Wheatley et al. |
| 5,469,115 A | 11/1995 | Peterzell et al. |
| 5,469,471 A | 11/1995 | Wheatley |
| 5,471,497 A | 11/1995 | Zehavi |
| 5,475,870 A | 12/1995 | Weaver et al. |
| 5,479,475 A | 12/1995 | Grob et al. |
| 5,483,696 A | 1/1996 | Wheatley et al. |
| 5,485,486 A | 1/1996 | Gilhousen et al. |
| 5,487,175 A | 1/1996 | Bayley et al. |
| 5,497,395 A | 3/1996 | Jou |
| 5,499,280 A | 3/1996 | Wilson et al. |
| 5,509,015 A | 4/1996 | Tiedemann et al. |
| 5,509,035 A | 4/1996 | Teidemann et al. |
| 5,511,067 A | 4/1996 | Miller |
| 5,513,176 A | 4/1996 | Dean et al. |
| 5,515,177 A | 5/1996 | Propach et al. |
| 5,517,323 A | 5/1996 | Propach et al. |
| 5,519,761 A | 5/1996 | Gilhousen |
| 5,528,593 A | 6/1996 | English et al. |
| 5,530,928 A | 6/1996 | Wheatley et al. |
| 5,533,011 A | 7/1996 | Dean et al. |
| 5,539,531 A | 7/1996 | Propach et al. |
| 5,544,223 A | 8/1996 | Robbins et al. |
| 5,546,459 A | 8/1996 | Sih et al. |
| 5,548,812 A | 8/1996 | Padovani et al. |
| 5,550,902 A | 8/1996 | Abbruscato |
| 5,559,865 A | 9/1996 | Gilhousen |
| 5,559,881 A | 9/1996 | Sih |
| 5,561,618 A | 10/1996 | Dehesh |
| 5,564,083 A | 10/1996 | Lee et al. |
| 5,566,000 A | 10/1996 | Holcman |
| 5,566,206 A | 10/1996 | Butler et al. |
| 5,574,773 A | 11/1996 | Grob et al. |
| 5,574,987 A | 11/1996 | Wallace |
| 5,576,662 A | 11/1996 | Price et al. |
| 5,577,022 A | 11/1996 | Padovani et al. |
| 5,577,265 A | 11/1996 | Wheatley |
| 5,588,043 A | 12/1996 | Tiedemann et al. |
| 5,589,756 A | 12/1996 | Wilson et al. |
| 5,590,069 A | 12/1996 | Levin |
| 5,590,406 A | 12/1996 | Bayley et al. |
| 5,590,408 A | 12/1996 | Weiland et al. |
| 5,592,548 A | 1/1997 | Sih |
| 5,594,718 A | 1/1997 | Weaver et al. |
| 5,596,570 A | 1/1997 | Soliman |
| 5,598,849 A | 2/1997 | Browne |
| 5,602,833 A | 2/1997 | Zehavi |
| 5,602,834 A | 2/1997 | Dean et al. |
| 5,603,096 A | 2/1997 | Gilhousen et al. |
| 5,604,459 A | 2/1997 | White |
| 5,604,730 A | 2/1997 | Tiedemann |
| 5,608,722 A | 3/1997 | Miller |
| 5,614,806 A | 3/1997 | Wilson et al. |
| 5,617,060 A | 4/1997 | Wilson et al. |
| 5,621,752 A | 4/1997 | Antonio et al. |
| 5,621,784 A | 4/1997 | Tiedemann et al. |
| 5,621,853 A | 4/1997 | Gardner |
| 5,625,876 A | 4/1997 | Gilhousen et al. |
| 5,627,857 A | 5/1997 | Wilson |
| 5,629,955 A | 5/1997 | McDonough |
| 5,629,975 A | 5/1997 | Tiedemann et al. |
| 5,638,412 A | 6/1997 | Blakeney et al. |
| 5,640,414 A | 6/1997 | Blakeney et al. |
| 5,642,398 A | 6/1997 | Tiedemann et al. |
| 5,644,591 A | 7/1997 | Sutton |
| 5,644,596 A | 7/1997 | Sih |
| 5,646,991 A | 7/1997 | Sih |
| 5,652,814 A | 7/1997 | Pan et al. |
| 5,654,979 A | 8/1997 | Levin et al. |
| 5,655,220 A | 8/1997 | Weiland et al. |
| 5,663,807 A | 9/1997 | Propach et al. |
| 5,666,122 A | 9/1997 | Carter |
| 5,673,259 A | 9/1997 | Quick |
| 5,675,581 A | 10/1997 | Soliman |
| 5,675,644 A | 10/1997 | Sih |
| 5,677,874 A | 10/1997 | Yamano |
| 5,680,395 A | 10/1997 | Weaver et al. |
| 5,680,567 A | 10/1997 | Dent |
| 5,687,229 A | 11/1997 | Sih |
| 5,689,286 A | 11/1997 | Wugofski |
| 5,689,557 A | 11/1997 | Kaplan |
| 5,691,974 A | 11/1997 | Zehavi et al. |
| 5,692,006 A | 11/1997 | Ross |
| 5,696,468 A | 12/1997 | Nise |
| 5,697,055 A | 12/1997 | Gilhousen et al. |
| 5,701,904 A | 12/1997 | Simmons et al. |
| 5,703,902 A | 12/1997 | Ziv et al. |
| 5,704,001 A | 12/1997 | Gardner |
| 5,708,448 A | 1/1998 | Wallace |
| 5,710,521 A | 1/1998 | Butler |
| 5,710,758 A | 1/1998 | Soliman et al. |
| 5,710,768 A | 1/1998 | Ziv et al. |
| 5,715,236 A | 2/1998 | Gilhousen et al. |
| 5,715,526 A | 2/1998 | Weaver et al. |
| 5,722,044 A | 2/1998 | Padovani et al. |
| 5,722,053 A | 2/1998 | Kornfeld et al. |
| 5,722,061 A | 2/1998 | Hutchison et al. |
| 5,722,063 A | 2/1998 | Peterzell et al. |
| 5,724,385 A | 3/1998 | Levin et al. |
| 5,727,123 A | 3/1998 | McDonough et al. |
| 5,729,540 A | 3/1998 | Wegrzyn |
| 5,732,134 A | 3/1998 | Sih |
| 5,732,341 A | 3/1998 | Wheatley |
| 5,734,716 A | 3/1998 | Kulberg |
| 5,737,687 A | 4/1998 | Martin et al. |
| 5,737,708 A | 4/1998 | Grob et al. |
| 5,742,734 A | 4/1998 | DeJaco et al. |
| 5,748,104 A | 5/1998 | Argyroudis et al. |
| 5,749,067 A | 5/1998 | Barrett |
| 5,751,725 A | 5/1998 | Chen |
| 5,751,761 A | 5/1998 | Gilhousen |
| 5,751,901 A | 5/1998 | DeJaco et al. |
| 5,754,533 A | 5/1998 | Bender et al. |
| 5,754,542 A | 5/1998 | Ault et al. |
| 5,754,733 A | 5/1998 | Gardner et al. |
| 5,757,767 A | 5/1998 | Zehavi |

(56) References Cited

U.S. PATENT DOCUMENTS

| | | | |
|---|---|---|---|
| 5,757,858 A | 5/1998 | Black et al. |
| 5,758,266 A | 5/1998 | Kornfeld et al. |
| 5,761,204 A | 6/1998 | Grob et al. |
| 5,764,687 A | 6/1998 | Easton |
| 5,772,586 A | 6/1998 | Heinonen et al. |
| 5,774,563 A | 6/1998 | DeLauriers |
| 5,777,990 A | 7/1998 | Zehavi et al. |
| 5,778,024 A | 7/1998 | McDonough |
| 5,781,543 A | 7/1998 | Ault et al. |
| 5,781,856 A | 7/1998 | Jacobs et al. |
| 5,781,867 A | 7/1998 | Tidwell |
| 5,784,406 A | 7/1998 | DeJaco et al. |
| 5,784,532 A | 7/1998 | McDonough et al. |
| 5,790,589 A | 8/1998 | Hutchison et al. |
| 5,790,632 A | 8/1998 | Antonio et al. |
| 5,793,338 A | 8/1998 | Standke et al. |
| 5,799,005 A | 8/1998 | Soliman |
| 5,799,254 A | 8/1998 | Karmi et al. |
| 5,802,105 A | 9/1998 | Tiedemann et al. |
| 5,805,648 A | 9/1998 | Sutton |
| 5,805,843 A | 9/1998 | Gehlhaar |
| 5,812,036 A | 9/1998 | Estrada |
| 5,812,094 A | 9/1998 | Maldonado |
| 5,812,097 A | 9/1998 | Maldonado |
| 5,812,538 A | 9/1998 | Wiedeman et al. |
| 5,812,607 A | 9/1998 | Hutchinson et al. |
| 5,812,651 A | 9/1998 | Kaplan |
| 5,812,678 A | 9/1998 | Scalise et al. |
| 5,812,938 A | 9/1998 | Gilhousen et al. |
| 5,818,437 A | 10/1998 | Grover et al. |
| 5,818,871 A | 10/1998 | Blakeney et al. |
| 5,822,318 A | 10/1998 | Tiedemann et al. |
| 5,825,253 A | 10/1998 | Mathe et al. |
| 5,825,895 A * | 10/1998 | Grasfield | A61B 7/04 381/67 |
| 5,827,179 A | 10/1998 | Lichter et al. |
| 5,827,180 A | 10/1998 | Goodman |
| 5,827,195 A | 10/1998 | Lander |
| 5,828,348 A | 10/1998 | Tassoudji et al. |
| 5,828,661 A | 10/1998 | Weaver et al. |
| 5,832,296 A | 11/1998 | Wang et al. |
| 5,835,065 A | 11/1998 | Wallace et al. |
| 5,835,847 A | 11/1998 | Gilmore et al. |
| 5,839,052 A | 11/1998 | Dean et al. |
| 5,841,806 A | 11/1998 | Gilhousen et al. |
| 5,841,846 A | 11/1998 | Abbruscato |
| 5,842,124 A | 11/1998 | Kenagy et al. |
| 5,844,784 A | 12/1998 | Moran et al. |
| 5,844,885 A | 12/1998 | Grob et al. |
| 5,844,899 A | 12/1998 | Daley et al. |
| 5,844,985 A | 12/1998 | Kulberg et al. |
| 5,844,997 A | 12/1998 | Murphy, Jr. |
| 5,848,063 A | 12/1998 | Weaver et al. |
| 5,848,099 A | 12/1998 | Benner |
| 5,850,612 A | 12/1998 | Kulberg et al. |
| 5,852,421 A | 12/1998 | Maldonado |
| 5,854,565 A | 12/1998 | Jha et al. |
| 5,854,786 A | 12/1998 | Henderson et al. |
| 5,857,147 A | 1/1999 | Gardner et al. |
| 5,859,612 A | 1/1999 | Gilhousen |
| 5,859,838 A | 1/1999 | Soliman |
| 5,859,840 A | 1/1999 | Tiedemann et al. |
| 5,859,844 A | 1/1999 | Kanno et al. |
| 5,860,933 A | 1/1999 | Don Michael |
| 5,862,471 A | 1/1999 | Tiedemann et al. |
| 5,862,474 A | 1/1999 | Kimball |
| 5,864,760 A | 1/1999 | Gilhousen et al. |
| 5,864,763 A | 1/1999 | Leung et al. |
| 5,865,759 A | 1/1999 | Koblanski |
| 5,867,527 A | 2/1999 | Ziv et al. |
| 5,867,763 A | 2/1999 | Dean et al. |
| 5,870,427 A | 2/1999 | Tiedemann et al. |
| 5,870,431 A | 2/1999 | Easton et al. |
| 5,870,631 A | 2/1999 | Murray et al. |
| 5,870,674 A | 2/1999 | English |
| 5,872,481 A | 2/1999 | Sevic et al. |
| 5,872,774 A | 2/1999 | Wheatley et al. |
| 5,872,775 A | 2/1999 | Saints et al. |
| 5,872,823 A | 2/1999 | Sutton |
| 5,877,942 A | 3/1999 | Kida et al. |
| 5,878,036 A | 3/1999 | Spartz et al. |
| 5,881,053 A | 3/1999 | Kimball |
| 5,881,368 A | 3/1999 | Grob et al. |
| 5,884,157 A | 3/1999 | Karmi |
| 5,884,193 A | 3/1999 | Kaplan |
| 5,884,196 A | 3/1999 | Lekven et al. |
| 5,891,042 A | 4/1999 | Sham et al. |
| 5,892,178 A | 4/1999 | Reyes |
| 5,892,758 A | 4/1999 | Argyroudis |
| 5,892,774 A | 4/1999 | Zehavi et al. |
| 5,892,816 A | 4/1999 | Sih et al. |
| 5,892,916 A | 4/1999 | Gehlhaar et al. |
| 5,893,035 A | 4/1999 | Chen |
| 5,898,920 A | 4/1999 | Jacobs |
| 5,903,554 A | 5/1999 | Saints |
| 5,903,862 A | 5/1999 | Weaver et al. |
| 5,907,167 A | 5/1999 | Levin |
| 5,909,434 A | 6/1999 | Odenwalder et al. |
| 5,910,752 A | 6/1999 | Filipovic et al. |
| 5,911,128 A | 6/1999 | DeJaco |
| 5,912,882 A | 6/1999 | Yafuso et al. |
| 5,914,950 A | 6/1999 | Tiedemann et al. |
| 5,915,235 A | 6/1999 | DeJaco et al. |
| 5,917,708 A | 6/1999 | Moran et al. |
| 5,917,811 A | 6/1999 | Weaver et al. |
| 5,917,812 A | 6/1999 | Antonio et al. |
| 5,917,837 A | 6/1999 | Stein |
| 5,920,284 A | 7/1999 | Victor |
| 5,923,650 A | 7/1999 | Chen et al. |
| 5,923,705 A | 7/1999 | Willkie et al. |
| 5,926,143 A | 7/1999 | Tran |
| 5,926,470 A | 7/1999 | Tiedemann |
| 5,926,500 A | 7/1999 | Odenwalder |
| 5,926,786 A | 7/1999 | McDonough et al. |
| 5,928,156 A | 7/1999 | Krumbiegel et al. |
| 5,930,230 A | 7/1999 | Odenwalder et al. |
| 5,930,692 A | 7/1999 | Peterzell et al. |
| 5,945,928 A | 8/1999 | Kushler et al. |
| 5,953,541 A | 9/1999 | King et al. |
| 5,960,403 A | 9/1999 | Brown |
| 5,976,083 A | 11/1999 | Richardson et al. |
| 5,987,519 A | 11/1999 | Peifer et al. |
| 5,989,193 A * | 11/1999 | Sullivan | A61B 5/6892 600/534 |
| 6,005,951 A | 12/1999 | Grasfield et al. |
| 6,011,554 A | 1/2000 | King et al. |
| 6,014,432 A | 1/2000 | Modney |
| 6,024,575 A | 2/2000 | Ulrich |
| 6,026,366 A | 2/2000 | Grube |
| 6,061,647 A | 5/2000 | Barrett |
| 6,064,342 A | 5/2000 | Sandhu et al. |
| 6,075,470 A | 6/2000 | Little et al. |
| 6,102,856 A | 8/2000 | Groff et al. |
| 6,115,248 A | 9/2000 | Canova et al. |
| 6,132,337 A | 10/2000 | Krupka et al. |
| 6,135,966 A | 10/2000 | Ko |
| 6,139,494 A | 10/2000 | Cairnes |
| 6,139,505 A * | 10/2000 | Murphy | A61B 5/061 381/67 |
| 6,147,314 A | 11/2000 | Han et al. |
| 6,154,756 A | 11/2000 | Hearn |
| 6,185,423 B1 | 2/2001 | Brown et al. |
| 6,211,649 B1 | 4/2001 | Matsuda |
| 6,213,942 B1 | 4/2001 | Flach et al. |
| 6,219,694 B1 | 4/2001 | Lazaridis et al. |
| 6,222,857 B1 | 4/2001 | Kammer et al. |
| 6,224,549 B1 | 5/2001 | Drongelen |
| 6,228,040 B1 | 5/2001 | Craine |
| 6,231,521 B1 | 5/2001 | Zoth et al. |
| 6,238,338 B1 | 5/2001 | DeLuca et al. |
| 6,241,537 B1 | 6/2001 | Tate et al. |
| 6,271,605 B1 | 8/2001 | Carkner et al. |
| 6,272,333 B1 | 8/2001 | Smith |
| 6,278,442 B1 | 8/2001 | Griffin et al. |

(56) References Cited

U.S. PATENT DOCUMENTS

| | | |
|---|---|---|
| 6,312,382 B1 | 11/2001 | Mucci et al. |
| 6,315,719 B1 | 11/2001 | Rode et al. |
| 6,317,085 B1 | 11/2001 | Sandhu et al. |
| 6,319,207 B1 | 11/2001 | Naidoo |
| 6,322,521 B1 | 11/2001 | Hou |
| 6,327,495 B1 | 12/2001 | Iwabuchi et al. |
| 6,339,719 B1 | 1/2002 | Lee et al. |
| 6,344,848 B1 | 2/2002 | Rowe et al. |
| 6,364,834 B1 | 4/2002 | Reuss et al. |
| 6,368,283 B1 | 4/2002 | Xu et al. |
| 6,381,650 B1 | 4/2002 | Peacock |
| 6,388,877 B1 | 5/2002 | Canova et al. |
| 6,389,572 B1 | 5/2002 | Garrabrant et al. |
| 6,394,952 B1 | 5/2002 | Anderson et al. |
| 6,396,931 B1 | 5/2002 | Malilay |
| 6,398,727 B1 | 6/2002 | Bui et al. |
| 6,409,661 B1 | 6/2002 | Murphy |
| 6,409,662 B1 | 6/2002 | Lloyd et al. |
| 6,409,684 B1 | 6/2002 | Wilk |
| 6,416,471 B1 | 7/2002 | Kumar et al. |
| 6,423,013 B1 * | 7/2002 | Bakker ............... A61B 7/00 600/529 |
| 6,424,996 B1 | 7/2002 | Killcommons et al. |
| 6,425,087 B1 | 7/2002 | Osborn et al. |
| 6,428,475 B1 | 8/2002 | Shen |
| 6,429,625 B1 | 8/2002 | LeFevre et al. |
| 6,437,543 B1 | 8/2002 | Oler et al. |
| 6,440,082 B1 | 8/2002 | Joo et al. |
| 6,441,824 B2 | 8/2002 | Hertzfeld |
| 6,442,432 B2 | 8/2002 | Lee |
| 6,442,637 B1 | 8/2002 | Hawkins et al. |
| 6,450,953 B1 | 9/2002 | Place et al. |
| 6,454,708 B1 | 9/2002 | Ferguson et al. |
| 6,456,247 B1 | 9/2002 | Hulick et al. |
| 6,457,134 B1 | 9/2002 | Lemke et al. |
| 6,480,146 B1 | 11/2002 | Ferrandis et al. |
| 6,490,155 B2 | 12/2002 | Han et al. |
| 6,491,629 B1 | 12/2002 | Bousseljot et al. |
| 6,493,568 B1 | 12/2002 | Bell et al. |
| 6,494,829 B1 | 12/2002 | New, Jr. et al. |
| 6,497,656 B1 | 12/2002 | Evans et al. |
| 6,512,456 B1 | 1/2003 | Taylor, Jr. |
| 6,512,830 B1 | 1/2003 | Orten |
| 6,514,199 B1 | 2/2003 | Alessandri |
| 6,516,202 B1 | 2/2003 | Hawkins et al. |
| 6,516,289 B2 | 2/2003 | David |
| 6,519,141 B2 | 2/2003 | Tseng et al. |
| 6,523,124 B1 | 2/2003 | Lunsford et al. |
| 6,525,670 B1 | 2/2003 | Doi et al. |
| 6,532,148 B2 | 3/2003 | Jenks et al. |
| 6,533,736 B1 | 3/2003 | Moore |
| 6,537,233 B1 | 3/2003 | Rangayyan et al. |
| 6,539,476 B1 | 3/2003 | Marianetti et al. |
| 6,544,170 B1 | 4/2003 | Kajihara et al. |
| 6,544,174 B2 | 4/2003 | West et al. |
| 6,544,198 B2 | 4/2003 | Chong et al. |
| 6,549,566 B1 | 4/2003 | Lee et al. |
| 6,551,243 B2 | 4/2003 | Bocionek et al. |
| 6,551,251 B2 | 4/2003 | Zuckerwar et al. |
| 6,556,861 B1 | 4/2003 | Prichep |
| 6,558,321 B1 | 5/2003 | Burd et al. |
| 6,572,560 B1 | 6/2003 | Watrous et al. |
| 6,575,916 B2 | 6/2003 | Halleck et al. |
| 6,579,231 B1 | 6/2003 | Phipps |
| 6,582,365 B1 | 6/2003 | Hines et al. |
| 6,589,169 B1 | 7/2003 | Surwit et al. |
| 6,589,170 B1 | 7/2003 | Flach et al. |
| 6,589,189 B2 | 7/2003 | Meyerson et al. |
| 6,590,588 B2 | 7/2003 | Lincke et al. |
| 6,598,084 B1 | 7/2003 | Edwards et al. |
| 6,599,241 B1 | 7/2003 | Murphy |
| 6,602,191 B2 | 8/2003 | Quy |
| 6,605,038 B1 | 8/2003 | Teller et al. |
| 6,610,010 B2 | 8/2003 | Sjoqvist |
| 6,610,012 B2 | 8/2003 | Mault |
| 6,610,018 B1 | 8/2003 | McIntyre |
| 6,616,606 B1 | 9/2003 | Petersen et al. |
| 6,616,613 B1 | 9/2003 | Goodman |
| 6,618,044 B1 | 9/2003 | Gettemy et al. |
| 6,620,093 B2 | 9/2003 | Waldmann et al. |
| 6,626,842 B2 | 9/2003 | Oka |
| 6,629,938 B1 | 10/2003 | Engvall et al. |
| 6,641,533 B2 | 11/2003 | Causey, III et al. |
| 6,644,120 B1 | 11/2003 | Braun et al. |
| 6,648,820 B1 | 11/2003 | Sarel |
| 6,656,115 B1 | 12/2003 | Miyazaki et al. |
| 6,661,161 B1 | 12/2003 | Lanzo et al. |
| 6,665,803 B2 | 12/2003 | Lunsford et al. |
| 6,674,862 B1 | 1/2004 | Magilen |
| 6,685,328 B1 | 2/2004 | Hanson et al. |
| 6,685,633 B2 | 2/2004 | Albert et al. |
| 6,687,839 B1 | 2/2004 | Tate et al. |
| 6,692,446 B2 | 2/2004 | Hoek |
| 6,694,180 B1 | 2/2004 | Boesen |
| 6,696,956 B1 | 2/2004 | Uchida et al. |
| 6,697,639 B2 | 2/2004 | Andress |
| 6,699,204 B1 * | 3/2004 | Kehyayan ............ A61B 7/003 600/529 |
| 6,705,990 B1 | 3/2004 | Gallant et al. |
| 6,706,002 B1 | 3/2004 | Halleck et al. |
| 6,708,280 B1 | 3/2004 | Tate et al. |
| 6,712,638 B2 | 3/2004 | Fisher et al. |
| 6,719,707 B1 | 4/2004 | Montgomery |
| 6,721,892 B1 | 4/2004 | Osborn et al. |
| 6,723,045 B2 | 4/2004 | Cosentino et al. |
| 6,723,046 B2 | 4/2004 | Lichtenstein et al. |
| 6,724,720 B1 | 4/2004 | Skinner |
| 6,726,635 B1 | 4/2004 | LaSala |
| 6,727,814 B2 | 4/2004 | Saltzstein et al. |
| 6,732,105 B1 | 5/2004 | Watson et al. |
| 6,734,856 B2 | 5/2004 | Ishikawa et al. |
| 6,738,852 B1 | 5/2004 | Osborn |
| 6,740,033 B1 | 5/2004 | Olejniczak et al. |
| 6,744,451 B1 | 6/2004 | Anderson et al. |
| 6,745,047 B1 | 6/2004 | Karstens et al. |
| 6,746,960 B2 | 6/2004 | Goodman |
| 6,749,566 B2 | 6/2004 | Russ |
| 6,766,490 B1 | 7/2004 | Garrabrant et al. |
| 6,773,396 B2 | 8/2004 | Flach et al. |
| 6,781,575 B1 | 8/2004 | Hawkins et al. |
| 6,781,824 B2 | 8/2004 | Krieger et al. |
| 6,783,492 B2 | 8/2004 | Dominguez et al. |
| 6,786,873 B2 | 9/2004 | Zoth et al. |
| 6,788,285 B2 | 9/2004 | Paolucci et al. |
| 6,790,178 B1 | 9/2004 | Mault et al. |
| 6,795,710 B1 | 9/2004 | Creemer |
| 6,801,137 B2 | 10/2004 | Eggers |
| 6,804,699 B1 | 10/2004 | Henrie |
| 6,819,552 B1 | 11/2004 | Lam et al. |
| 6,820,057 B1 | 11/2004 | Loch et al. |
| 6,824,519 B2 | 11/2004 | Narimatsu et al. |
| 6,831,662 B1 | 12/2004 | Lum et al. |
| 6,840,908 B2 | 1/2005 | Edwards et al. |
| 6,842,335 B1 | 1/2005 | Hanson et al. |
| 6,842,628 B1 | 1/2005 | Arnold et al. |
| 6,845,161 B2 | 1/2005 | Boss |
| 6,845,263 B2 | 1/2005 | Kawaguchi |
| 6,845,408 B1 | 1/2005 | Lemke et al. |
| 6,847,959 B1 | 1/2005 | Arrouye |
| 6,850,780 B1 | 2/2005 | Gioscia et al. |
| 6,852,084 B1 | 2/2005 | Boesen |
| 6,858,006 B2 | 2/2005 | MacCarter et al. |
| 6,863,641 B1 | 3/2005 | Brown et al. |
| 6,865,424 B2 | 3/2005 | Daum et al. |
| 6,866,639 B2 | 3/2005 | Causevic et al. |
| 6,870,484 B1 | 3/2005 | Brinsfield et al. |
| 6,876,750 B2 | 4/2005 | Allred et al. |
| 6,878,117 B1 | 4/2005 | Watrous |
| 6,893,400 B2 | 5/2005 | Kawaguchi et al. |
| 6,897,788 B2 | 5/2005 | Khair et al. |
| 6,901,276 B1 | 5/2005 | Skinner et al. |
| 6,902,513 B1 | 6/2005 | McClure |
| 6,903,657 B2 | 6/2005 | Kwoen |
| 6,906,701 B1 | 6/2005 | Oueslati et al. |

(56) References Cited

U.S. PATENT DOCUMENTS

| | | |
|---|---|---|
| 6,906,741 B2 | 6/2005 | Canova et al. |
| 6,907,233 B1 | 6/2005 | Johnson et al. |
| 6,911,916 B1 | 6/2005 | Wang et al. |
| 6,916,291 B2 | 7/2005 | Givens et al. |
| 6,918,878 B2 | 7/2005 | Brodnick |
| 6,923,770 B2 | 8/2005 | Narimatsu |
| 6,924,752 B2 | 8/2005 | Gettemy et al. |
| 6,939,308 B2 | 9/2005 | Chassaing et al. |
| 6,940,490 B1 | 9/2005 | Kim et al. |
| 6,942,616 B2 | 9/2005 | Kerr, II |
| 6,943,667 B1 | 9/2005 | Kammer et al. |
| 6,944,821 B1 | 9/2005 | Bates et al. |
| 6,945,935 B1 | 9/2005 | Sasse et al. |
| 6,947,017 B1 | 9/2005 | Gettemy |
| 6,947,975 B2 | 9/2005 | Wong et al. |
| 6,950,988 B1 | 9/2005 | Hawkins et al. |
| 6,952,571 B1 | 10/2005 | Garrabrant et al. |
| 6,953,436 B2 | 10/2005 | Watrous et al. |
| 6,956,572 B2 | 10/2005 | Zaleski |
| 6,957,102 B2 | 10/2005 | Silver et al. |
| 6,957,397 B1 | 10/2005 | Hawkins et al. |
| 6,960,167 B2 | 11/2005 | Bardy |
| 6,961,029 B1 | 11/2005 | Canova et al. |
| 6,961,567 B1 | 11/2005 | Kuhn |
| 6,965,375 B1 | 11/2005 | Gettemy et al. |
| 6,975,304 B1 | 12/2005 | Hawkins et al. |
| 6,984,207 B1 | 1/2006 | Sullivan et al. |
| 6,988,989 B2 | 1/2006 | Weiner et al. |
| 6,988,993 B2 | 1/2006 | Sullivan et al. |
| 6,994,675 B2 | 2/2006 | Sharrock |
| 6,997,852 B2 | 2/2006 | Watterson et al. |
| 6,999,592 B2 | 2/2006 | Chelen |
| 6,999,816 B2 | 2/2006 | Van Bentem |
| 7,001,338 B2 | 2/2006 | Hayek et al. |
| 7,003,121 B1 | 2/2006 | Arknaes-Pedersen |
| 7,003,122 B2 | 2/2006 | Chen |
| 7,006,638 B1 | 2/2006 | Baekgaard et al. |
| 7,007,239 B1 | 2/2006 | Hawkins et al. |
| 7,010,342 B2 | 3/2006 | Galen et al. |
| 7,024,000 B1 | 4/2006 | Gabara et al. |
| 7,031,745 B2 | 4/2006 | Shen |
| 7,037,274 B2 | 5/2006 | Thornton et al. |
| 7,038,588 B2 | 5/2006 | Boone et al. |
| 7,044,922 B1 | 5/2006 | Dondysh |
| 7,050,592 B1 | 5/2006 | Iseberg et al. |
| 7,052,466 B2 | 5/2006 | Scheiner et al. |
| 7,054,449 B2 | 5/2006 | Ludi |
| 7,058,182 B2 | 6/2006 | Kates |
| 7,062,225 B2 | 6/2006 | White |
| 7,063,665 B2 | 6/2006 | Hasegawa et al. |
| 7,074,183 B2 | 7/2006 | Castellanos |
| 7,074,195 B2 | 7/2006 | Nelson et al. |
| 7,091,879 B2 | 8/2006 | Swetlik et al. |
| 7,098,803 B2 | 8/2006 | Mann et al. |
| 7,103,578 B2 | 9/2006 | Beck et al. |
| 7,104,954 B2 | 9/2006 | Koyama et al. |
| 7,104,955 B2 | 9/2006 | Bardy |
| 7,107,095 B2 | 9/2006 | Manolas |
| 7,120,477 B2 | 10/2006 | Huang |
| 7,133,715 B1 | 11/2006 | Smits et al. |
| 7,134,994 B2 | 11/2006 | Alpert et al. |
| 7,134,996 B2 | 11/2006 | Bardy |
| 7,135,002 B2 | 11/2006 | Sullivan |
| 7,135,987 B1 | 11/2006 | LaMotte et al. |
| 7,137,946 B2 | 11/2006 | Waldmann |
| 7,137,955 B2 | 11/2006 | Bartels et al. |
| 7,155,202 B2 | 12/2006 | Helal |
| 7,165,062 B2 | 1/2007 | O'Rourke |
| 7,171,166 B2 | 1/2007 | Ng et al. |
| 7,174,203 B2 | 2/2007 | Arand et al. |
| 7,190,795 B2 | 3/2007 | Simon |
| 7,190,994 B2 | 3/2007 | Mohler et al. |
| 7,194,292 B2 | 3/2007 | Norris |
| 7,206,636 B1 | 4/2007 | Turcott |
| 7,209,796 B2 | 4/2007 | McKinney et al. |
| 7,215,991 B2 | 5/2007 | Besson et al. |
| 7,222,054 B2 | 5/2007 | Geva |
| 7,254,516 B2 | 8/2007 | Case, Jr. et al. |
| 7,258,671 B2 | 8/2007 | Wasden |
| 7,260,369 B2 | 8/2007 | Feher |
| 7,260,429 B2 | 8/2007 | Siejko et al. |
| 7,266,391 B2 | 9/2007 | Warren |
| 7,267,652 B2 | 9/2007 | Coyle |
| 7,288,071 B2 | 10/2007 | Harrison et al. |
| 7,288,072 B2 | 10/2007 | Stott et al. |
| 7,289,786 B2 | 10/2007 | Krasner |
| 7,302,290 B2 | 11/2007 | Bauer |
| 7,303,530 B2 | 12/2007 | Barnes et al. |
| 7,340,240 B2 | 3/2008 | McDonald |
| 7,346,174 B1 | 3/2008 | Smith |
| 7,351,207 B2 | 4/2008 | Priemer |
| 7,366,307 B2 | 4/2008 | Yanz et al. |
| 7,383,065 B2 | 6/2008 | Skinner et al. |
| 7,392,193 B2 | 6/2008 | Mault |
| 7,402,143 B2 | 7/2008 | Berger et al. |
| 7,424,321 B2 | 9/2008 | Wariar et al. |
| 7,431,699 B2 | 10/2008 | Siejko et al. |
| 7,438,689 B2 | 10/2008 | Munk |
| 7,452,337 B2 | 11/2008 | Iseberg |
| 7,454,002 B1 | 11/2008 | Gardner et al. |
| 7,465,277 B2 | 12/2008 | Wasden et al. |
| 7,479,112 B2 | 1/2009 | Sweeney et al. |
| 7,479,949 B2 | 1/2009 | Jobs et al. |
| 7,480,870 B2 | 1/2009 | Anzures et al. |
| 7,488,292 B2 | 2/2009 | Adachi |
| 7,507,203 B2 | 3/2009 | Sebastian et al. |
| 7,513,871 B2 | 4/2009 | Phillips |
| 7,515,948 B1 | 4/2009 | Balberg et al. |
| 7,529,379 B2 | 5/2009 | Zurek et al. |
| 7,530,957 B2 | 5/2009 | Givens et al. |
| 7,539,487 B2 | 5/2009 | Sinclair et al. |
| 7,539,532 B2 | 5/2009 | Tran |
| 7,539,534 B2 | 5/2009 | Orenstein et al. |
| 7,547,278 B2 | 6/2009 | Miyazaki et al. |
| 7,559,901 B2 | 7/2009 | Maile et al. |
| 7,585,279 B2 | 9/2009 | Carlson et al. |
| 7,590,772 B2 | 9/2009 | Marriott et al. |
| 7,593,534 B2 | 9/2009 | Andersen |
| 7,593,765 B2 | 9/2009 | Rapoport et al. |
| 7,593,782 B2 | 9/2009 | Jobs et al. |
| 7,609,843 B2 | 10/2009 | Hatano et al. |
| 7,611,471 B2 | 11/2009 | Thiagarajan |
| 7,616,110 B2 | 11/2009 | Crump et al. |
| 7,643,895 B2 | 1/2010 | Gupta et al. |
| 7,668,589 B2 | 2/2010 | Bauer |
| 7,691,068 B2 | 4/2010 | Felder et al. |
| 7,692,667 B2 | 4/2010 | Nguyen et al. |
| 7,695,441 B2 | 4/2010 | Harrison et al. |
| 7,721,843 B1 | 5/2010 | Belenger et al. |
| 7,727,157 B2 | 6/2010 | Sharrock |
| 7,736,321 B2 | 6/2010 | Wasden et al. |
| 7,761,141 B2 | 7/2010 | Hirsh |
| 7,761,302 B2 | 7/2010 | Woodcock et al. |
| 7,762,470 B2 | 7/2010 | Finn et al. |
| 7,766,826 B2 | 8/2010 | Lee et al. |
| 7,780,606 B2 | 8/2010 | Carlson et al. |
| 7,786,975 B2 | 8/2010 | Ording et al. |
| 7,812,826 B2 | 10/2010 | Ording et al. |
| 7,813,715 B2 | 10/2010 | McKillop et al. |
| 7,818,050 B2 | 10/2010 | Rapoport et al. |
| 7,819,814 B2 | 10/2010 | Gavriely et al. |
| 7,828,740 B2 | 11/2010 | Longhini et al. |
| 7,831,199 B2 | 11/2010 | Ng et al. |
| 7,856,035 B2 | 12/2010 | Pierce et al. |
| 7,860,725 B2 | 12/2010 | Gopinathan et al. |
| 7,860,731 B2 | 12/2010 | Jackson et al. |
| 7,874,993 B2 | 1/2011 | Bardy |
| 7,881,743 B2 | 2/2011 | Griffin et al. |
| 7,896,807 B2 | 3/2011 | Clancy et al. |
| 7,903,827 B1 | 3/2011 | Lockwood et al. |
| 7,904,528 B2 | 3/2011 | Zilliacus et al. |
| 7,909,772 B2 | 3/2011 | Popov et al. |
| 7,922,669 B2 | 4/2011 | Zhang et al. |
| 7,930,886 B2 | 4/2011 | Shin et al. |

(56) References Cited

U.S. PATENT DOCUMENTS

| | | | |
|---|---|---|---|
| 7,951,087 B2 | 5/2011 | Siejko et al. | |
| 7,953,230 B2 | 5/2011 | Nadjar et al. | |
| 7,965,851 B2 | 6/2011 | Bengtsson | |
| 7,976,473 B2 | 7/2011 | Causevic | |
| 7,985,164 B2 | 7/2011 | Ashby | |
| 7,993,275 B2 | 8/2011 | Banet et al. | |
| 7,998,091 B2 | 8/2011 | Carim et al. | |
| 8,024,974 B2 | 9/2011 | Bharti et al. | |
| 8,073,984 B2 | 12/2011 | Lydon et al. | |
| 8,090,130 B2 | 1/2012 | Zorkendorfer et al. | |
| 8,095,073 B2 | 1/2012 | Hayes et al. | |
| 8,135,798 B2 | 3/2012 | Welingkar et al. | |
| 8,157,731 B2 | 4/2012 | Teller et al. | |
| 8,165,893 B1 | 4/2012 | Goldberg et al. | |
| 8,170,887 B2 | 5/2012 | Rosenfeld et al. | |
| 8,200,320 B2 | 6/2012 | Kovacs | |
| 8,219,928 B2 | 7/2012 | Tsukazaki et al. | |
| 8,239,784 B2 | 8/2012 | Hotelling et al. | |
| 8,323,190 B2 * | 12/2012 | Vitiello | A61B 5/0002 600/300 |
| 8,398,560 B2 * | 3/2013 | Elser | A61B 5/0059 600/534 |
| 8,690,799 B2 * | 4/2014 | Telfort | A61B 7/003 29/594 |
| 8,771,204 B2 * | 7/2014 | Telfort | A61B 5/6843 600/586 |
| 2001/0014162 A1 | 8/2001 | Orten | |
| 2001/0017598 A1 | 8/2001 | Townsend et al. | |
| 2001/0029321 A1 | 10/2001 | Beetz et al. | |
| 2001/0030077 A1 | 10/2001 | Watson | |
| 2001/0034475 A1 | 10/2001 | Flach et al. | |
| 2001/0039383 A1 | 11/2001 | Mohler | |
| 2001/0041845 A1 | 11/2001 | Kim | |
| 2001/0050992 A1 | 12/2001 | Carman | |
| 2001/0056226 A1 | 12/2001 | Zodnik et al. | |
| 2002/0001390 A1 | 1/2002 | Kawaguchi | |
| 2002/0013517 A1 | 1/2002 | West et al. | |
| 2002/0013518 A1 | 1/2002 | West et al. | |
| 2002/0019584 A1 | 2/2002 | Schulze et al. | |
| 2002/0019586 A1 | 2/2002 | Teller et al. | |
| 2002/0022775 A1 | 2/2002 | Finkelshteins | |
| 2002/0028989 A1 | 3/2002 | Pelletier et al. | |
| 2002/0035332 A1 | 3/2002 | Chen et al. | |
| 2002/0038089 A1 | 3/2002 | Watrous | |
| 2002/0049371 A1 | 4/2002 | Lai et al. | |
| 2002/0052559 A1 | 5/2002 | Watrous | |
| 2002/0055684 A1 | 5/2002 | Patterson | |
| 2002/0058861 A1 | 5/2002 | Drew | |
| 2002/0058889 A1 | 5/2002 | Lee | |
| 2002/0062070 A1 | 5/2002 | Tschupp et al. | |
| 2002/0071570 A1 | 6/2002 | Cohen et al. | |
| 2002/0076056 A1 | 6/2002 | Pavlakos | |
| 2002/0085724 A1 | 7/2002 | Grasfield et al. | |
| 2002/0091309 A1 | 7/2002 | Auer | |
| 2002/0091310 A1 | 7/2002 | Jentsch et al. | |
| 2002/0099281 A1 | 7/2002 | Bahr et al. | |
| 2002/0099286 A1 | 7/2002 | Sandler et al. | |
| 2002/0103422 A1 | 8/2002 | Harder et al. | |
| 2002/0107450 A1 | 8/2002 | Ogura | |
| 2002/0109621 A1 | 8/2002 | Khair et al. | |
| 2002/0123671 A1 | 9/2002 | Haaland | |
| 2002/0126036 A1 | 9/2002 | Flaherty et al. | |
| 2002/0143241 A1 | 10/2002 | Thorell | |
| 2002/0151771 A1 | 10/2002 | Braun et al. | |
| 2002/0156398 A1 | 10/2002 | Mansy et al. | |
| 2002/0165466 A1 | 11/2002 | Givens et al. | |
| 2002/0173704 A1 | 11/2002 | Schulze et al. | |
| 2002/0173707 A1 | 11/2002 | Lynn et al. | |
| 2002/0188183 A1 | 12/2002 | Kusakabe et al. | |
| 2002/0188227 A1 | 12/2002 | Chong et al. | |
| 2003/0002685 A1 * | 1/2003 | Werblud | A61B 7/04 381/67 |
| 2003/0009088 A1 | 1/2003 | Korth et al. | |
| 2003/0013438 A1 | 1/2003 | Darby | |
| 2003/0017833 A1 | 1/2003 | Forrester | |
| 2003/0018276 A1 | 1/2003 | Mansy et al. | |
| 2003/0032868 A1 | 2/2003 | Graskov et al. | |
| 2003/0033144 A1 | 2/2003 | Silverman et al. | |
| 2003/0036683 A1 | 2/2003 | Kehr et al. | |
| 2003/0036685 A1 | 2/2003 | Goodman | |
| 2003/0050538 A1 | 3/2003 | Naghavi et al. | |
| 2003/0055321 A1 | 3/2003 | Watrous et al. | |
| 2003/0055352 A1 | 3/2003 | Hayek et al. | |
| 2003/0055359 A1 | 3/2003 | Halleck et al. | |
| 2003/0065253 A1 | 4/2003 | Stivoric et al. | |
| 2003/0065714 A1 | 4/2003 | Wong et al. | |
| 2003/0069481 A1 | 4/2003 | Hervy et al. | |
| 2003/0072457 A1 | 4/2003 | Grasfield et al. | |
| 2003/0073884 A1 | 4/2003 | Goldberg | |
| 2003/0073926 A1 | 4/2003 | Johansen et al. | |
| 2003/0092971 A1 | 5/2003 | Intrator | |
| 2003/0093002 A1 * | 5/2003 | Kuo | A61B 5/02405 600/528 |
| 2003/0095148 A1 | 5/2003 | Dinstein et al. | |
| 2003/0097075 A1 | 5/2003 | Kuo | |
| 2003/0107529 A1 | 6/2003 | Hayhurst et al. | |
| 2003/0117296 A1 | 6/2003 | Seely | |
| 2003/0120134 A1 | 6/2003 | Rao et al. | |
| 2003/0120159 A1 | 6/2003 | Mohler | |
| 2003/0122677 A1 | 7/2003 | Kail, IV | |
| 2003/0130567 A1 | 7/2003 | Mault et al. | |
| 2003/0135094 A1 | 7/2003 | Illyes et al. | |
| 2003/0139679 A1 | 7/2003 | Kushnir et al. | |
| 2003/0144579 A1 | 7/2003 | Buss | |
| 2003/0149344 A1 | 8/2003 | Nizan | |
| 2003/0153817 A1 | 8/2003 | Knagenhjelm | |
| 2003/0153818 A1 | 8/2003 | Bocionek et al. | |
| 2003/0158693 A1 | 8/2003 | Kai | |
| 2003/0163051 A1 | 8/2003 | Eckerle et al. | |
| 2003/0166994 A1 | 9/2003 | Ooshima et al. | |
| 2003/0166995 A1 | 9/2003 | Jansen | |
| 2003/0166996 A1 | 9/2003 | Kim et al. | |
| 2003/0167188 A1 | 9/2003 | Hashiguchi et al. | |
| 2003/0176801 A1 | 9/2003 | Galen et al. | |
| 2003/0187336 A1 | 10/2003 | Odagiri et al. | |
| 2003/0190023 A1 | 10/2003 | Farkas et al. | |
| 2003/0191373 A1 | 10/2003 | Blike | |
| 2003/0195399 A1 | 10/2003 | Phipps | |
| 2003/0204131 A1 | 10/2003 | Aschoff et al. | |
| 2003/0208130 A1 | 11/2003 | Yotam et al. | |
| 2003/0212348 A1 | 11/2003 | Lambert | |
| 2003/0216625 A1 | 11/2003 | Phipps | |
| 2003/0225317 A1 | 12/2003 | Schell | |
| 2004/0002634 A1 | 1/2004 | Nihtila | |
| 2004/0019261 A1 | 1/2004 | Gopinathan et al. | |
| 2004/0027246 A1 | 2/2004 | Aguglia | |
| 2004/0028236 A1 | 2/2004 | Chelen | |
| 2004/0030225 A1 | 2/2004 | Nunome | |
| 2004/0030226 A1 | 2/2004 | Quy | |
| 2004/0030581 A1 | 2/2004 | Leven | |
| 2004/0030672 A1 | 2/2004 | Garwin | |
| 2004/0032957 A1 | 2/2004 | Mansy et al. | |
| 2004/0034289 A1 | 2/2004 | Teller et al. | |
| 2004/0037429 A1 | 2/2004 | Candioty | |
| 2004/0039256 A1 | 2/2004 | Kawatahara et al. | |
| 2004/0039263 A1 | 2/2004 | Bardy | |
| 2004/0039294 A1 * | 2/2004 | Sullivan | A61B 7/003 600/528 |
| 2004/0049125 A1 | 3/2004 | Nakamura | |
| 2004/0052394 A1 | 3/2004 | Watmough et al. | |
| 2004/0054302 A1 | 3/2004 | Czernicki | |
| 2004/0064056 A1 | 4/2004 | Ogura | |
| 2004/0064343 A1 | 4/2004 | Korpman et al. | |
| 2004/0068194 A1 | 4/2004 | Johnson et al. | |
| 2004/0073094 A1 | 4/2004 | Baker | |
| 2004/0073455 A1 | 4/2004 | McConnochie et al. | |
| 2004/0076303 A1 | 4/2004 | Vyshedskiy et al. | |
| 2004/0077974 A1 | 4/2004 | Moore | |
| 2004/0078219 A1 | 4/2004 | Kaylor et al. | |
| 2004/0082840 A1 | 4/2004 | Chen | |
| 2004/0087839 A1 | 5/2004 | Raymond et al. | |
| 2004/0092801 A1 | 5/2004 | Drakulic | |
| 2004/0092846 A1 | 5/2004 | Watrous | |

(56) References Cited

U.S. PATENT DOCUMENTS

| | | |
|---|---|---|
| 2004/0096069 A1 | 5/2004 | Jen-Chien |
| 2004/0100376 A1 | 5/2004 | Lye et al. |
| 2004/0102683 A1 | 5/2004 | Khanuja et al. |
| 2004/0102685 A1 | 5/2004 | Cosentino et al. |
| 2004/0103001 A1 | 5/2004 | Mazar et al. |
| 2004/0105556 A1 | 6/2004 | Grove |
| 2004/0109571 A1 | 6/2004 | Yoshimine |
| 2004/0111034 A1 | 6/2004 | Lin et al. |
| 2004/0114767 A1 | 6/2004 | Tseng |
| 2004/0116785 A1 | 6/2004 | Bulat |
| 2004/0122296 A1 | 6/2004 | Hatlestad et al. |
| 2004/0128161 A1 | 7/2004 | Mazar et al. |
| 2004/0133109 A1 | 7/2004 | Crowley et al. |
| 2004/0143191 A1 | 7/2004 | Faisandier |
| 2004/0147818 A1 | 7/2004 | Levy et al. |
| 2004/0148193 A1 | 7/2004 | Blackburn |
| 2004/0148199 A1 | 7/2004 | Dixon, Jr. |
| 2004/0152956 A1 | 8/2004 | Korman |
| 2004/0152957 A1 | 8/2004 | Stivoric et al. |
| 2004/0153007 A1 | 8/2004 | Harris et al. |
| 2004/0153289 A1 | 8/2004 | Casey et al. |
| 2004/0157612 A1 | 8/2004 | Kim |
| 2004/0162466 A1 | 8/2004 | Quy |
| 2004/0167417 A1 | 8/2004 | Schulhauser et al. |
| 2004/0169673 A1 | 9/2004 | Crampe et al. |
| 2004/0170285 A1 | 9/2004 | Baekgaard et al. |
| 2004/0171965 A1 | 9/2004 | Zoth et al. |
| 2004/0179664 A1 | 9/2004 | Platt et al. |
| 2004/0184632 A1 | 9/2004 | Minervini |
| 2004/0193022 A1 | 9/2004 | Torii et al. |
| 2004/0193064 A1 | 9/2004 | Shusterman |
| 2004/0199056 A1 | 10/2004 | Husemann et al. |
| 2004/0204633 A1 | 10/2004 | Rentea et al. |
| 2004/0220487 A1 | 11/2004 | Vyshedskiy et al. |
| 2004/0220488 A1 | 11/2004 | Vyshedskiy et al. |
| 2004/0223621 A1 | 11/2004 | Orten |
| 2004/0224638 A1 | 11/2004 | Fadell et al. |
| 2004/0225199 A1 | 11/2004 | Evanyk et al. |
| 2004/0225476 A1 | 11/2004 | Tien |
| 2004/0228494 A1 | 11/2004 | Smith |
| 2004/0230128 A1* | 11/2004 | Brockway ............. A61N 1/05 600/510 |
| 2004/0233930 A1 | 11/2004 | Colby |
| 2004/0236190 A1 | 11/2004 | Lee et al. |
| 2004/0236239 A1 | 11/2004 | Murray et al. |
| 2004/0236241 A1 | 11/2004 | Murphy |
| 2004/0236608 A1 | 11/2004 | Ruggio et al. |
| 2004/0242972 A1 | 12/2004 | Adak et al. |
| 2004/0243017 A1 | 12/2004 | Causevic |
| 2004/0249293 A1 | 12/2004 | Sandler et al. |
| 2004/0254429 A1 | 12/2004 | Yang |
| 2004/0254430 A1 | 12/2004 | Hamilton |
| 2004/0260154 A1 | 12/2004 | Sidelnik et al. |
| 2004/0260188 A1 | 12/2004 | Syed et al. |
| 2004/0267145 A1 | 12/2004 | Daniel et al. |
| 2004/0267148 A1 | 12/2004 | Arand et al. |
| 2004/0267149 A1 | 12/2004 | Kushnir et al. |
| 2005/0004460 A1 | 1/2005 | Taylor et al. |
| 2005/0010087 A1 | 1/2005 | Banet et al. |
| 2005/0010444 A1 | 1/2005 | Iliff |
| 2005/0014999 A1 | 1/2005 | Rahe-Meyer |
| 2005/0020887 A1 | 1/2005 | Goldberg |
| 2005/0021370 A1 | 1/2005 | Riff et al. |
| 2005/0027567 A1 | 2/2005 | Taha |
| 2005/0033120 A1 | 2/2005 | Cohen |
| 2005/0033144 A1 | 2/2005 | Wada |
| 2005/0033147 A1 | 2/2005 | Wada et al. |
| 2005/0033198 A1 | 2/2005 | Kehyayan et al. |
| 2005/0038326 A1 | 2/2005 | Mathur |
| 2005/0038328 A1 | 2/2005 | Stoehrer et al. |
| 2005/0038360 A1 | 2/2005 | Shertukde |
| 2005/0043642 A1 | 2/2005 | Sauerland |
| 2005/0043643 A1* | 2/2005 | Priemer ............. A61B 7/023 600/528 |
| 2005/0057684 A1 | 3/2005 | Tamakoshi |
| 2005/0058298 A1 | 3/2005 | Smith |
| 2005/0061336 A1 | 3/2005 | Goetz et al. |
| 2005/0062637 A1 | 3/2005 | El Zabadani et al. |
| 2005/0070767 A1 | 3/2005 | Maschke |
| 2005/0071303 A1 | 3/2005 | de Voir et al. |
| 2005/0071304 A1 | 3/2005 | Schomburg |
| 2005/0074130 A1 | 4/2005 | Brummel et al. |
| 2005/0075542 A1 | 4/2005 | Goldreich |
| 2005/0075583 A1 | 4/2005 | Sullivan |
| 2005/0076909 A1 | 4/2005 | Stahmann et al. |
| 2005/0078533 A1 | 4/2005 | Vyshedskiy et al. |
| 2005/0080322 A1 | 4/2005 | Korman |
| 2005/0080652 A1 | 4/2005 | Brown |
| 2005/0084124 A1 | 4/2005 | Tien |
| 2005/0086083 A1 | 4/2005 | Brown |
| 2005/0088296 A1 | 4/2005 | Lee |
| 2005/0090282 A1 | 4/2005 | Murayama |
| 2005/0090285 A1 | 4/2005 | Murayama |
| 2005/0090755 A1 | 4/2005 | Guion et al. |
| 2005/0101841 A9 | 5/2005 | Kaylor et al. |
| 2005/0101843 A1 | 5/2005 | Quinn et al. |
| 2005/0101845 A1 | 5/2005 | Nihtila |
| 2005/0104685 A1 | 5/2005 | Kuroki et al. |
| 2005/0107715 A1 | 5/2005 | Abbruscato |
| 2005/0113648 A1 | 5/2005 | Yang et al. |
| 2005/0113653 A1 | 5/2005 | Fox et al. |
| 2005/0113703 A1* | 5/2005 | Farringdon .......... A61B 5/0428 600/509 |
| 2005/0113708 A1 | 5/2005 | Priemer |
| 2005/0116820 A1 | 6/2005 | Goldreich |
| 2005/0119533 A1 | 6/2005 | Sparks et al. |
| 2005/0119535 A1 | 6/2005 | Yanagihara et al. |
| 2005/0119584 A1 | 6/2005 | Carter |
| 2005/0119585 A1 | 6/2005 | Watrous |
| 2005/0124375 A1 | 6/2005 | Nowosielski |
| 2005/0124864 A1* | 6/2005 | Mack ................... A61B 5/024 600/300 |
| 2005/0124905 A1 | 6/2005 | Ogura |
| 2005/0127156 A1 | 6/2005 | Yoo et al. |
| 2005/0131308 A1 | 6/2005 | Chio et al. |
| 2005/0131652 A1 | 6/2005 | Corwin et al. |
| 2005/0136846 A1 | 6/2005 | Kim et al. |
| 2005/0137464 A1 | 6/2005 | Bomba |
| 2005/0140566 A1 | 6/2005 | Kim et al. |
| 2005/0146431 A1 | 7/2005 | Hastings et al. |
| 2005/0148883 A1 | 7/2005 | Boesen |
| 2005/0153692 A1 | 7/2005 | Hwang et al. |
| 2005/0154264 A1 | 7/2005 | Lecompte et al. |
| 2005/0154301 A1 | 7/2005 | Shahar et al. |
| 2005/0154935 A1 | 7/2005 | Jin |
| 2005/0157887 A1 | 7/2005 | Kim |
| 2005/0157888 A1 | 7/2005 | Yang |
| 2005/0159987 A1 | 7/2005 | Rosenfeld et al. |
| 2005/0163086 A1 | 7/2005 | Kang |
| 2005/0165317 A1 | 7/2005 | Turner et al. |
| 2005/0171410 A1 | 8/2005 | Hjelt et al. |
| 2005/0176403 A1 | 8/2005 | Lalos |
| 2005/0177312 A1 | 8/2005 | Guerrant et al. |
| 2005/0180253 A1 | 8/2005 | DiSanto et al. |
| 2005/0180581 A1 | 8/2005 | Botbol |
| 2005/0181361 A1 | 8/2005 | Kim |
| 2005/0182302 A1 | 8/2005 | Johnson et al. |
| 2005/0182342 A1 | 8/2005 | Dinsmoor et al. |
| 2005/0185799 A1 | 8/2005 | Bertram |
| 2005/0187796 A1 | 8/2005 | Rosenfeld et al. |
| 2005/0190062 A1 | 9/2005 | Sullivan et al. |
| 2005/0190727 A1 | 9/2005 | Vanlieshout et al. |
| 2005/0192487 A1 | 9/2005 | Cosentino et al. |
| 2005/0195760 A1 | 9/2005 | Lee et al. |
| 2005/0197141 A1 | 9/2005 | Jiang et al. |
| 2005/0197541 A1 | 9/2005 | Shitan |
| 2005/0197545 A1 | 9/2005 | Hoggle |
| 2005/0200436 A1 | 9/2005 | Lee et al. |
| 2005/0201351 A1 | 9/2005 | Nakao |
| 2005/0201566 A1 | 9/2005 | Hoover |
| 2005/0203349 A1 | 9/2005 | Nanikashvilli |
| 2005/0203350 A1 | 9/2005 | Beck |
| 2005/0206518 A1 | 9/2005 | Welch et al. |
| 2005/0214929 A1 | 9/2005 | Seher et al. |

(56) References Cited

U.S. PATENT DOCUMENTS

| | | |
|---|---|---|
| 2005/0220048 A1 | 10/2005 | Lee et al. |
| 2005/0221850 A1 | 10/2005 | Kashiwase |
| 2005/0222515 A1 | 10/2005 | Polyshchuk et al. |
| 2005/0226196 A1 | 10/2005 | Suh |
| 2005/0226227 A1 | 10/2005 | Kim et al. |
| 2005/0228234 A1 | 10/2005 | Yang |
| 2005/0228242 A1 | 10/2005 | Kawamura et al. |
| 2005/0234307 A1 | 10/2005 | Heinonen et al. |
| 2005/0234308 A1 | 10/2005 | Naukkarinen |
| 2005/0234314 A1* | 10/2005 | Suzuki .......... A61B 5/0205 600/301 |
| 2005/0234349 A1 | 10/2005 | Pravica et al. |
| 2005/0237961 A1 | 10/2005 | Yi et al. |
| 2005/0238051 A1 | 10/2005 | Yi et al. |
| 2005/0240084 A1 | 10/2005 | Morice et al. |
| 2005/0243978 A1 | 11/2005 | Son et al. |
| 2005/0245790 A1 | 11/2005 | Bergfalk et al. |
| 2005/0245793 A1 | 11/2005 | Hilton et al. |
| 2005/0249141 A1 | 11/2005 | Lee et al. |
| 2005/0250516 A1 | 11/2005 | Shim |
| 2005/0250995 A1 | 11/2005 | Quy |
| 2005/0256379 A1 | 11/2005 | Matory et al. |
| 2005/0261557 A1 | 11/2005 | Baker |
| 2005/0261559 A1 | 11/2005 | Mumford et al. |
| 2005/0265293 A1 | 12/2005 | Ro et al. |
| 2005/0266829 A1 | 12/2005 | Tran et al. |
| 2005/0266846 A1 | 12/2005 | Kim |
| 2005/0267337 A1 | 12/2005 | Sakai et al. |
| 2005/0267377 A1 | 12/2005 | Marossero et al. |
| 2005/0272403 A1 | 12/2005 | Ryu et al. |
| 2005/0280569 A1 | 12/2005 | Park |
| 2005/0283051 A1 | 12/2005 | Chen |
| 2005/0288559 A1 | 12/2005 | Feliss et al. |
| 2005/0289229 A1 | 12/2005 | Kim |
| 2006/0001550 A1 | 1/2006 | Mann et al. |
| 2006/0003694 A1 | 1/2006 | Quelle |
| 2006/0003733 A1 | 1/2006 | Chun et al. |
| 2006/0004265 A1 | 1/2006 | Pulkkinen et al. |
| 2006/0004266 A1 | 1/2006 | Shirai et al. |
| 2006/0008256 A1 | 1/2006 | Khedouri et al. |
| 2006/0009189 A1 | 1/2006 | Kim et al. |
| 2006/0009234 A1 | 1/2006 | Freer |
| 2006/0009817 A1 | 1/2006 | Tulkki |
| 2006/0010090 A1 | 1/2006 | Brockway et al. |
| 2006/0012559 A1 | 1/2006 | Kang |
| 2006/0015017 A1 | 1/2006 | Cosentino et al. |
| 2006/0016674 A1 | 1/2006 | Kim |
| 2006/0017563 A1 | 1/2006 | Rosenfeld et al. |
| 2006/0018278 A1 | 1/2006 | Grasfield |
| 2006/0018487 A1 | 1/2006 | Smith |
| 2006/0020220 A1* | 1/2006 | Bostian .......... G06F 19/00 600/528 |
| 2006/0020294 A1 | 1/2006 | Brockway et al. |
| 2006/0022956 A1 | 2/2006 | Lengeling et al. |
| 2006/0024047 A1 | 2/2006 | Lee |
| 2006/0025657 A1 | 2/2006 | Rosenfeld et al. |
| 2006/0026535 A1 | 2/2006 | Hotelling et al. |
| 2006/0026536 A1 | 2/2006 | Hotelling et al. |
| 2006/0030759 A1 | 2/2006 | Weiner et al. |
| 2006/0031378 A1 | 2/2006 | Vallapureddy et al. |
| 2006/0031924 A1 | 2/2006 | Kwon et al. |
| 2006/0033724 A1 | 2/2006 | Chaudhri et al. |
| 2006/0034225 A1 | 2/2006 | Jung et al. |
| 2006/0035645 A1 | 2/2006 | Kim |
| 2006/0035667 A1 | 2/2006 | Kim |
| 2006/0036134 A1 | 2/2006 | Tarassenko et al. |
| 2006/0036677 A1 | 2/2006 | Stout et al. |
| 2006/0037615 A1 | 2/2006 | Wilkinson et al. |
| 2006/0040662 A1 | 2/2006 | Kim et al. |
| 2006/0044401 A1 | 3/2006 | Park |
| 2006/0046687 A1 | 3/2006 | Kwon |
| 2006/0046777 A1 | 3/2006 | Oh |
| 2006/0046798 A1 | 3/2006 | Corrigan et al. |
| 2006/0047188 A1 | 3/2006 | Bohan |
| 2006/0047215 A1 | 3/2006 | Newman et al. |
| 2006/0048146 A1 | 3/2006 | Oh |
| 2006/0050007 A1 | 3/2006 | Min |
| 2006/0052676 A1 | 3/2006 | Wang et al. |
| 2006/0053102 A1 | 3/2006 | Kim |
| 2006/0053387 A1 | 3/2006 | Ording |
| 2006/0057981 A1 | 3/2006 | Tsuda |
| 2006/0058701 A1 | 3/2006 | Bolles et al. |
| 2006/0063980 A1 | 3/2006 | Hwang et al. |
| 2006/0063981 A1 | 3/2006 | Sotos et al. |
| 2006/0063982 A1 | 3/2006 | Sullivan et al. |
| 2006/0064298 A1 | 3/2006 | Lee |
| 2006/0064396 A1 | 3/2006 | Wei et al. |
| 2006/0066449 A1 | 3/2006 | Johnson |
| 2006/0067289 A1 | 3/2006 | Lee et al. |
| 2006/0067361 A1 | 3/2006 | Lee et al. |
| 2006/0068764 A1 | 3/2006 | Lim |
| 2006/0068856 A1 | 3/2006 | Zhu et al. |
| 2006/0071797 A1 | 4/2006 | Rosenfeld et al. |
| 2006/0073819 A1 | 4/2006 | Lowles |
| 2006/0073848 A1 | 4/2006 | Kwon |
| 2006/0074334 A1 | 4/2006 | Coyle |
| 2006/0077165 A1 | 4/2006 | Jang |
| 2006/0078139 A1 | 4/2006 | Meier et al. |
| 2006/0079294 A1 | 4/2006 | Chen |
| 2006/0079739 A1 | 4/2006 | Chen Wang et al. |
| 2006/0084465 A1 | 4/2006 | Kim |
| 2006/0085757 A1 | 4/2006 | Andre et al. |
| 2006/0089541 A1 | 4/2006 | Braun et al. |
| 2006/0089542 A1 | 4/2006 | Sands |
| 2006/0089560 A1 | 4/2006 | Kuo et al. |
| 2006/0089968 A1 | 4/2006 | Park et al. |
| 2006/0092908 A1 | 5/2006 | Sung et al. |
| 2006/0094442 A1 | 5/2006 | Kirkup et al. |
| 2006/0094452 A1 | 5/2006 | Kang |
| 2006/0094453 A1 | 5/2006 | Rhyu |
| 2006/0094454 A1 | 5/2006 | Kim |
| 2006/0094478 A1 | 5/2006 | Kim et al. |
| 2006/0094935 A1 | 5/2006 | Sussman et al. |
| 2006/0094936 A1 | 5/2006 | Russ |
| 2006/0094981 A1 | 5/2006 | Camp |
| 2006/0095848 A1 | 5/2006 | Naik |
| 2006/0097991 A1 | 5/2006 | Hotelling et al. |
| 2006/0098119 A1 | 5/2006 | Lee |
| 2006/0098825 A1 | 5/2006 | Katz |
| 2006/0099969 A1 | 5/2006 | Staton et al. |
| 2006/0100910 A1 | 5/2006 | Brown |
| 2006/0100978 A1 | 5/2006 | Heller et al. |
| 2006/0104644 A1 | 5/2006 | Kang |
| 2006/0105704 A1 | 5/2006 | Kimg |
| 2006/0106291 A1 | 5/2006 | Sidelnik et al. |
| 2006/0109340 A1 | 5/2006 | Kang |
| 2006/0111127 A1 | 5/2006 | Jang |
| 2006/0111436 A1 | 6/2006 | Kang et al. |
| 2006/0116134 A1 | 6/2006 | Shin |
| 2006/0116904 A1 | 6/2006 | Brem |
| 2006/0116908 A1 | 6/2006 | Dew et al. |
| 2006/0121935 A1 | 6/2006 | Dalsgaard et al. |
| 2006/0121937 A1 | 6/2006 | Son |
| 2006/0122466 A1 | 6/2006 | Nguyen-Dobinsky et al. |
| 2006/0122469 A1 | 6/2006 | Martel |
| 2006/0122474 A1 | 6/2006 | Teller et al. |
| 2006/0122542 A1 | 6/2006 | Smith et al. |
| 2006/0122870 A1 | 6/2006 | Austin et al. |
| 2006/0129067 A1 | 6/2006 | Grajales et al. |
| 2006/0132235 A1 | 6/2006 | Ozawa |
| 2006/0132844 A1 | 6/2006 | Kato et al. |
| 2006/0135123 A1 | 6/2006 | Jo |
| 2006/0135141 A1 | 6/2006 | Wilson et al. |
| 2006/0135855 A1 | 6/2006 | Alsafadi et al. |
| 2006/0135856 A1 | 6/2006 | Breuer et al. |
| 2006/0135857 A1 | 6/2006 | Ho et al. |
| 2006/0135858 A1 | 6/2006 | Nidd et al. |
| 2006/0135859 A1 | 6/2006 | Iliff |
| 2006/0135876 A1 | 6/2006 | Andresen et al. |
| 2006/0139315 A1 | 6/2006 | Kim |
| 2006/0140148 A1 | 6/2006 | Kwak et al. |
| 2006/0140428 A1 | 6/2006 | Qi et al. |
| 2006/0142069 A1 | 6/2006 | Choi |
| 2006/0142647 A1 | 6/2006 | Oosawa |

(56) References Cited

U.S. PATENT DOCUMENTS

| | | |
|---|---|---|
| 2006/0142648 A1 | 6/2006 | Banet et al. |
| 2006/0143043 A1 | 6/2006 | McCallie et al. |
| 2006/0146366 A1 | 7/2006 | Jang |
| 2006/0148469 A1 | 7/2006 | Kim |
| 2006/0148491 A1 | 7/2006 | Hyun et al. |
| 2006/0148499 A1 | 7/2006 | Chie |
| 2006/0148517 A1 | 7/2006 | Yu |
| 2006/0149139 A1 | 7/2006 | Bonmassar et al. |
| 2006/0149140 A1 | 7/2006 | Eldridge |
| 2006/0149591 A1 | 7/2006 | Hanf et al. |
| 2006/0149597 A1 | 7/2006 | Powell et al. |
| 2006/0152373 A1 | 7/2006 | King |
| 2006/0153396 A1 | 7/2006 | John |
| 2006/0154635 A1 | 7/2006 | Chan et al. |
| 2006/0155173 A1 | 7/2006 | Anttila et al. |
| 2006/0155205 A1 | 7/2006 | Sotos et al. |
| 2006/0155580 A1 | 7/2006 | Kawamura |
| 2006/0155814 A1 | 7/2006 | Bennett et al. |
| 2006/0156218 A1 | 7/2006 | Lee |
| 2006/0156239 A1 | 7/2006 | Jobs et al. |
| 2006/0160488 A1 | 7/2006 | Sueoka et al. |
| 2006/0160507 A1 | 7/2006 | Forrester |
| 2006/0161053 A1 | 7/2006 | Heikkila |
| 2006/0161064 A1 | 7/2006 | Watrous |
| 2006/0161459 A9 | 7/2006 | Rosenfeld et al. |
| 2006/0161778 A1 | 7/2006 | Stirbu et al. |
| 2006/0163360 A1 | 7/2006 | Steusloff et al. |
| 2006/0167346 A1 | 7/2006 | Sarel |
| 2006/0167367 A1 | 7/2006 | Stanczak et al. |
| 2006/0167529 A1 | 7/2006 | Schecter |
| 2006/0169529 A1 | 8/2006 | Tamakoshi |
| 2006/0172706 A1 | 8/2006 | Griffin et al. |
| 2006/0172737 A1 | 8/2006 | Hind et al. |
| 2006/0172785 A1 | 8/2006 | Phillips et al. |
| 2006/0172860 A1 | 8/2006 | Estrella |
| 2006/0173246 A1 | 8/2006 | Zaleski |
| 2006/0173708 A1 | 8/2006 | Vining et al. |
| 2006/0173712 A1 | 8/2006 | Joubert |
| 2006/0174017 A1 | 8/2006 | Robertson |
| 2006/0178567 A1 | 8/2006 | Goh et al. |
| 2006/0178617 A1 | 8/2006 | Adams et al. |
| 2006/0182051 A1 | 8/2006 | Lee et al. |
| 2006/0182091 A1 | 8/2006 | Park et al. |
| 2006/0183477 A1 | 8/2006 | Becking et al. |
| 2006/0183980 A1 | 8/2006 | Yang |
| 2006/0189299 A1 | 8/2006 | Rybak et al. |
| 2006/0189354 A1 | 8/2006 | Lee et al. |
| 2006/0192667 A1 | 8/2006 | Al-Aii |
| 2006/0193351 A1 | 8/2006 | Kim et al. |
| 2006/0195341 A1 | 8/2006 | Haaksma et al. |
| 2006/0195517 A1 | 8/2006 | Kaplan et al. |
| 2006/0197750 A1 | 9/2006 | Kerr et al. |
| 2006/0197753 A1 | 9/2006 | Hotelling |
| 2006/0198350 A1 | 9/2006 | Kim |
| 2006/0198533 A1 | 9/2006 | Wang et al. |
| 2006/0199547 A1 | 9/2006 | Song |
| 2006/0199618 A1 | 9/2006 | Steer et al. |
| 2006/0200354 A1 | 9/2006 | Ito et al. |
| 2006/0202816 A1 | 9/2006 | Crump et al. |
| 2006/0206011 A1 | 9/2006 | Higgins et al. |
| 2006/0206032 A1 | 9/2006 | Miele et al. |
| 2006/0209870 A1 | 9/2006 | Lee et al. |
| 2006/0214734 A1 | 9/2006 | Kim et al. |
| 2006/0217159 A1 | 9/2006 | Watson |
| 2006/0217599 A1 | 9/2006 | Ohta et al. |
| 2006/0221902 A1 | 10/2006 | Chen et al. |
| 2006/0221924 A1 | 10/2006 | Yang et al. |
| 2006/0223544 A1 | 10/2006 | Lee et al. |
| 2006/0223570 A1 | 10/2006 | Zhu et al. |
| 2006/0224051 A1 | 10/2006 | Teller et al. |
| 2006/0224413 A1 | 10/2006 | Kim et al. |
| 2006/0227979 A1 | 10/2006 | Chen |
| 2006/0229095 A1 | 10/2006 | Sung et al. |
| 2006/0229503 A1 | 10/2006 | Fluegel |
| 2006/0229506 A1 | 10/2006 | Castellanos |
| 2006/0229911 A1 | 10/2006 | Gropper et al. |
| 2006/0235281 A1 | 10/2006 | Tuccillo |
| 2006/0235864 A1 | 10/2006 | Hotelling et al. |
| 2006/0235926 A1 | 10/2006 | Naruse |
| 2006/0236041 A1 | 10/2006 | Sohn et al. |
| 2006/0236266 A1 | 10/2006 | Majava |
| 2006/0238517 A1 | 10/2006 | King et al. |
| 2006/0239215 A1 | 10/2006 | Munje |
| 2006/0239464 A1 | 10/2006 | Lee et al. |
| 2006/0241975 A1 | 10/2006 | Brown |
| 2006/0242114 A1 | 10/2006 | Arrouye et al. |
| 2006/0242293 A1 | 10/2006 | Russ |
| 2006/0245452 A1 | 11/2006 | Frederiksen et al. |
| 2006/0245597 A1 | 11/2006 | Guion-Johnson et al. |
| 2006/0246920 A1 | 11/2006 | Shim |
| 2006/0247504 A1 | 11/2006 | Tice |
| 2006/0247505 A1 | 11/2006 | Siddiqui |
| 2006/0247550 A1 | 11/2006 | Thiagarajan et al. |
| 2006/0250377 A1 | 11/2006 | Zadesky et al. |
| 2006/0251269 A1 | 11/2006 | Bauer |
| 2006/0252371 A1 | 11/2006 | Yanagida |
| 2006/0252998 A1 | 11/2006 | Kimbrell |
| 2006/0252999 A1 | 11/2006 | Devaul et al. |
| 2006/0253000 A1 | 11/2006 | Ciervo |
| 2006/0258391 A1 | 11/2006 | Lee |
| 2006/0258952 A1 | 11/2006 | Stahmann et al. |
| 2006/0259328 A1 | 11/2006 | Burd et al. |
| 2006/0259618 A1 | 11/2006 | Choi |
| 2006/0264197 A1 | 11/2006 | Mahini et al. |
| 2006/0265249 A1 | 11/2006 | Follis et al. |
| 2006/0268528 A1 | 11/2006 | Zadesky et al. |
| 2006/0268763 A1 | 11/2006 | George |
| 2006/0269106 A1 | 11/2006 | Staring et al. |
| 2006/0274038 A1 | 12/2006 | Redkov et al. |
| 2006/0274039 A1 | 12/2006 | Kim et al. |
| 2006/0274087 A1 | 12/2006 | Kim et al. |
| 2006/0276126 A1 | 12/2006 | Kim et al. |
| 2006/0277070 A1 | 12/2006 | Hungerford et al. |
| 2006/0279254 A1 | 12/2006 | Infanti |
| 2006/0281404 A1 | 12/2006 | Lee et al. |
| 2006/0281485 A1 | 12/2006 | Johnson et al. |
| 2006/0281495 A1 | 12/2006 | Yang |
| 2006/0281975 A1* | 12/2006 | Yang ............... A61B 5/0002 600/300 |
| 2006/0282791 A1 | 12/2006 | Bogomolov et al. |
| 2006/0284732 A1 | 12/2006 | Brock-Fisher |
| 2006/0285696 A1 | 12/2006 | Houtsma |
| 2006/0287586 A1 | 12/2006 | Murphy |
| 2006/0287606 A1 | 12/2006 | Hong et al. |
| 2006/0288053 A1 | 12/2006 | Holt et al. |
| 2006/0288091 A1 | 12/2006 | Oh et al. |
| 2006/0293056 A1 | 12/2006 | Kim et al. |
| 2006/0293078 A1 | 12/2006 | Qi et al. |
| 2006/0293093 A1 | 12/2006 | Marcus |
| 2006/0293571 A1 | 12/2006 | Bao et al. |
| 2006/0293606 A1 | 12/2006 | Tomita |
| 2007/0003072 A1* | 1/2007 | Ward ............... A61B 7/00 381/71.1 |
| 2007/0004969 A1 | 1/2007 | Kong et al. |
| 2007/0004987 A1 | 1/2007 | Oury et al. |
| 2007/0006317 A1 | 1/2007 | Asami et al. |
| 2007/0010719 A1 | 1/2007 | Huster et al. |
| 2007/0010722 A1 | 1/2007 | Suzuki et al. |
| 2007/0010724 A1 | 1/2007 | Halliday |
| 2007/0011061 A1 | 1/2007 | East |
| 2007/0013671 A1 | 1/2007 | Zadesky et al. |
| 2007/0015973 A1 | 1/2007 | Nanikashvili |
| 2007/0016450 A1 | 1/2007 | Bhora et al. |
| 2007/0016682 A1 | 1/2007 | Hodgson |
| 2007/0018997 A1 | 1/2007 | Edwards |
| 2007/0019795 A1 | 1/2007 | Thomas |
| 2007/0021148 A1 | 1/2007 | Mahini |
| 2007/0021979 A1 | 1/2007 | Cosentino et al. |
| 2007/0022158 A1 | 1/2007 | Vasa et al. |
| 2007/0024397 A1 | 2/2007 | Otsuka et al. |
| 2007/0025692 A1 | 2/2007 | Choi |
| 2007/0026905 A1 | 2/2007 | Murray |
| 2007/0027367 A1 | 2/2007 | Oliver et al. |
| 2007/0027369 A1 | 2/2007 | Pagnacco et al. |

(56) References Cited

U.S. PATENT DOCUMENTS

| | | |
|---|---|---|
| 2007/0027721 A1 | 2/2007 | Hasan et al. |
| 2007/0027960 A1 | 2/2007 | De Leon |
| 2007/0028006 A1 | 2/2007 | Laefer et al. |
| 2007/0028271 A1 | 2/2007 | Ju et al. |
| 2007/0030124 A1 | 2/2007 | Lee |
| 2007/0030337 A1 | 2/2007 | Smith |
| 2007/0030712 A1 | 2/2007 | Earl et al. |
| 2007/0032225 A1 | 2/2007 | Konicek et al. |
| 2007/0032228 A1 | 2/2007 | Varanda |
| 2007/0032257 A1 | 2/2007 | Kim et al. |
| 2007/0032832 A1 | 2/2007 | Feher |
| 2007/0033414 A1 | 2/2007 | Dunko |
| 2007/0033617 A1 | 2/2007 | Bloebaum |
| 2007/0035524 A1 | 2/2007 | Hyatt |
| 2007/0036373 A1 | 2/2007 | Townsend et al. |
| 2007/0037625 A1 | 2/2007 | Edwards |
| 2007/0038136 A1 | 2/2007 | Gopinathan et al. |
| 2007/0038137 A1 | 2/2007 | Arand et al. |
| 2007/0038164 A1 | 2/2007 | Afshar |
| 2007/0038471 A1 | 2/2007 | Meisel et al. |
| 2007/0038941 A1 | 2/2007 | Wysocki et al. |
| 2007/0041348 A1 | 2/2007 | Kwun et al. |
| 2007/0043275 A1 | 2/2007 | Manheimer et al. |
| 2007/0043594 A1 | 2/2007 | Lavergne |
| 2007/0043867 A1 | 2/2007 | Shigeta |
| 2007/0044013 A1 | 2/2007 | Hyatt |
| 2007/0046255 A1 | 3/2007 | Kim |
| 2007/0046561 A1 | 3/2007 | Cheon et al. |
| 2007/0046646 A1 | 3/2007 | Kwon et al. |
| 2007/0046649 A1 | 3/2007 | Reiner |
| 2007/0047493 A1 | 3/2007 | Park et al. |
| 2007/0049208 A1 | 3/2007 | Kim et al. |
| 2007/0049233 A1 | 3/2007 | Wu et al. |
| 2007/0049256 A1 | 3/2007 | Wassingbo |
| 2007/0049261 A1 | 3/2007 | Joglekar |
| 2007/0049359 A1 | 3/2007 | Sung |
| 2007/0049838 A1 | 3/2007 | Sauerland |
| 2007/0050054 A1 | 3/2007 | Sambandam et al. |
| 2007/0052691 A1 | 3/2007 | Zadesky et al. |
| 2007/0053327 A1 | 3/2007 | Park |
| 2007/0055116 A1 | 3/2007 | Clark et al. |
| 2007/0055151 A1 | 3/2007 | Shertukde et al. |
| 2007/0055166 A1 | 3/2007 | Patil |
| 2007/0058818 A1 | 3/2007 | Yoshimine |
| 2007/0060054 A1 | 3/2007 | Romesburg |
| 2007/0061171 A1 | 3/2007 | Ash et al. |
| 2007/0061393 A1 | 3/2007 | Moore |
| 2007/0061448 A1 | 3/2007 | Takahashi et al. |
| 2007/0063038 A1 | 3/2007 | Silverbrook et al. |
| 2007/0064669 A1 | 3/2007 | Classen et al. |
| 2007/0064686 A1 | 3/2007 | Bae et al. |
| 2007/0065794 A1 | 3/2007 | Mangum |
| 2007/0067659 A1 | 3/2007 | Tevanian, Jr. |
| 2007/0069687 A1 | 3/2007 | Suzuki |
| 2007/0070184 A1 | 3/2007 | Kim et al. |
| 2007/0070954 A1 | 3/2007 | Kim et al. |
| 2007/0071073 A1 | 3/2007 | Wang |
| 2007/0071643 A1 | 3/2007 | Hall et al. |
| 2007/0073132 A1 | 3/2007 | Vosch |
| 2007/0073847 A1 | 3/2007 | Lee |
| 2007/0076626 A1 | 4/2007 | Wise et al. |
| 2007/0077901 A1 | 4/2007 | Jung |
| 2007/0077964 A1 | 4/2007 | Llanos et al. |
| 2007/0078543 A1 | 4/2007 | Wakefield |
| 2007/0079027 A1 | 4/2007 | Marriott et al. |
| 2007/0080823 A1 | 4/2007 | Fu et al. |
| 2007/0081075 A1 | 4/2007 | Canova et al. |
| 2007/0082692 A1 | 4/2007 | Tirkkonen et al. |
| 2007/0082708 A1 | 4/2007 | Griffin |
| 2007/0083088 A1 | 4/2007 | Dijkman |
| 2007/0083616 A1 | 4/2007 | Madden |
| 2007/0085759 A1 | 4/2007 | Lee et al. |
| 2007/0086405 A1 | 4/2007 | Wang |
| 2007/0087739 A1 | 4/2007 | Jung |
| 2007/0088806 A1 | 4/2007 | Marriott et al. |
| 2007/0091167 A1 | 4/2007 | Shiina et al. |
| 2007/0091785 A1 | 4/2007 | Lindoff et al. |
| 2007/0093237 A1 | 4/2007 | Bayne |
| 2007/0093239 A1 | 4/2007 | Camp |
| 2007/0093241 A1 | 4/2007 | Oh et al. |
| 2007/0093281 A1 | 4/2007 | Park et al. |
| 2007/0094045 A1 | 4/2007 | Cobbs et al. |
| 2007/0094490 A1 | 4/2007 | Lohr |
| 2007/0097074 A1 | 5/2007 | Irimajiri |
| 2007/0097901 A1 | 5/2007 | Tirkkonen et al. |
| 2007/0097914 A1 | 5/2007 | Grilli et al. |
| 2007/0098195 A1 | 5/2007 | Holmes |
| 2007/0099657 A1 | 5/2007 | Scott |
| 2007/0099662 A1 | 5/2007 | Gallagher |
| 2007/0099672 A1 | 5/2007 | Oh |
| 2007/0100213 A1 | 5/2007 | Dossas et al. |
| 2007/0100653 A1 | 5/2007 | Ramer et al. |
| 2007/0106172 A1 | 5/2007 | Abreu |
| 2007/0106179 A1 | 5/2007 | Bagha et al. |
| 2007/0106180 A1 | 5/2007 | Peretto et al. |
| 2007/0106740 A1 | 5/2007 | Yach et al. |
| 2007/0109117 A1 | 5/2007 | Heitzmann et al. |
| 2007/0110015 A1 | 5/2007 | Chakraborty et al. |
| 2007/0111726 A1 | 5/2007 | Lambert et al. |
| 2007/0112274 A1 | 5/2007 | Heitzmann et al. |
| 2007/0112277 A1 | 5/2007 | Fischer et al. |
| 2007/0112891 A1 | 5/2007 | Marriott et al. |
| 2007/0115343 A1 | 5/2007 | Lessing |
| 2007/0116094 A1 | 5/2007 | Parts et al. |
| 2007/0116205 A1 | 5/2007 | Miller |
| 2007/0118054 A1 | 5/2007 | Pinhas et al. |
| 2007/0118400 A1 | 5/2007 | Morita et al. |
| 2007/0118558 A1 | 5/2007 | Kahandaliyanage |
| 2007/0121614 A1 | 5/2007 | Sandell et al. |
| 2007/0121979 A1 | 5/2007 | Zhu et al. |
| 2007/0123204 A1 | 5/2007 | Inukai |
| 2007/0123298 A1 | 5/2007 | Zhu et al. |
| 2007/0123300 A1 | 5/2007 | Park et al. |
| 2007/0123323 A1 | 5/2007 | Zhu et al. |
| 2007/0123763 A1* | 5/2007 | Al-Ali ............. A61B 5/14552 600/344 |
| 2007/0126705 A1 | 6/2007 | Ko et al. |
| 2007/0127582 A1 | 6/2007 | Lee et al. |
| 2007/0127740 A1 | 6/2007 | Gustavsson |
| 2007/0129003 A1 | 6/2007 | Dunko |
| 2007/0129012 A1 | 6/2007 | Snow |
| 2007/0129828 A1 | 6/2007 | Lee et al. |
| 2007/0130389 A1 | 6/2007 | Petersson et al. |
| 2007/0130532 A1 | 6/2007 | Fuller et al. |
| 2007/0133579 A1 | 6/2007 | Kim |
| 2007/0135083 A1 | 6/2007 | Kim et al. |
| 2007/0137462 A1 | 6/2007 | Barros et al. |
| 2007/0140392 A1 | 6/2007 | Cha et al. |
| 2007/0142942 A1 | 6/2007 | Hyatt |
| 2007/0143785 A1 | 6/2007 | Sammarco |
| 2007/0146116 A1 | 6/2007 | Kimbrell |
| 2007/0152812 A1 | 7/2007 | Wong et al. |
| 2007/0152983 A1 | 7/2007 | McKillop et al. |
| 2007/0154023 A1 | 7/2007 | Tseng et al. |
| 2007/0154024 A1 | 7/2007 | Grasfield et al. |
| 2007/0155307 A1 | 7/2007 | Ng et al. |
| 2007/0156029 A1 | 7/2007 | Morris et al. |
| 2007/0156450 A1 | 7/2007 | Roehm et al. |
| 2007/0156626 A1 | 7/2007 | Roehm et al. |
| 2007/0161358 A1 | 7/2007 | Bogdan |
| 2007/0161402 A1 | 7/2007 | Ng et al. |
| 2007/0162080 A1 | 7/2007 | Brockway et al. |
| 2007/0165583 A1 | 7/2007 | Pecen |
| 2007/0165872 A1 | 7/2007 | Bridger et al. |
| 2007/0167691 A1 | 7/2007 | Causevic |
| 2007/0167855 A1 | 7/2007 | Shin et al. |
| 2007/0169115 A1 | 7/2007 | Ko et al. |
| 2007/0172045 A1 | 7/2007 | Nguyen et al. |
| 2007/0173224 A1 | 7/2007 | Buckley et al. |
| 2007/0173231 A1 | 7/2007 | Fadell |
| 2007/0173701 A1 | 7/2007 | Ai-Aii |
| 2007/0176826 A1* | 8/2007 | Daniele ............. G01S 5/0289 342/465 |
| 2007/0176931 A1 | 8/2007 | Tivig et al. |

(56) References Cited

U.S. PATENT DOCUMENTS

| | | |
|---|---|---|
| 2007/0177742 A1 | 8/2007 | Edgren et al. |
| 2007/0178933 A1 | 8/2007 | Nelson |
| 2007/0179347 A1 | 8/2007 | Tarassenko et al. |
| 2007/0180047 A1 | 8/2007 | Dong et al. |
| 2007/0191034 A1 | 8/2007 | Lee et al. |
| 2007/0191049 A1 | 8/2007 | Lee |
| 2007/0191687 A1 | 8/2007 | Justus |
| 2007/0191729 A1 | 8/2007 | Park et al. |
| 2007/0195062 A1 | 8/2007 | Guthrie |
| 2007/0195904 A1 | 8/2007 | Kemenczy et al. |
| 2007/0197878 A1 | 8/2007 | Shklarski |
| 2007/0198130 A1 | 8/2007 | Wang et al. |
| 2007/0204022 A1 | 8/2007 | Hsu et al. |
| 2007/0204237 A1 | 8/2007 | Guo et al. |
| 2007/0206829 A1 | 9/2007 | Weinans et al. |
| 2007/0208233 A1 | 9/2007 | Kovacs |
| 2007/0218958 A1 | 9/2007 | Emery et al. |
| 2007/0219059 A1 | 9/2007 | Schwartz et al. |
| 2007/0219823 A1 | 9/2007 | Warner |
| 2007/0225016 A1 | 9/2007 | Jendbro et al. |
| 2007/0229536 A1 | 10/2007 | Bylsma et al. |
| 2007/0232098 A1 | 10/2007 | Danner |
| 2007/0232866 A1 | 10/2007 | Nephin et al. |
| 2007/0233721 A1 | 10/2007 | Bazar |
| 2007/0234235 A1 | 10/2007 | Scott |
| 2007/0236466 A1 | 10/2007 | Hotelling et al. |
| 2007/0237252 A1 | 10/2007 | Li |
| 2007/0237348 A1 | 10/2007 | Phillips |
| 2007/0238446 A1 | 10/2007 | Kim et al. |
| 2007/0238484 A1 | 10/2007 | Liu |
| 2007/0239070 A1 | 10/2007 | Hwang |
| 2007/0240030 A1 | 10/2007 | Cronstrom |
| 2007/0242154 A1 | 10/2007 | Cope |
| 2007/0242809 A1 | 10/2007 | Mousseau et al. |
| 2007/0244968 A1 | 10/2007 | Andreasson |
| 2007/0249290 A1 | 10/2007 | Jorgensen et al. |
| 2007/0249365 A1 | 10/2007 | Jendbro |
| 2007/0250578 A1 | 10/2007 | Hardy et al. |
| 2007/0250583 A1 | 10/2007 | Hardy et al. |
| 2007/0254612 A1 | 11/2007 | Simmons et al. |
| 2007/0254626 A1 | 11/2007 | Ahlgren |
| 2007/0255115 A1 | 11/2007 | Anglin et al. |
| 2007/0255120 A1 | 11/2007 | Rosnov |
| 2007/0255122 A1 | 11/2007 | Vol et al. |
| 2007/0255588 A1 | 11/2007 | Hamilton |
| 2007/0255799 A1 | 11/2007 | Forbes |
| 2007/0256026 A1 | 11/2007 | Klassen et al. |
| 2007/0259654 A1 | 11/2007 | Oijer |
| 2007/0260126 A1 | 11/2007 | Haumann et al. |
| 2007/0260480 A1 | 11/2007 | Cederlund |
| 2007/0269060 A1 | 11/2007 | Chou |
| 2007/0270115 A1 | 11/2007 | Kravets |
| 2007/0270139 A1 | 11/2007 | Jendbro et al. |
| 2007/0270662 A1 | 11/2007 | Chen |
| 2007/0271569 A1 | 11/2007 | Ohlgren et al. |
| 2007/0273714 A1 | 11/2007 | Hodge et al. |
| 2007/0274531 A1 | 11/2007 | Camp |
| 2007/0275745 A1 | 11/2007 | Owen |
| 2007/0275770 A1 | 11/2007 | Hyatt |
| 2007/0276632 A1 | 11/2007 | Banet et al. |
| 2007/0277107 A1 | 11/2007 | Almas |
| 2007/0279394 A1 | 12/2007 | Lampell et al. |
| 2007/0280175 A1 | 12/2007 | Cheng et al. |
| 2007/0281667 A1 | 12/2007 | Minor |
| 2007/0281731 A1 | 12/2007 | Attride et al. |
| 2007/0281744 A1 | 12/2007 | Andreasson |
| 2007/0282173 A1 | 12/2007 | Wang et al. |
| 2007/0282208 A1 | 12/2007 | Jacobs et al. |
| 2007/0282212 A1 | 12/2007 | Sierra et al. |
| 2007/0282905 A1 | 12/2007 | Karlberg |
| 2007/0283044 A1 | 12/2007 | Van Belle et al. |
| 2007/0283799 A1 | 12/2007 | Carruthers et al. |
| 2007/0285234 A1 | 12/2007 | Hovmalm et al. |
| 2007/0287391 A1 | 12/2007 | Hofer et al. |
| 2007/0287891 A1 | 12/2007 | Horn |
| 2007/0287892 A1 | 12/2007 | Estrella |
| 2007/0288499 A1 | 12/2007 | Dunko |
| 2007/0288898 A1 | 12/2007 | Isberg |
| 2007/0291709 A1 | 12/2007 | Wassingbo et al. |
| 2007/0291710 A1 | 12/2007 | Fadell |
| 2007/0293193 A1 | 12/2007 | Ramsten et al. |
| 2007/0296805 A1 | 12/2007 | Tedenvall et al. |
| 2007/0296820 A1 | 12/2007 | Lonn |
| 2007/0297355 A1 | 12/2007 | Jendbro et al. |
| 2007/0297357 A1 | 12/2007 | Todd et al. |
| 2007/0297625 A1 | 12/2007 | Hjort et al. |
| 2007/0299316 A1 | 12/2007 | Haslehurst et al. |
| 2007/0299318 A1 | 12/2007 | Chen et al. |
| 2007/0300063 A1 | 12/2007 | Adams et al. |
| 2007/0300267 A1 | 12/2007 | Griffin |
| 2008/0002605 A1 | 1/2008 | Todd et al. |
| 2008/0004499 A1 | 1/2008 | Davis |
| 2008/0004899 A1 | 1/2008 | Braxton |
| 2008/0004904 A1 | 1/2008 | Tran |
| 2008/0007533 A1 | 1/2008 | Hotelling et al. |
| 2008/0008127 A1 | 1/2008 | Choi et al. |
| 2008/0009681 A1 | 1/2008 | Al Hussiny |
| 2008/0012774 A1 | 1/2008 | Wang |
| 2008/0013747 A1 | 1/2008 | Tran |
| 2008/0018435 A1 | 1/2008 | Brown |
| 2008/0018454 A1 | 1/2008 | Chan et al. |
| 2008/0019305 A1 | 1/2008 | Dekorsy et al. |
| 2008/0021287 A1 | 1/2008 | Woellenstein et al. |
| 2008/0021288 A1 | 1/2008 | Bowman et al. |
| 2008/0021739 A1 | 1/2008 | Brock |
| 2008/0025254 A1 | 1/2008 | Love et al. |
| 2008/0027288 A1 | 1/2008 | Renz |
| 2008/0027752 A1 | 1/2008 | Phan et al. |
| 2008/0033252 A1 | 2/2008 | Estrella |
| 2008/0039699 A1 | 2/2008 | Neumann |
| 2008/0040087 A1 | 2/2008 | Watrous |
| 2008/0045805 A1 | 2/2008 | Sarel et al. |
| 2008/0049653 A1 | 2/2008 | Demirhan et al. |
| 2008/0049690 A1 | 2/2008 | Kuchibhotla et al. |
| 2008/0051667 A1 | 2/2008 | Goldreich |
| 2008/0057890 A1 | 3/2008 | McKillop et al. |
| 2008/0058607 A1 | 3/2008 | Watrous |
| 2008/0059197 A1 | 3/2008 | Jones et al. |
| 2008/0065412 A1 | 3/2008 | Vallone |
| 2008/0065419 A1 | 3/2008 | Esseiva et al. |
| 2008/0065691 A1 | 3/2008 | Suitts et al. |
| 2008/0066016 A1 | 3/2008 | Dowdy et al. |
| 2008/0066099 A1 | 3/2008 | Brodersen et al. |
| 2008/0066100 A1 | 3/2008 | Brodersen et al. |
| 2008/0071543 A1 | 3/2008 | Jarvis et al. |
| 2008/0077026 A1 | 3/2008 | Banet et al. |
| 2008/0077431 A1 | 3/2008 | Calder et al. |
| 2008/0077434 A1 | 3/2008 | Man et al. |
| 2008/0080424 A1 | 4/2008 | Torsner et al. |
| 2008/0082017 A1 | 4/2008 | Savic |
| 2008/0089287 A1 | 4/2008 | Sagfors et al. |
| 2008/0093157 A1 | 4/2008 | Drummond et al. |
| 2008/0101589 A1 | 5/2008 | Horowitz et al. |
| 2008/0103368 A1 | 5/2008 | Craine et al. |
| 2008/0103399 A1 | 5/2008 | Patangay et al. |
| 2008/0103406 A1 | 5/2008 | Kameli |
| 2008/0104547 A1 | 5/2008 | Morita et al. |
| 2008/0107121 A1 | 5/2008 | Young et al. |
| 2008/0108880 A1 | 5/2008 | Young et al. |
| 2008/0113614 A1 | 5/2008 | Rosenblatt |
| 2008/0114213 A1 | 5/2008 | Bagan |
| 2008/0114221 A1 | 5/2008 | Tso |
| 2008/0114266 A1 | 5/2008 | Shen et al. |
| 2008/0114615 A1 | 5/2008 | Mahesh et al. |
| 2008/0137876 A1 | 6/2008 | Kassal et al. |
| 2008/0137877 A1 | 6/2008 | Hubbard et al. |
| 2008/0139889 A1 | 6/2008 | Bagan |
| 2008/0139890 A1 | 6/2008 | Craine et al. |
| 2008/0139891 A1 | 6/2008 | Whitehead et al. |
| 2008/0146276 A1 | 6/2008 | Lee |
| 2008/0146887 A1 | 6/2008 | Rao et al. |
| 2008/0171915 A1 | 7/2008 | Kawajiri et al. |
| 2008/0214903 A1* | 9/2008 | Orbach .............. G16H 10/65 600/301 |

(56) References Cited

U.S. PATENT DOCUMENTS

| | | | |
|---|---|---|---|
| 2008/0228084 A1 | 9/2008 | Bedard et al. | |
| 2008/0249377 A1 | 10/2008 | Molducci et al. | |
| 2008/0262320 A1 | 10/2008 | Schaefer et al. | |
| 2008/0262389 A1 | 10/2008 | Shahar et al. | |
| 2008/0273709 A1 | 11/2008 | Thiagarajan et al. | |
| 2008/0281220 A1* | 11/2008 | Sharifpour | A61B 5/0002 600/538 |
| 2008/0287749 A1 | 11/2008 | Reuter | |
| 2008/0306355 A1 | 12/2008 | Walker | |
| 2008/0306367 A1 | 12/2008 | Koehler et al. | |
| 2009/0012430 A1 | 1/2009 | Lovoi et al. | |
| 2009/0062675 A1 | 3/2009 | Weigand et al. | |
| 2009/0105554 A1 | 4/2009 | Stahmann et al. | |
| 2009/0105605 A1 | 4/2009 | Abreu | |
| 2009/0149699 A1* | 6/2009 | Ullmann | A61M 21/00 600/28 |
| 2009/0175478 A1 | 7/2009 | Nakajima et al. | |
| 2009/0227888 A1 | 9/2009 | Salmi et al. | |
| 2009/0292219 A1 | 11/2009 | Pringle et al. | |
| 2010/0010378 A1 | 1/2010 | Hatlestad et al. | |
| 2010/0145210 A1 | 6/2010 | Graff et al. | |
| 2010/0217136 A1 | 8/2010 | Turner et al. | |
| 2010/0232615 A1 | 9/2010 | Sorlander et al. | |
| 2010/0274099 A1* | 10/2010 | Telfort | A61B 5/6843 600/300 |
| 2011/0087115 A1 | 4/2011 | Sackner et al. | |
| 2011/0092254 A1 | 4/2011 | Bestle et al. | |
| 2011/0098588 A1 | 4/2011 | Siejko et al. | |
| 2011/0125061 A1 | 5/2011 | Shahar et al. | |

FOREIGN PATENT DOCUMENTS

| | | |
|---|---|---|
| CA | 2260718 | 8/1999 |
| CA | 2375359 | 10/2001 |
| CA | 2653447 | 6/2007 |
| CN | 1443514 A | 9/2003 |
| CN | 2623173 Y | 7/2004 |
| EP | 1151719 | 11/2001 |
| EP | 1279370 | 1/2003 |
| EP | 1484018 | 12/2004 |
| EP | 1617361 | 1/2006 |
| EP | 1638010 | 3/2006 |
| EP | 1810618 | 7/2007 |
| GB | 2369434 | 5/2002 |
| GB | 2410148 A | 7/2005 |
| GB | 2419946 | 10/2006 |
| GB | 2426586 A | 11/2006 |
| JP | 2003-180681 | 7/2003 |
| JP | 2004-81250 | 3/2004 |
| JP | 2005-296643 | 10/2005 |
| KR | 2002-0062904 | 7/2002 |
| KR | 2003-0018702 | 3/2003 |
| KR | 2003-0045741 | 6/2003 |
| KR | 20-0323815 | 8/2003 |
| KR | 10-2004-0042273 | 5/2004 |
| KR | 10-2004-0052310 | 6/2004 |
| KR | 20-0371531 | 1/2005 |
| KR | 20-0378990 | 3/2005 |
| KR | 20-0383411 | 4/2005 |
| KR | 10-2005-0111263 | 11/2005 |
| KR | 10-2006-0006118 | 1/2006 |
| KR | 10-2006-0025301 | 3/2006 |
| KR | 10-2006-0044054 | 5/2006 |
| TW | I251483 | 3/2006 |
| WO | 1989006932 | 8/1989 |
| WO | 1994013206 | 6/1994 |
| WO | 1996013212 | 5/1996 |
| WO | 1996024287 | 8/1996 |
| WO | 1996029009 | 9/1996 |
| WO | 1997000045 | 1/1997 |
| WO | 1997003600 | 2/1997 |
| WO | 1997016116 | 5/1997 |
| WO | 1997019640 | 6/1997 |
| WO | 1998034542 | 8/1998 |
| WO | 1999001859 | 1/1999 |
| WO | 99/14882 | 3/1999 |
| WO | 1999038431 | 5/1999 |
| WO | WO/1999/038431 | 8/1999 |
| WO | 1999052435 | 10/1999 |
| WO | 1999052436 | 10/1999 |
| WO | 1999060919 | 12/1999 |
| WO | 2000002486 | 1/2000 |
| WO | WO/2000/044279 | 8/2000 |
| WO | WO/2001/008560 | 2/2001 |
| WO | WO/2001/022883 | 4/2001 |
| WO | 01/30231 | 5/2001 |
| WO | 2001/034033 | 5/2001 |
| WO | WO/01/39089 | 5/2001 |
| WO | WO/2001/033457 | 5/2001 |
| WO | 0162152 | 8/2001 |
| WO | 0178059 | 10/2001 |
| WO | WO/2001/072228 | 10/2001 |
| WO | 01/87143 | 11/2001 |
| WO | WO/01/89368 | 11/2001 |
| WO | WO/2001/082789 | 11/2001 |
| WO | WO/2001/082797 | 11/2001 |
| WO | 02/000117 | 1/2002 |
| WO | 2002009586 | 2/2002 |
| WO | 2002024074 | 3/2002 |
| WO | 2002/030277 | 4/2002 |
| WO | 2002032313 | 4/2002 |
| WO | 2002/049509 | 6/2002 |
| WO | 2002/073829 | 9/2002 |
| WO | 2002069804 | 9/2002 |
| WO | WO/2002/071947 | 9/2002 |
| WO | 2002/096293 | 12/2002 |
| WO | 2003/005891 | 1/2003 |
| WO | 2003/013341 | 2/2003 |
| WO | 2003028555 | 4/2003 |
| WO | 2003/057037 | 7/2003 |
| WO | 2003063707 | 7/2003 |
| WO | WO/2003/055395 | 7/2003 |
| WO | 2003/063707 | 8/2003 |
| WO | 2003/063708 | 8/2003 |
| WO | 2003077511 | 9/2003 |
| WO | 03/088841 | 10/2003 |
| WO | 03088838 | 10/2003 |
| WO | 2003096262 | 11/2003 |
| WO | 2004000111 | 12/2003 |
| WO | WO/2003/105657 | 12/2003 |
| WO | WO/2004/002317 | 1/2004 |
| WO | 2004/026126 | 4/2004 |
| WO | WO/2004/032741 | 4/2004 |
| WO | WO/2004/032742 | 4/2004 |
| WO | 2004/037083 | 5/2004 |
| WO | 2004/037084 | 5/2004 |
| WO | 2004/056268 | 7/2004 |
| WO | 2004/061744 | 7/2004 |
| WO | 2004058054 | 7/2004 |
| WO | WO/2004/060483 | 7/2004 |
| WO | WO/2004/004411 | 8/2004 |
| WO | 2004078038 | 9/2004 |
| WO | 2004/098390 | 11/2004 |
| WO | 2004/103150 | 12/2004 |
| WO | 2004/109537 | 12/2004 |
| WO | 2004105612 | 12/2004 |
| WO | 2005/000123 | 1/2005 |
| WO | WO/2005/002422 | 1/2005 |
| WO | 2005/011491 | 2/2005 |
| WO | 2005013797 | 2/2005 |
| WO | 2005013819 | 2/2005 |
| WO | 2005016129 | 2/2005 |
| WO | 2005/027720 | 3/2005 |
| WO | WO/2005/020841 | 3/2005 |
| WO | 2005046448 | 5/2005 |
| WO | WO/2005/046448 | 5/2005 |
| WO | WO/2005/046467 | 5/2005 |
| WO | 2005055287 | 6/2005 |
| WO | 2005/084534 | 9/2005 |
| WO | 2005096205 | 10/2005 |
| WO | 2005/107586 | 11/2005 |
| WO | 2005116903 | 12/2005 |
| WO | 2006013647 | 2/2006 |

(56) References Cited

FOREIGN PATENT DOCUMENTS

| | | |
|---|---|---|
| WO | 2006029322 | 3/2006 |
| WO | 2006/037331 | 4/2006 |
| WO | 2006/055037 | 5/2006 |
| WO | 2006/078954 | 7/2006 |
| WO | 2006079062 | 7/2006 |
| WO | 2006/087345 | 8/2006 |
| WO | 2006/091564 | 8/2006 |
| WO | 2006090964 | 8/2006 |
| WO | 2006101375 | 9/2006 |
| WO | 2006110969 | 10/2006 |
| WO | 2006/116718 A2 | 11/2006 |
| WO | 2006113968 | 11/2006 |
| WO | 2006116718 | 11/2006 |
| WO | 2006127022 | 11/2006 |
| WO | 2006128168 | 11/2006 |
| WO | WO/2006/119543 | 11/2006 |
| WO | 2007/019289 | 2/2007 |
| WO | 2007013711 | 2/2007 |
| WO | 2007043902 | 4/2007 |
| WO | WO/2007/047929 | 4/2007 |
| WO | WO/2007/054798 | 5/2007 |
| WO | WO/2007/060663 | 5/2007 |
| WO | 2007069961 | 6/2007 |
| WO | 2007/107908 | 9/2007 |
| WO | WO/2007/099314 | 9/2007 |
| WO | 2007127386 | 11/2007 |
| WO | WO/2007/134394 | 11/2007 |
| WO | 2007149279 | 12/2007 |
| WO | 2007149536 | 12/2007 |
| WO | 2008000254 | 1/2008 |
| WO | 2008000259 | 1/2008 |
| WO | 2008013561 | 1/2008 |
| WO | 2008021118 | 2/2008 |
| WO | 2008035211 | 3/2008 |
| WO | 2008036649 | 3/2008 |
| WO | WO/2008/041239 | 4/2008 |
| WO | WO/2008/063288 | 5/2008 |

OTHER PUBLICATIONS

Dell Axim X51/X51v Owner's Manual, Dell Inc., Mar. 2006, pp. 1-8, 37-122, 129-136.
VAIO User Guide Personal Computer VGN-AX500G Series, Sony Corporation, 2005, pp. 10-139, 237.
MacBook Pro User's Guide, 2006, Apple Computer Inc., Cupertino, United States, pp. 1-92, 115-123.
Dell Inspiron 6400/E1505, Dell Inc., Aug. 2006, pp. 1-75, 99-102, 155-160, 169-179.
Samsung NP-X20/X25/X50 User's Guide, Samsung, Sep. 20, 2005, pp. 1-95, 101-108, 155-169.
Zen Vision: M, Creative Technology Ltd., May 2006, pp. 1-33.
TG800 User Guide, LG Electronics Inc., 2006, pp. 1-145.
TM250 User Guide, LG Electronics Inc., 2003, pp. 1-125.
LX5550 Cellular Phone, LG Electronics Inc., 2004, pp. 1-143.
LG-4600 User Guide, LG Electronics Inc., 2003, pp. 1-117.
LG 490 User Guide, LG Electronics Inc., 2006, pp. 1-80.
LG 240 User Guide, LG Electronics Inc., 2006, pp. 1-93.
LG 500 User Guide, LG Electronics Inc., 2005, pp. 1-82.
LG 535, LG Electronics Inc., 2004, pp. 1-118.
L1150 User Guide, LG Electronics Inc., 2004, pp. 1-125.
LG 1400 User Guide, LG Electronics Inc., 2004, pp. 1-115.
LG 1500 User Guide, LG Electronics Inc., 2005, pp. 1-85.
LG 2000 User Guide, LG Electronics Inc., 2005, pp. 1-88.
LG 9100 User Guide, LG Electronics Inc., 2005, pp. 1-87.
Sprint PCS Vision Multimedia Phone MM-8300 by Sanyo, Sprint, 2005, pp. 1-316.
Sprint Power Vision Multimedia Phone MM-7500 by Sanyo, Sprint Nextel, 2005, pp. 1-334.
Sidekick Reference Guide, Danger Inc., 2003, pp. 1-59.
Sanyo Katana User Guide, Sanyo, 1996-2006, pp. 1-142.
Sanyo SCP-3100 User Guide, Sanyo, 1996-2006, pp. 1-148.
Ultracurve Pro DEQ2496 User's Manual, Behringer International, Bothell, WA, United States, Jul. 2003, pp. 1-23.
Edirol USB Audio Capture UA-25 Owner's Manual, Roland Corporation, Los Angeles, CA, United States, 2004, pp. 1-68.
Getting Started with DASYLab, National Instruments/CEC Capital Equipment, Bedford, NH, United States, Sep. 2005, pp. 1-56.
Tri Band Edge Series SGH-D606 Portable Digital Telephone User Manual, Samsung Electronics Co. Ltd., 2006, pp. 1-179.
Quad Band Edge Series SGH-D807 Portable Digital Telephone User Manual, Samsung Electronics Co. Ltd., 2006, pp. 1-185.
SGH-t609 Portable Quad-Band Telephone User Guide, Samsung Electronics Co. Ltd., Apr. 17, 2006, pp. 1-180.
SPH-a640 Series Portable Tri-Mode Telephone User Guide, Samsung Electronics Co. Ltd., 2006, pp. 1-150.
SPH-a740 Series Portable Tri-Mode Telephone User Guide, Samsung Electronics Co. Ltd., 2004-2005, pp. 1-141.
SPH-A920 User's Manual, Samsung Electronics Co. Ltd., Jun. 21, 2005, pp. 1-29.
SGH-A706 Series Portable Quad-Band Mobilephone User Guide, Samsung Electronics Co. Ltd., 2006, pp. 1-229.
SPH-A840 Series Portable Tri-Mode Telephone User Guide, Samsung Electronics Co. Ltd., 2005, pp. 1-137.
SCH-A950 Series Portable All Digital Telephone User Guide, Samsung Electronics Co. Ltd., 2006, pp. 1-145.
SPH-A460 Series Portable Tri-Mode Telephone User Guide, Samsung Electronics Co. Ltd., 2002, pp. 1-102.
SGH-d407 Series Portable Quad-Band Mobile Phone User Guide, Samsung Electronics Co. Ltd., 2006, pp. 1-146.
SCH-A870 Series Portable Tri-Mode Telephone User's Guide, Samsung Electronics Co. Ltd., 2006, pp. 1-132.
Koi User Guide, Kyocera Wireless Corporation, 2004, pp. 1-65.
BlackBerry Wireless Handheld User Guide, Research In Motion Limited, Canada, May 13, 2003, pp. 1-297.
BlackBerry Wireless Handheld User Guide, Research In Motion Limited, Canada, Feb. 4, 2003, pp. 1-309.
S55, Siemens, 2002, pp. 1-147.
Kraman, SS, et al., Design, Construction, and Evaluation of a Bioacoustic Transducer Testing System for Respiratory Sounds, IEEE Trans Biomed Eng., Aug. 2006, 53(8): pp. 1711-1715.
Tavel, ME, et al., The Cervical Bruit: Sound Spectral Analysis Related to Severity of Carotid Arterial Disease, Clin Cardiol., Oct. 2006, 29(10): pp. 462-465.
Ahlstrom, C., et al., Feature Extraction for Systolic Heart Murmur Classification, Ann Biomed Eng., Nov. 2006, 34(11): pp. 1666-1677.
Yadollahi, A., et al., Adaptive Compression of Respiratory and Swallowing Sounds, Conf Proc IEEE Eng Med Biol Soc., 2006, 1: pp. 517-520.
Rajan, S., et al., Unsupervised and Uncued Segmentation of the Fundamental Heart Sounds in Phonocardiograms Using A Time-Scale Rep., Conf Proc IEEE Eng Med Biol Soc., 2006, 1: pp. 3732-3735.
Kahya, YP, et al., Classifying Respiratory Sounds with Different Feature Sets, Conf Proc IEEE Eng Med Biol Soc., 2006, 1: pp. 2856-2859.
Belmont, JM, et al., Evaluation of Remote Stethoscopy for Pediatric Telecardiology, Telemed J., 1995, 1(2): pp. 133-149.
Kumar, D., et al., Detection of S1 and S2 Heart Sounds by High Frequency Signatures, Conf Proc IEEE Eng Med Biol Soc., 2006, 1: pp. 1410-1416.
Lightfoot, JT, et al., Ambient Noise Interferes with Auscultatory Blood Pressure Measurement During Exercise, Med Sci Sports Exerc., Apr. 1996, 28(4): pp. 502-508.
Charleston-Villalobos, S., et al., Heart Sounds Interference Cancellation in Lung Sounds, Conf Proc IEEE Eng Med Biol Soc., 2006, 1: pp. 1694-1697.
Taplidou, SA, et al., Nonlinear Characteristics of Wheezes as Seen in the Wavelet Higher-Order Spectra Domain, Conf IEEE Med Biol Soc., 2006, 1: pp. 4506-4509.
Taplidou, SA, et al., Nonlinear Analysis of Heart Murmurs Using Wavelet-Based Higher Order Spectral Parameters, Conf IEEE Med Biol Soc., 2006; 1: pp. 4502-4505.

(56) References Cited

OTHER PUBLICATIONS

Yimaz, CA, et al., Multi-Channel Classification of Respiratory Sounds, Conf IEEE Med Biol Soc., 2006, 1: pp. 2864-2867.
Cortes, S., et al., Detection and Adaptive Cancellation of Heart Sound Interference in Tracheal Sounds, Conf IEEE Med Biol Soc., 2006, 1: pp. 2860-2863.
Manecke, GR, et al., Computer-Assisted Auscultation of a Bronchopleuocutaneous Fistula During General Anesthesia, Anesth Analg., Oct. 1996, 83(4): pp. 880-882.
Tavel, ME, et al., Cardiac Auscultation: A Glorious Past—and it Does Have a Future! Circulation, Mar. 7, 2006, 113 (9): pp. 1255-1259.
Tavel, ME, et al., Usefulness of a New Sound Spectral Averaging Technique to Distinguish An Innocent Systolic Murmur From Aortic Stenosis, Am J Cardiol., Apr. 1, 2005, 95(7): pp. 902-904.
Herold, J., et al., Diagnosing Aortic Valve Stenosis by Correlation Analysis of Wavelet Filtered Heart Sounds, Med Biol Eng Comput., Jul. 2005, 43(4): pp. 451-456.
Mansy, HA, et al., Computerized Analysis of Auscultatory Sounds Associated with Vascular Patency of Haemodialysis Access, Med Biol Eng Comput, Jan. 2005, 43(1): pp. 56-62.
Hadjileontiadis, LJ, Wavelet-Based Enhancement of Lung and Bowel Sounds Using Fractional Dimension Thresholding-Part 1: Methodology, IEEE Trans Biomed Eng., Jun. 2005, 52(6): pp. 1143-1148.
Zekry, Ben S., et al., Initial Clinical Experience with a Hand-Held Device for the Detection of Bileaflet Prosthetic Valve Malfunction, J Heart Valve Dis., Jul. 2005, 14(4): pp. 1-16.
Fritzsche, D., et al., Digital Frequency Analysis of Valve Sound Phenomena in Patients after Prosthetic Valve Surgery, J Heart Valve Dis., Sep. 2005, 14(5): pp. 657-663.
Kaniusas, E., et al.. Acoustical Signal Properties for Cardiac/Respiratory Activity and Apneas, IEEE Trans Biomed Eng., Nov. 2005, 52(11): pp. 1812-1822.
Hadjileontiadis, LJ, et al., Adaptive Reduction of Heart Sounds from Lung Sounds Using Fourth-Order Statistics, IEEE Trans Biomed Eng., Jul. 1997, 44(7): pp. 642-648.
Hult, P., et al., Detection of the Third Heart Sound Using Tailored Wavelet Approach: Method Verification, Med Biol Eng Comput., Mar. 2005, 43(2): pp. 212-217.
Murphy, R., The Stethoscope-Obsolescence or Marriage, Respir Care, May 2005, 50(5): pp. 660-661.
Beaumont, CE, Choosing the Best Stethoscope, Nursing, Aug. 2005, 35(8 Suppl E D): pp. 27-28.
El-Segaier, M., et al., Computer-Based Detection and Analysis of Heart Sound and Murmur, Ann Biomed Eng., Jul. 2005, 33(7): pp. 937-942.
Kandaswamy, A., et al., Neural Classification of Lung Sounds Using Wavelet Coefficients, Comput Biol Med, Sep. 2004, 34(6): pp. 523-537.
Pasterkamp, H., et al., Assymmetry of Respiratory Sounds and Thoracic Transmission, Med Biol Eng Comput., Mar. 1997, 35(2): pp. 103-106.
Yeginer, M., et al., Using Lung Sounds in Classification of Pulmonary Diseases According to Respiratory Subphases, Conf Proc IEEE Eng Med Biol Soc., 2004, 1: pp. 482-485.
Kompis, M., et al., Acoustic Imaging of the Human Chest, Laboratory and Animal Investigations, Oct. 2001, pp. 1309-1321.
Zenk, BM, et al., Accuracy of Detecting Irregular Cardiac Rhythms Via Telemedicine, J Telemad Telecare, 2004, 10 (1): pp. 55-58.
Murphy, RL, et al., Automated Lung Sound Analysis in Patients with Pneumonia, Respir Care, Dec. 2004, 49 (12): pp. 1490-1497.
Manecke, GR, et al., Auscultation Revisited: The Waveform and Spectral Characteristics of Breath Sounds During General Anesthesia, Int. J. Clin. Monit. Comput, Nov. 1997, 14(4): pp. 231-240.
Rangayyan, RM, et al., Parametric Representation and Screening of Knee Joint Vibroarthrographic Signals, IEEE Trans Biomed Eng., Nov. 1997, 44(11): pp. 1068-1074.

Lazareck, LJ, et al., Classification of Normal and Dysphagic Swallows by Acoustical Means, IEEE Trans Biomed Eng., Dec. 2004, 51(12): pp. 2103-2112.
Pressler, GA, et al.. Detection of Respiratory Sounds at the External Ear, IEEE Trans Biomed Eng., Dec. 2004, 51(12): pp. 2089-2096.
Allen, J., et al., Characterization of the Korotkoff Sounds Using Joint Time-Frequency Analysis, Physiol Meas., Feb. 2004, 25(1): pp. 107-117.
Elphick, HE, et al., Validity and Reliability of Acoustic Analysis of Respiratory Sounds in Infants, Arch Dis Child., Nov. 2004, 89(11): pp. 1059-1063.
Hult, P., et al., Detection of the Third Heart Sound Using A Tailored Wavelet Approach, Med Biol Eng Comput, Mar. 2004, 42(2): pp. 253-258.
Oud, M., et al., Spirometry and Forced Oscillometry Assisted Optimal Frequency Band Det. for Computerized Analysis of Trach. Lung Sounds, Physiol Meas., Jun. 2004, 25(3): pp. 595-606.
Homs-Corbera, A., et al., Time-Frequency Detection and Analysis of Wheezes During Forced Exhalation, IEEE Trans Biomed Eng., Jan. 2004, 51(1): pp. 182-186.
Allen, A., From Early Wireless to Everest, Telemed Today, Apr.-May 1998, 6(2): pp. 16-18.
Okamoto, E., et al., Development of an Electro-Stethoscope System and Design of an Optimum Filter Based on Tissue Sound Transmission, Artif Organs, Feb. 2004, 28(2): pp. 226-237.
McKee, A., et al., Beam Shape, Focus Index, and Localization Error for Performance Evaluation of a Multisensor Stethoscope Beamformer, Conf Proc IEEE Eng Med Biol Soc., 2004, 3: pp. 2062-2065.
Fragasso, G., et al., Validation of Heart and Lung Teleauscultation on an Internet-Based System, Am J Cardiol., Nov. 1, 2003, 92(9): pp. 1138-1139.
Widmalm, SE, et al., The Dynamic Range of TMJ Sounds, J Oral Rehabil., May 2003, 30(5): pp. 495-500.
Oud, M., et al., Lung Function Interpolation by Means of Neural-Network Supported Analysis of Respiration Sounds, Med Eng Phys., May 2003, 25(4): pp. 309-316.
Charleston, S., et al., Interference Cancellation in Respiratory Sounds Via a Multiresolution Joint Time-Frequency Delay, IEEE Trans Biomed Eng., Oct. 1997, 44(10): pp. 1006-1019.
Nokia 9500 Communicator User Guide, Nokia Corporation, 2004-2005, pp. 1-108.
Sony Ericsson P800 User's Guide, first edition, Sony Ericsson Mobile Communications, Nov. 2002, pp. 1-195.
PDT 8100 Series Product Reference Guide for Pocket PC 2002, Symbol Technologies Inc., Holtsville, New York, United States, Dec. 2002, pp. 1-321.
BlackBerry Wireless Handheld Software Version 2.6 Installation and Getting Started Guide, Research In Motion Limited, Waterloo, Ontario, Canada, Dec. 2002, pp. 1-321.
BlackBerry Handheld Installation and User's Guide, Research In Motion Limited, Waterloo, Ontario, Canada, 1999-2000, pp. 1-99.
IPod User's Guide, Apple Computer Inc., Cupertino, California, United States, 2004, pp. 1-64.
IPod Classic Features Guide, Apple Computer Inc., Cupertino, California, United States, 2008, pp. 1-72.
Using Your Treo 650 Smartphone, Palm Inc., 2005, pp. 1-226.
Nokia 9210i Communicator User's Guide, Nokia Corporation, 2000-2003, pp. 1-290.
Nokia 9300 User Guide, Nokia Corporation, 2004-2005, pp. 1-103.
Nokia 9300i User Guide, Nokia Corporation, 2005-2006, pp. 1-107.
3M Littmann, Electronic Stethoscope Model 4100 WS with Ambient Noise Reduction, 2005, U.S., pp. 1-5.
Hahn, AW; On Stethoscope Design: A Challenge for Biomedical Circuit Designers, Biomed Sci Instrum., 2001; 37: 499-503.
Chien, JC, et al., A Study of Heart Sound and Lung Sound Separation by Independent Component Analysis Technique, Conf Proc IEEE Eng Med Biol Soc., 2006; 1: pp. 5708-5711.
Bhatikar, Sr, et al., A Novel Pardigm for Telemedicine Using the Personal Bio-monitor, Biomed Sci Instrum., 2002; 38: pp. 59-70.
Johanson, M., et al., A Remote Auscultation Tool for Advanced Home Health-care, J Telemed Telecare., 2002; 8 Suppl 2: pp. 45-47.
Brusco, M., et al., Digital Phonocardiography: A PDA-Based Approach, Conf Proc IEEE Med Biol Soc., 2004; 3: pp. 2299-2302.

(56) References Cited

OTHER PUBLICATIONS

Andrisevic, N., et al., Detection of Heart Murmurs Using Wavelet Analysis and Artificial Neural Networks, J Biomech Eng., Nov. 2005; 127(6): pp. 899-904.
Watrous, RL, et aL, Computer-Assisted Detection of Systolic Murmurs with Hypertrophic Cardiomyopathy: A Pilot Study, Tex Heart Inst J., 2004; 31(4): pp. 368-375.
Dembeyiotis, S., et al., A Novel Communications Network for the Provision of Medical Care in Disaster and Emergency Situations, Conf Proc IEEE Eng Med Biol Soc., 2004; 5: pp. 3380-3383.
Hult, P., et al., An Improved Bioacoustic Method for Monitoring of Respiration, Technol Health Care, 2004; 12(4): pp. 323-332.
Istrate, D., et al., Information Extraction From Sound for Medical Telemonitoring, Conf IEEE Med Biol Soc., Apr. 2006; 10(2): pp. 264-274.
Watrous, RL, Computer-aided Auscultation of the Heart from Anatomy and Physiology to Diagnostic Decision Support, Conf Proc IEEE Eng Med Biol Soc., 2006; 1: pp. 140-143.
Cerna, Michael, et al., The Fundamentals of FHT-Based Signal Analysis and Measurement, Application Note 041, National Instruments Corporation, Jul. 2000, pp. 1-20.
Canadian Intellectual Property Office Action, Application No. 2,656,699, Applicant: Sabatino, Michael, Nov. 1, 2013, pp. 1-4.
Thiagarajan, Arvind, et al., Systems and Methods for Analysis and Display of Heart Sounds, U.S. Appl. No. 60/833,385, United States, Jul. 25, 2006, pp. 1-37.
Bagha, Merat, et al., Medical Examination Apparatus, System, and Method, U.S. Appl. No. 60/728,568, United States, Oct. 20, 2005, pp. 1-27.
Smith, Steven W., The Scientist and Engineer's Guide to Digital Signal Processing, Second Edition, California Technical Publishing, San Diego, CA, United States, 1997-1999, pp. 509-514.
UA-25 USB Audio Capture Service Notes, Roland Corporation, Japan, Jul. 2004, pp. 1-10 and 12.
Microsoft Windows XP The User Experience Reviewers Guide, Microsoft Corporation, Redmond, WA, United States, Aug. 2001, pp. 1-61.
Eurorack UB 1202 Technical Specifications, Version 1.4, Behringer, Germany, Jan. 2004, pp. 1-5.
EMachines Series Generic User Guide, Acer Incorporated, United States, 2009, pp. 1-54.
Sabatino, Michael, et al., Advances Beyond the Stethoscope for Acquiring Data on the Function of the Human Respiratory System, Biomedical Problems of the 21st Century/1st Annual Binghamton Biomedical Research Conference, Binghamton, New York, United States, Mar. 25, 2006, p. 72.
Pasterkamp H., Kraman S., Wodicka G., "Advances Beyond the Stetoscope", American Journal of Respiratory and Criticla Care Medicine, 1997, vol. 156, pp. 974-987.
Malmberg L., Sorva R., Sovijarvi A., "Frequency Distribution of Breath Sounds as an Indicator of Bronchoconstriction", Pediatric Pulmonology, 1994, vol. 18.
Murphy RL., Holford SK., Knowler WC., "Visual Lung Sound characterization by Time Expanded Waveform Analysis", New England Journal of Medicine,, 1977, vol. 296, pp. 968-971.
Mussell MJ., Miyamoto Y., "Comparison of Normal Respiratory Sounds Recorded From Chest", Frontiers Med. Biol Engng, 1992, vol. 4, pp. 73-85.
Yap Y., Moussavi Z., "Acoustical Airflow Estimation From Tracheal Sound Power", Proc. IEEE CCECE, vol. 2, 2002, pp. 1073-1076.
Polat H., Guler I., "A Simple Computer Based Measurement and Analysis System of Pulmonary Auscultation Sounds", Journal of Medical Systems, 2004, vol. 28, pp. 665-672.
Golabbakhsh M., Moussavi Z., "Relationship Between Airflow and Frequency Based Features of Tracheal Respiratory Sound", IEEE CCECE, 2004, pp. 751-754.
Mousdavi Z., Leopando ZMT., Pasterkamp H., Rempel G., "Computerized Acoustical Respiratory Phase Detection Without Airflow", MedBioEngComputing, 2000, vol. 38 (2), pp. 198-203.

Schreur H., Sterk P., Vanderschoot, "Lung Sound Intensity in Patients With Emphysema and In Normal Subjects at Standardized Airflows", Thorax, 1992, vol. 47, pp. 674-679.
Pasterkamp H., Consunji-Araneta R., Oh Y., Holbrow J., "Chest Surface Mapping of Lung Sounds During Methacholine Challenge", Pediatric Pulmonology, 1997, vol. 23, pp. 21-30.
R.L. Watrous, D.M. Grove and D.L. Bowen, Methods and Results in Characterizing Electronic Stethoscopes, Computer in Cardiology, Memphis, TN, 2002, pp. 653-656.
T. Oskiper and R.L. Watrous, Detection of the First Heart Sound Using A Time-Delay Neural Network, Computers in Cardiology, Memphis, TN, 2002, pp. 537-540.
V. Kudriavtsev, et al., Heart Energy Signature (HES) Studies of Ped. Heart Murmurs Utilizing Ears-On Dataset of Pre-Recorded Heart Sounds, Biosignetics Corp., NH, Sep. 2005, pp. 1-15.
V. Kudriavtsev, et al., Hemodynamic Pressure Instabilities and Their Relation to Heart Auscultation, 5th International Symposium on Computational Technologies for Fluid/Thermal/Chemical/Stressed Systems with Industrial Applications, Jul. 25-29, 2004, San Diego, pp. 1-10.
Computer Aided Auscultation of the Heart The Clinical Opportunity, Zargis Medical Corp., Princeton, NJ, 2004, pp. 1-17.
T. Oskiper, R.L. Watrous, Results on the Time Frequency Characterization of the First Heart Sound in Normal Man, Conf. IEEE Eng. Med. Bio. Soc., Houston, TX, Oct. 23-26, 2002, pp. 126-127.
L. Gamero, R.L. Watrous, Detection of the First and Second Heart Sound Using Probabilistic Models, 25th Int. Conf. IEEE Eng. in Medicine and Biology Soc., Cancun, Mexico, Sep. 17-21, 2003, pp. 2877-2880.
R. Watrous, A Brief Survey of Computer-Aided Auscultation of the Heart: From Anatomy to Applications, Lecture Series in Elect, and Electrical Eng. Dept. of Elect. and Electrical Eng., University College, Dublin, Ireland, May 4, 2005, p. 1.
Heart Energy Signature Visualization System, V3.6, Biosignetics Corp., 2004-2007, pp. 1-9.
Dean Reske and Zahra Moussavi, Design of a Web-Based Remote Health-Monitoring System, Proceedings of the Second Joint EMBS/BMES Conference, Oct. 23-26, 2002, Houston, TX, pp. 1847-1848.
Wah W. Myint and Bill Dillard, An Electronic Stethoscope with Diagnosis Capability, IEEE, Mar. 2001, Athens, OH, pp. 133-137.
Electronic Stethoscope Model 4100 with Ambient Noise Reduction, 3M Littmann, 2005, pp. 1-14.
Y. Bronshteyn, et al., Maximizing Interpretable Heart Sounds in the Emergency Department Using Digital Auscultation and Computerized Analysis, Society for Academic Emergency Medicine Presentation Poster, Annual Meeting, circa 2007, p. 1.
A. Storrow, et al., Optimizing Computer Analyzed Heart Tones, Society for Academic Emergency Medicine Presentation Poster, Annual Meeting, circa 2006, p. 1.
V. Kudriavtsev, et al., New Tool to Identify Still's Murmurs, Pediatric Academic Societies Annual Meeting, Abstract and Presentation Poster, San Francisco, Apr. 29-May 2, 2006, p. 1.
Stethographics Handheld STG, Stethographics, Inc., Westborough, MA, United States, circa 1998-2004, pp. 1-2.
16 Channel STG User Manual, Stethographics, Inc., Westborough, MA, United States, circa 1998-2004, pp. 1-7.
STG User Manual, Stethographics, Inc., Westborough, MA, United States, 1998-2004, pp. 1-14.
Stethographics STG for Personal Computers, Stethographics, Inc., Westborough, MA, United States, circa 1998-2004, pp. 1-2.
Eurorack UB1202 User Manual, Behringer USA, Inc., Bothell, WA, United States, Jan. 2004, pp. 1-11.
UA-25&UA-4FX Driver Installation, Roland Corporation, Los Angeles, CA, United States, circa 2004, p. 1.
Microsoft Windows XP Tutorial, Microsoft Corporation, Redmond, WA, United States, circa 2003, pp. 1-20.
Sabatino, Michael; et al., Advances Beyond the Stethoscope for Acquiring Data on the Function of the Human Respiratory System, Biomedical Problems of the 21st Century/1st Annual Binghamton Biomedical Research Conference Symposium and Poster Session, Poster, Binghamton, New York, United States, Mar. 25, 2006, p. 1.
Simon Users Manual, IBM Corporation, 1994, pp. 1-41.
CDM 180 User Manual, Verizon Wireless, circa Jan. 2006, pp. 1-63.

(56) References Cited

OTHER PUBLICATIONS

CDM8945 User Guide, UTStarcom Personal Communications, circa Jan. 2006, pp. 1-75.
CDM-8615 Owner's Manual, Audiovox Communications Corporation, United States, circa 2004, pp. 1-67.
Cdm-8500, Audiovox Communications Corporation, United States, circa Feb. 2003, pp. 1-77.
VX3200 User Guide, LG Electronics Inc., circa 2004, pp. 1-60.
GPRS Phone User's Manual Model: G5400, LG Electronics Inc., circa Nov. 2004, pp. 1-89.
LG 8500 User Guide, LG Electronics Inc., circa Nov. 2006, pp. 1-81.
LG 8100 User Guide, LG Electronics Inc., circa Mar. 2006, pp. 1-95.
Telus User Guide LG6190, LG Electronics Inc., circa 2004, pp. 1-234.
LG 6070 Cellular Phone, LG Electronics Inc., 2004, pp. 1-61.
LG-5450 Cellular Phone Owner's Manual, LG Electronics Inc., circa 2003, pp. 1-62.
LG 4015 User Guide, LG Electronics Canada Inc., circa 2004, pp. 1-114.
LG 3300, LG Electronics Inc., circa 2005, pp. 1-81.
LG 550 User Guide, LG Electronics Inc., circa Nov. 2006, pp. 1-92.
LG 325, LG Electronics Inc., circa 2005, pp. 1-80.
LG 245 User Guide, LG Electronics Inc., circa Sep. 2006, pp. 1-78.
LG 210 User Guide, LG Electronics Inc., circa Aug. 2006, pp. 1-72.
Telus LG 200 User Guide, LG Electronics Inc., circa 2005, pp. 1-193.
LG 125, LG Electronics Inc., circa 2005, pp. 1-75.
LG 9200 User Guide, LG Electronics Inc., circa Jun. 2006, pp. 1-90.
T-Mobile Sidekick Owner's Manual, Danger, Inc., 2002-2003, pp. 1-259 (reference submitted in two parts).
HP iPAQ Pocket PC h6300 Series User's Guide, Hewlett-Packard Development Company, L.P., Jun. 2004, pp. 1-238 (reference submitted in two parts).
HP iPAQ hw6500 Mobile Messenger Series, Hewlett-Packard Development Company, L.P., Jun. 2005, pp. 1-170 (reference submitted in two parts).
PN-3200 User's Manual, Pantech, circa Aug. 2005, pp. 1-181 (reference submitted in two parts).
860, Utstarcom Communications, circa 2005, pp. 1-73.
Pocket PC Phone User Manual, Utstarcom Communications, circa 2005, pp. 1-138.
IP Australia Patent Examination Report No. 1, Application No. 2007228414, Applicant: Sabatino, Michael, Jun. 15, 2012, pp. 1-4.
Zdeblick, Mark, et al., Pharma-Informatics System, U.S. Appl. No. 60/790,335, Proteus Biomedical, Inc., Apr. 7, 2006, pp. 1-114.
Zdeblick, Mark, et al., Pharma-Informatics System, U.S. Appl. No. 60/694,078, Proteus Biomedical, Inc., Jun. 24, 2005, pp. 1-107.
Zdeblick, Mark, et al., Pharma-Informatics System, U.S. Appl. No. 60/676,145, Proteus Biomedical, Inc., Apr. 28, 2005, pp. 1-46.
Fleming, Robert, et al., In-Vivo Low Voltage Oscillator, U.S. Appl. No. 60/829,832, Proteus Biomedical, Inc., Oct. 17, 2006, pp. 1-29.
Robertson, Timothy L. et al., Medical Diagnostic and Treatment Platform Using Near-Field Wireless Communication of Information Within a Patient's Body, U.S. Appl. No. 60/713,680, Proteus Biomedical, Inc., Sep. 1, 2005, pp. 1-62.
UTRA-UTRAN Long Term Evolution (LTE) and 3GPP System Architecture Evolution (SAE), 3GPP, 2005-2006, pp. 1-8.
Dahlman, Erik, et al., The 3G Long-Term Evolution—Radio Interface Concepts and Performance Evaluation, Vehicular Technology Conference (VTC) 2006-Spring, Melbourne, Australia, May 2006, pp. 137-141, IEEE 63rd, vol. 1.
IP Australia Patent Examination Report No. 2, Application No. 2007228414, Applicant: Sabatino, Michael, Aug. 9, 2012, pp. 1-4.
European Patent Office Examiner's Report, Application No. 07735072.6-1265, Applicant: Sabatino, Michael, Sep. 17, 2012, pp. 1-4.
IP Australia Patent Examination Report No. 3, Application No. 2007228414, Applicant: Sabatino, Michael, Sep. 12, 2012, pp. 1-3.
Stefan Parkvall, Long-Term 3G Evolution—Radio Access, Ericsson, Nov. 2005, pp. 1-17.
Erik Dahlman, 3G Long-Term Evolution, Ericsson, 2005, pp. 1-36.
Hannes Ekstrom, et al., Technical Solutions For The 3G Long-Term Evolution, IEEE Communications Magazine, Mar. 2006, pp. 38-45, vol. 44, No. 3.
Wireless LAN Standards and Organizations, Northern Virginia Community College, Alexandria, United States, Feb. 2005, pp. 1-34.
Eli Sofer, Tutorial On Multi Access OFDM (OFDMA) Technology, Runcorn Technologies Ltd., Jan. 4, 2005, pp. 1-49.
Doyle, D., et al., Monitoring Hemodialysis Vascular Access by Digital Phonoangiography, Ann Biomed Eng., Jul. 2002-Aug.; 30(7): pp. 982.
Grenier, MC, et al., Clinical Comparison of Acoustic and Electrical Stethoscopes and Design of a New Electronic Stethoscope, Am J Cardiol., Mar. 1, 1998; 81(5): pp. 653-656.
Hadjileontiadis, LJ, et al., A Wavelet-Based Reduction of Heart Sound Noise From Lung Sounds, Int J Med Inform., Oct. 1998-Dec.; 52(1-3): pp. 183-190.
Thompson, WR, et al., Automated Cardiac Auscultation for Detection of Pathologic Heart Murmurs, Pediatr Cardiol., Sep. 2001-Oct.; 22(5): pp. 373-379.
Degroff, CG, et al., Artificial Neural Network-Based Method of Screening Heart Murmurs in Children, Circulation, Jun. 5, 2001; 103(22): pp. 2711-2716.
McNulty, S., et al., Radiofrequency Transmission to Monitoring Devices in the Operating Room: A Simulation Study, Anesth Analg., Feb. 2001; 92(2): pp. 384-388.
Larkin, M., Pediatric Heart Sounds Assessed by Computer, Lancet, Jun. 9, 2001; 357(9271): pp. 1856.
Krishnan, S., et al., Auditory Display of Knee-Joint Vibration Signals, J Acoust Soc Am., Dec. 2001.; 110(6): pp. 3292-3304.
Rao, AS, et al., Auscultation in the New Millennium, J Assoc Physicians India., Jul. 2001; 49: pp. 731-733.
Chen, D., etaL, Time-Frequency Analysis of the First Heart Sound: Part 3, Med Biol Eng Comput., Sep. 1997.; 35(5): pp. 455-461.
Widmalm, SE, et al., The Frequency Range of TMJ Sounds, J Oral Rehabil., Apr. 2003; 30(4): pp. 335-346.
Craine, BL, et al., Use of a Computerized GI Sound Analysis System, Am J Gastroenterol., Apr. 2003; 98(4): p. 944.
Hayek, CS, et al.. Wavelet Processing of Systolic Murmurs to Assist with Clinical Diagnosis of Heart Disease, Biomed Instrum Technol., Jul. 2003-Aug.; 37(4): pp. 263-270.
Harper, VP, et al., Modeling and Measurement of Flow Effects on Tracheal Sounds, IEEE Trans Biomed Eng., Jan. 2003; 50(1): pp. 1-10.
Dahl, LB, et al., Heart Murmurs Recorded by a Sensor Based Electronic Stethoscope and E-mailed for Remote Assessment, Arch Dis Child., Oct. 2002; 87(4): pp. 297-301.
Kraman, SS, et al., Are Minidisc Recorders Adequate for the Study of Respiratory Sounds?, Biomed Instrum Technol., May 2002-Jun.; 36(3): pp. 177-182.
Sebald, DJ, et al., Narrowband Auscultatory Blood Pressure Measurement, IEEE Trans Biomed Eng., Sep. 2002.; 49 (9): pp. 1038-1044.
Pinto, L., et al., Blood Pressure Measurement in Noise Intensive Environments Using Adaptive Interference Cancellation, Ann Biomed Eng., May 2002; 30(5): pp. 657-670.
Folland, R., et al., Classifying Coronary Dysfunction Using Neural Networks Through Cardiovascular Auscultation, Med Biol Eng Comput.; May 2002; 40(3): pp. 339-343.
Yuki, M., et al., Is A Computerized Bowel Sound Auscultation System Useful for the Detection of Increased Bowel Motility?, Am J Gastroenterol., Jul. 2002; 97(7): pp. 1846-1847.
Mansy, HA, et al., Acoustic Characteristics of Air Cavities at Low Audible Frequencies with Application to Pneumoperitoneum Detection, Med Biol Eng Comput, Mar. 2001; 39(2): pp. 159-167.
Patel, SB, et al., An Adaptive Noise Reduction Stethoscope for Auscultation in High Noise Environments, J Acoust Soc Am., May 1998; 103(5 Pt 1): pp. 2483-2491.
Pacht, ER, et al., Effectiveness of Telemedicine in the Outpatient Pulmonary Clinic, Telemed J., 1998; 4(4): pp. 287-292.

(56) References Cited

OTHER PUBLICATIONS

Jain, AK, Betaru: An Indigenously Designed Cordless Stethoscope, Indian Pediatr., May 2000, 37(5): pp. 566-567.
Feinstein, NF, Fetal Heart Rate Auscultation: Current and Future Practice, J Obstet Gynecol Neonatal Nurs., May 2000-Jun.; 29(3): pp. 306-315.
Kofos, D., et al., Telemedicine in Pediatric Transport: A Feasibility Study, Pediatrics, Nov. 1998.; 102(5): pp. 1-3.
Craine, BL, et al.. Computerized Auscultation Applied to Irritable Bowel Syndrome, Dig. Dis. Sci., Sep. 1999; 44(9): pp. 1887-1892.
Martin, CC, et al.. Teaching Cardiology Auscultation: A Wireless FM Broadcast System, Tex Heart Inst. J., 1998; 25(3): pp. 218-219.
AMD SmartSteth, Jan. 29, 2003 and Jun. 3, 2005, pp. AMD002345-AMD002384, AMD Telemedicine, Lowell, US.
510(k) Submission—Littmann Electronic Stethoscope, Model 3000, Jul. 16, 2004, pp. AMD002139-AMD002145, 3M Health Care, St. Paul, US.
Boudreau, User Manual for the ADCOM iDOC Telemedicine Cart, Jul. 8, 2004, pp. AMD002204-AMD-2225, North Network.
DASYLab Version 7.0 Book 1: User Guide, 2002, pp. AMD001909-AMD002126, National Instruments, Amherst, US.
510(k) Submission—Liberty Modification to Audicor System, Nov. 4, 2004, pp. AMD002183-AMD002203, Inovise Medical, Inc., Portland, US.
QS2 Mapping System Quick Reference Guide, pp. AMD002226-AMD002228.
510(k) Submission—ZAC Energy and Timing Display, Sep. 8, 2004, pp. AMD002247-AMD002263, Zargis Medical Corp , Princeton, US.
510(k) Submission—E-Steth Electronic Stethoscope, Jun. 11, 2001, pp. AMD002336-AMD002340, e-Med Innovations, Inc., Dallas, US.
Sarkar, Examination Report, dated Dec. 23, 2016, pp. 1-9, Intellectual Property India, New Delhi, IN.
Smartsteth User's Guide, 2001-2002, pp. AMD002229-AMD 002246, AMD Telemedicine, Inc., Lowell, US.
510(k) Submission—Personal Telemedicine System, Jun. 22, 1995, pp. AMD005245-AMD005504, American TeleCare, Inc., Eden Prairie, MN, US.
510(k) Submission—Personal Telemedicine Module, Nov. 8, 1996, pp. AMD005505-AMD005630, American Telecare, Inc. Eden Prairie, MN, US.
510(k) Submission—Personal Telemedicine Module, Oct. 9, 1997, pp. AMD005631-AMD005787, American TeleCare, Inc., Eden Prairie, MN, US.

\* cited by examiner

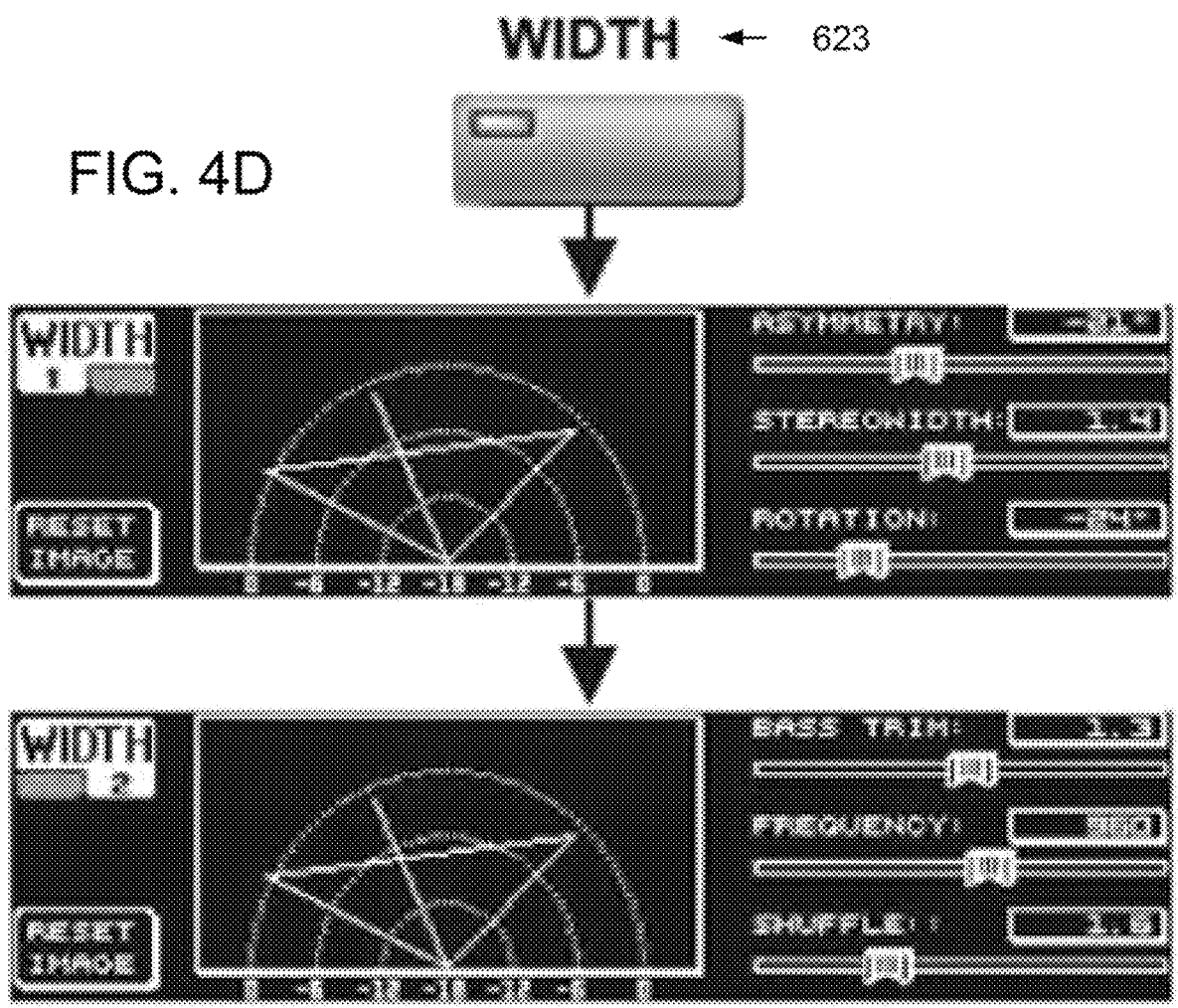

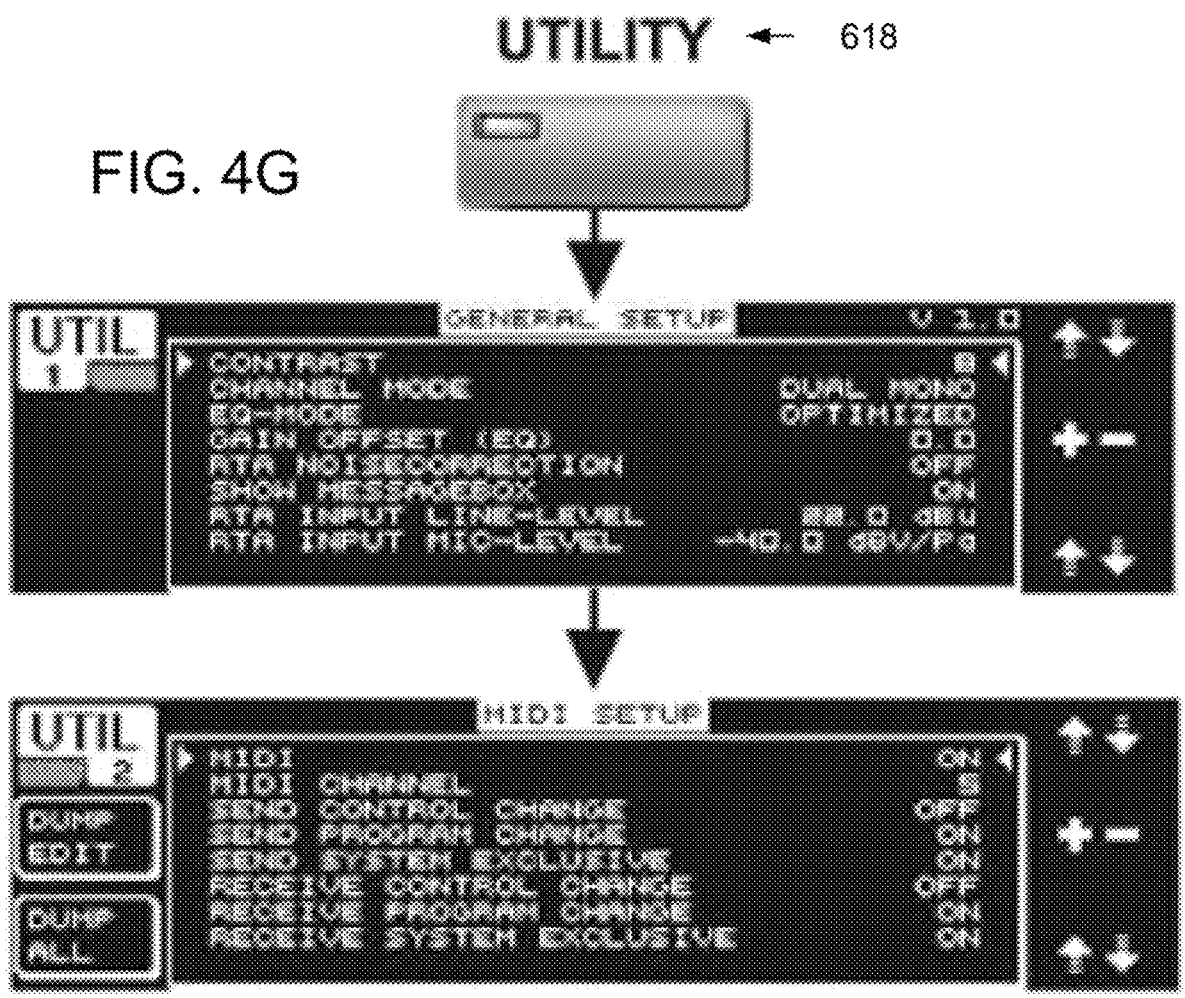

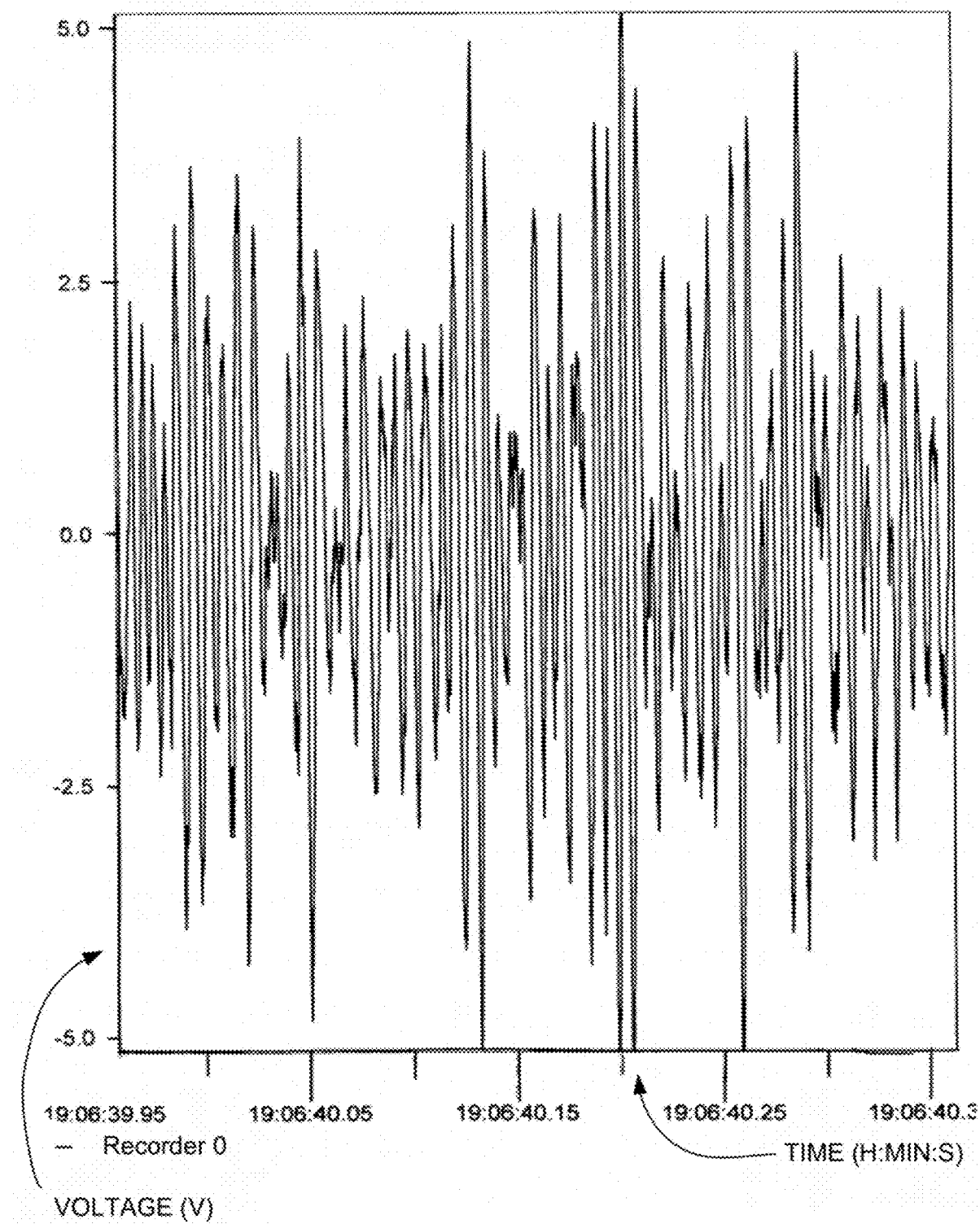

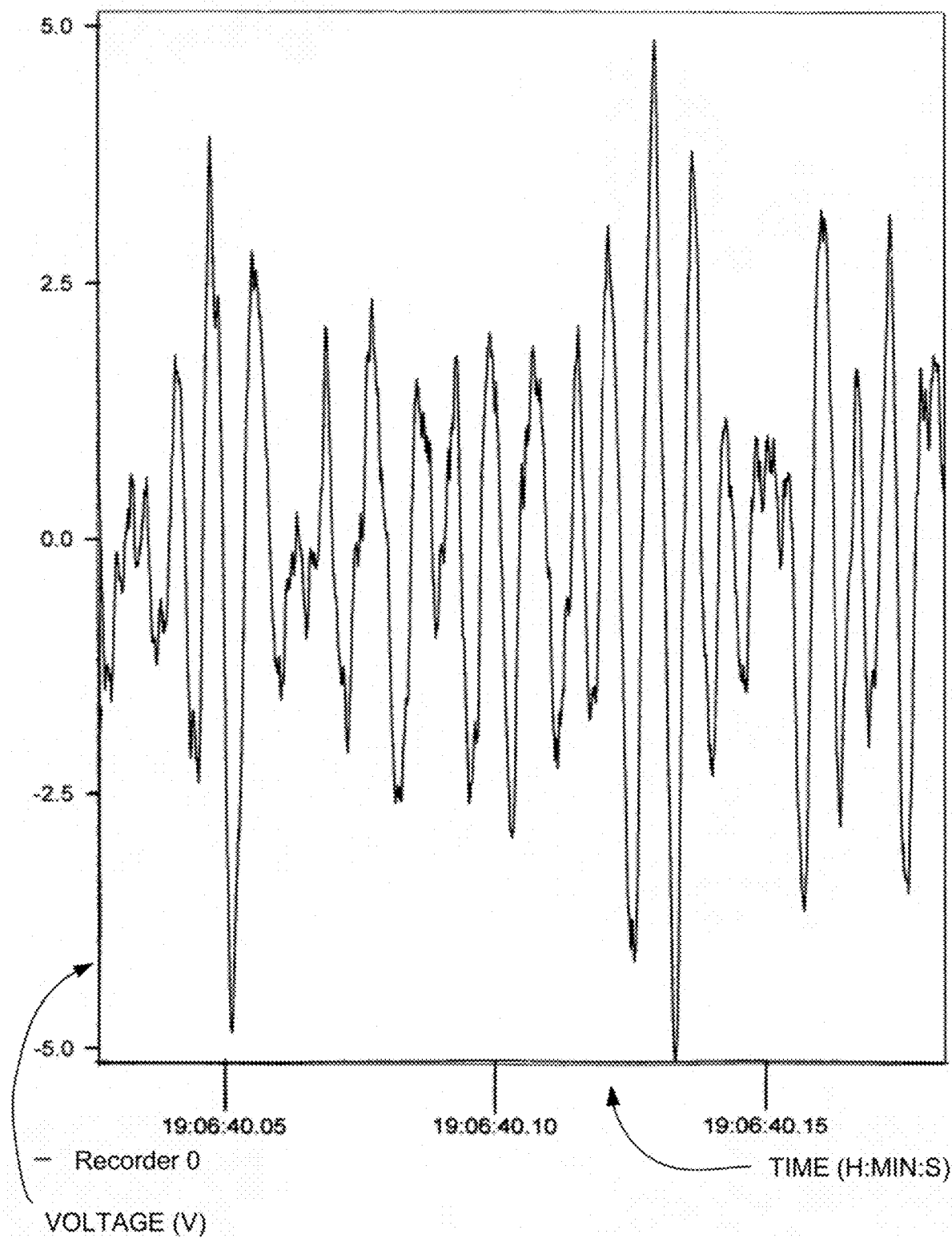

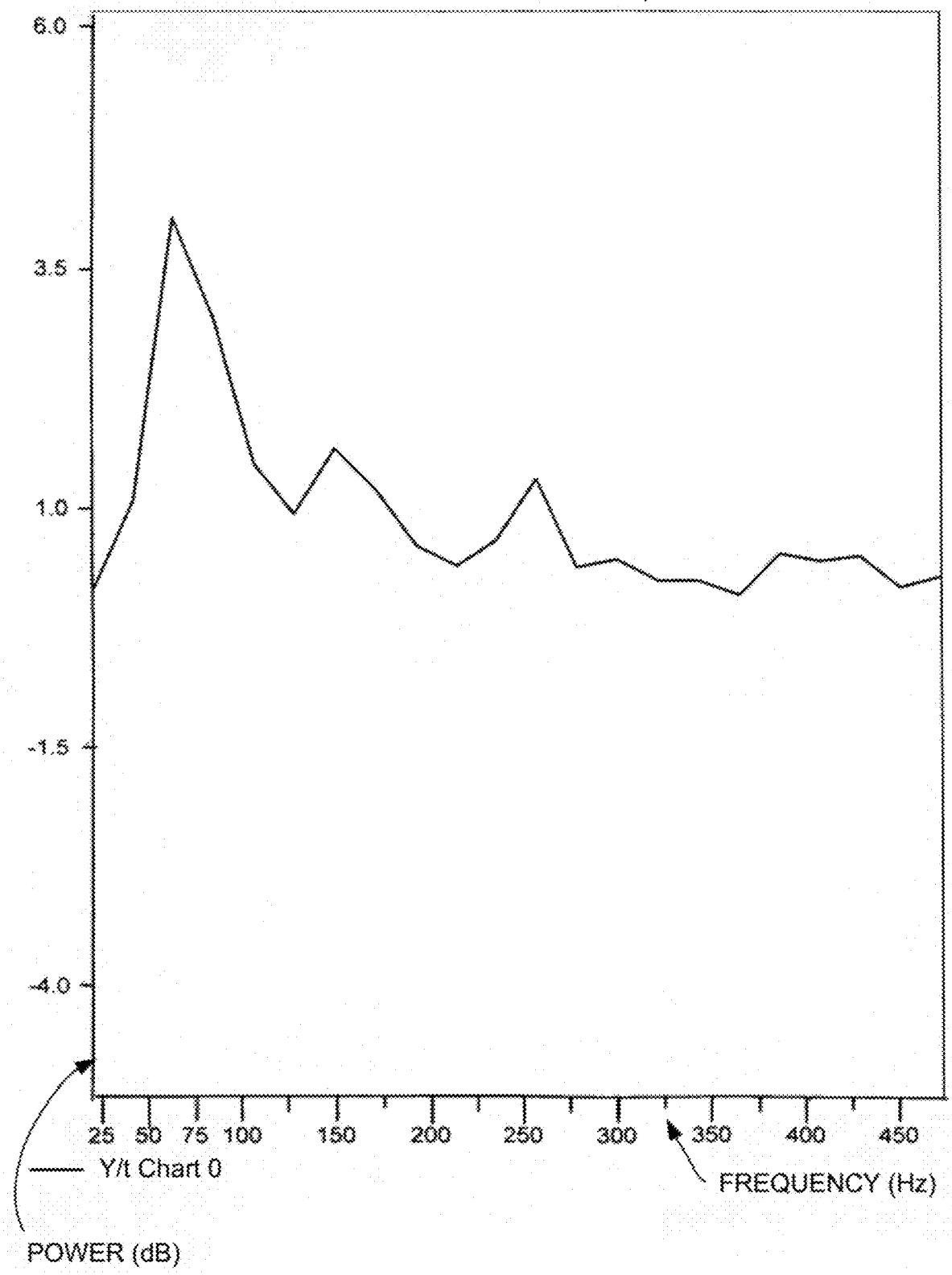

FIG. 9

| Number | List 0 |
|--------|--------|
| 0 | 0.32416 |
| 1 | 0.24833 |
| 2 | 0.26159 |
| 3 | 0.38564 |
| 4 | 0.39383 |
| 5 | 0.27714 |
| 6 | 0.33288 |
| 7 | 0.28556 |
| 8 | 0.36188 |
| 9 | 0.39170 |
| 10 | 0.41769 |
| 11 | 0.37412 |
| 12 | 0.28504 |
| 13 | 0.31108 |
| 14 | 0.30409 |
| 15 | 0.30258 |
| 16 | 0.24723 |
| 17 | 0.30873 |
| 18 | 0.44627 |
| 19 | 0.40087 |
| 20 | 0.33600 |
| 21 | 0.31696 |
| 22 | 0.39488 |
| 23 | 0.38666 |

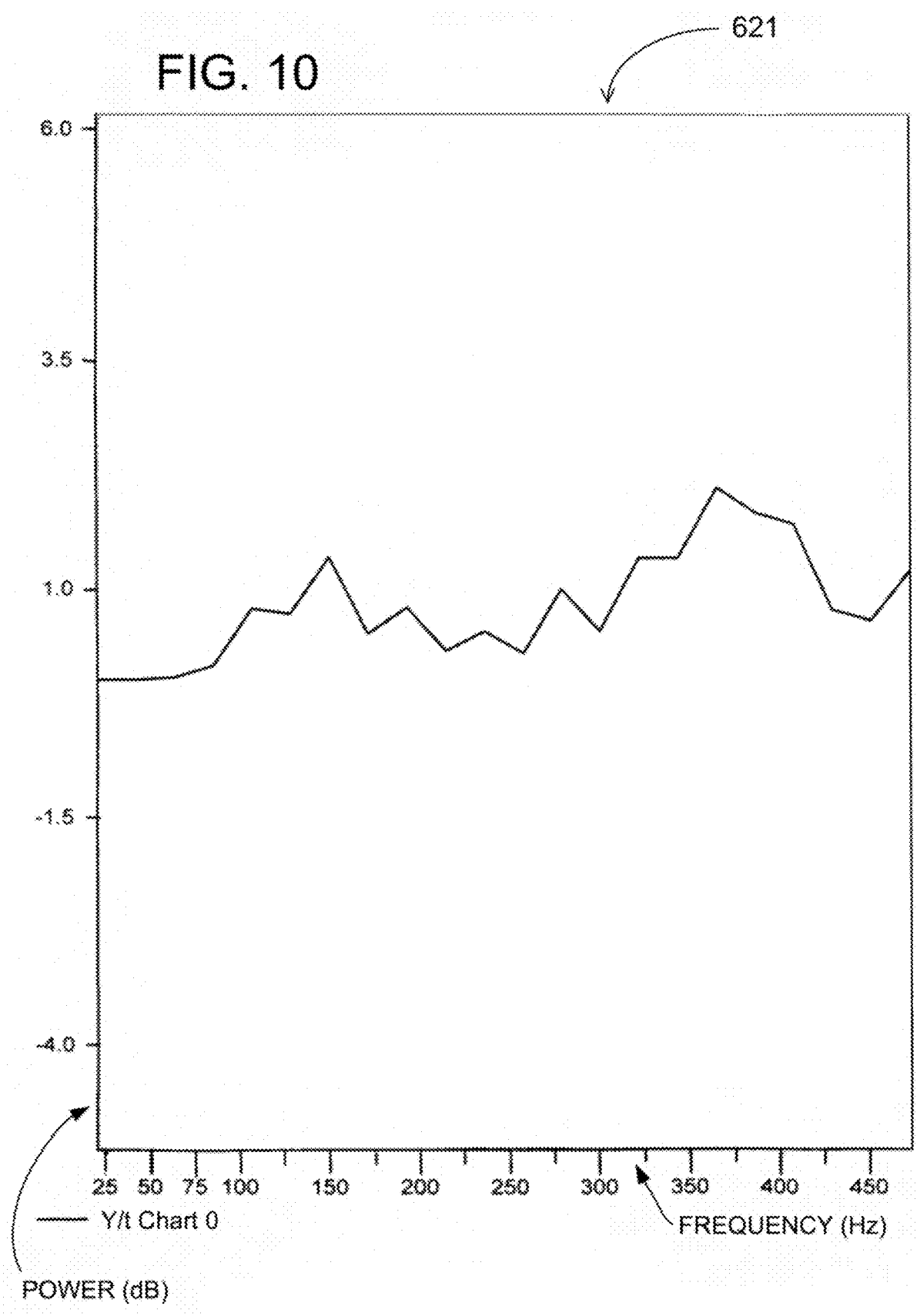

FIG. 11A

| Number | List 0 |
|---|---|
| 144 | 0.16453 |
| 145 | 0.19866 |
| 146 | 0.25353 |
| 147 | 0.30213 |
| 148 | 0.27350 |
| 149 | 0.32605 |
| 150 | 0.38357 |
| 151 | 0.38844 |
| 152 | 0.39335 |
| 153 | 0.40621 |
| 154 | 0.36097 |
| 155 | 0.36865 |
| 156 | 0.34936 |
| 157 | 0.35348 |
| 158 | 0.37133 |
| 159 | 0.38622 |
| 160 | 0.37478 |
| 161 | 0.35564 |
| 162 | 0.37702 |
| 163 | 0.36008 |
| 164 | 0.36676 |
| 165 | 0.36367 |
| 166 | 0.34848 |
| 167 | 0.34179 |
| 168 | 0.35888 |
| 169 | 0.31170 |
| 170 | 0.34592 |
| 171 | 0.36733 |
| 172 | 0.35863 |
| 173 | 0.34091 |
| 174 | 0.33474 |
| 175 | 0.36267 |
| 176 | 0.36828 |
| 177 | 0.34860 |
| 178 | 0.35901 |
| 179 | 0.36568 |
| 180 | 0.34046 |
| 181 | 0.33658 |
| 182 | 0.34959 |
| 183 | 0.29098 |
| 184 | 0.33565 |

FIG. 11B

| Number | List 0 |
|---:|---:|
| 185 | 0.32099 |
| 186 | 0.30145 |
| 187 | 0.34859 |
| 188 | 0.34272 |
| 189 | 0.37439 |
| 190 | 0.32083 |
| 191 | 0.31364 |
| 192 | 0.17720 |
| 193 | 0.29043 |
| 194 | 0.34371 |
| 195 | 0.36921 |
| 196 | 0.37567 |
| 197 | 0.38466 |
| 198 | 0.36238 |
| 199 | 0.35867 |
| 200 | 0.34770 |
| 201 | 0.33068 |
| 202 | 0.35571 |
| 203 | 0.29219 |
| 204 | 0.32458 |
| 205 | 0.36456 |
| 206 | 0.34355 |
| 207 | 0.38699 |

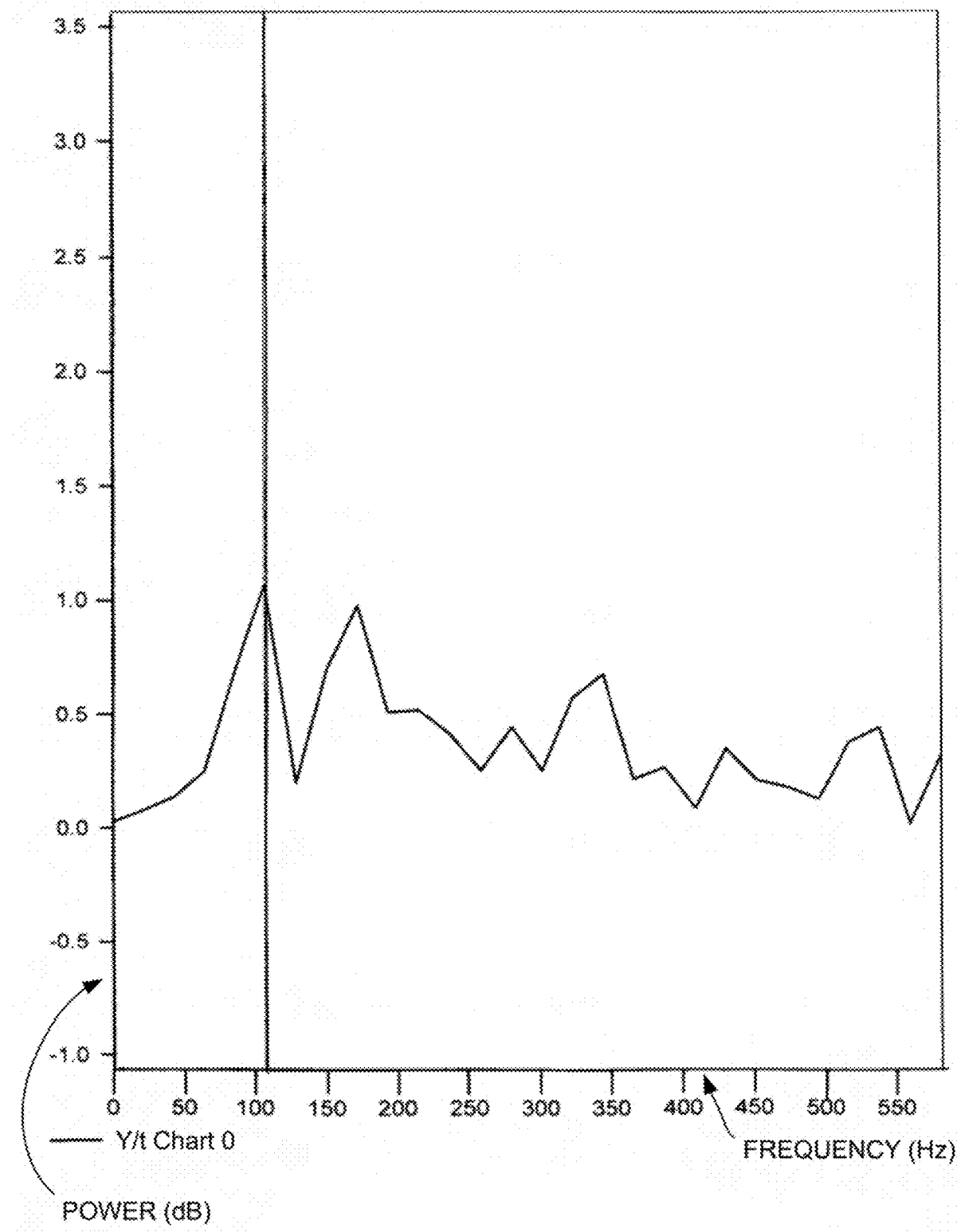

FIG. 12B

| Number | List 0 |
|---|---|
| 24 | 0.578 |
| 25 | 1.728 |
| 26 | 1.008 |
| 27 | 0.558 |
| 28 | 0.880 |
| 29 | 0.944 |
| 30 | 1.019 |
| 31 | 0.602 |
| 32 | 0.532 |
| 33 | 0.850 |
| 34 | 1.071 |
| 35 | 1.244 |
| 36 | 0.553 |
| 37 | 0.601 |
| 38 | 0.550 |
| 39 | 0.637 |
| 40 | 1.164 |
| 41 | 0.548 |
| 42 | 0.682 |
| 43 | 1.525 |
| 44 | 2.146 |
| 45 | 1.216 |
| 46 | 0.462 |
| 47 | 0.429 |
| 48 | 0.199 |
| 49 | 0.407 |
| 50 | 0.629 |
| 51 | 0.589 |
| 52 | 0.803 |
| 53 | 0.596 |
| 54 | 0.473 |
| 55 | 0.239 |
| 56 | 0.699 |
| 57 | 1.176 |
| 58 | 1.875 |
| 59 | 0.982 |
| 60 | 0.267 |
| 61 | 0.854 |
| 62 | 1.341 |
| 63 | 0.253 |
| 64 | 0.584 |

FIG. 12C

| Number | List 0 |
|---|---|
| 65 | 1.380 |
| 66 | 1.579 |
| 67 | 0.614 |
| 68 | 0.793 |
| 69 | 0.249 |
| 70 | 0.626 |
| 71 | 0.517 |
| 72 | 0.692 |
| 73 | 0.843 |
| 74 | 0.237 |
| 75 | 0.996 |
| 76 | 0.536 |
| 77 | 0.344 |
| 78 | 1.064 |
| 79 | 1.493 |
| 80 | 0.816 |
| 81 | 0.100 |
| 82 | 0.440 |
| 83 | 1.676 |
| 84 | 0.877 |
| 85 | 0.423 |
| 86 | 0.724 |
| 87 | 1.066 |

ACQUIRING AND PROCESSING ACOUSTIC ENERGY EMITTED BY AT LEAST ONE ORGAN IN A BIOLOGICAL SYSTEM

RELATED APPLICATIONS

This application is a continuation of copending U.S. patent application Ser. No. 13/430,561 filed Mar. 26, 2012, entitled "APPARATUS FOR ACQUIRING, PROCESSING AND TRANSMITTING PHYSIOLOGICAL SOUNDS," which claimed priority to copending U.S. patent application Ser. No. 11/602,017 filed Nov. 20, 2006 entitled, "SYSTEM AND METHOD FOR ACQUISITION AND ANALYSIS OF PHYSIOLOGICAL AUDITORY SIGNALS," which claimed priority to U.S. Prov. Pat. App. No. 60/785,357 filed on Mar. 23, 2006, entitled "SYSTEM AND METHOD FOR ACQUISITION AND ANALYSIS OF PHYSIOLOGICAL AUDITORY SIGNALS." All of the contents of U.S. patent application Ser. No. 13/430,561, U.S. patent application Ser. No. 11/602,017, and U.S. Prov. Pat. App. No. 60/785,357 are incorporated herein by reference.

BACKGROUND

Throughout this application, various publications are referenced. The disclosures of these publications in their entireties are hereby incorporated by reference into this application in order to more fully describe the state of the art as known to those skilled therein, as of the date of the disclosure described and claimed herein.

Auscultation of the lung and heart is probably the most widely used physical diagnostic method in respiratory and cardiac disease. However, due to the limitations of the human auditory system, auscultation has such low sensitivity and specificity that many physicians no longer rely solely on it as a diagnostic tool. Although digital acquisition and analysis of physiologic sounds has the potential to be of tremendous diagnostic/therapeutic benefit to patients, the medical community has been slow to embrace this technology. In order to overcome this obstacle, any system for digital acquisition and analysis of physiologic sounds must be lightweight and easy for individuals without technical expertise to operate and modify. In addition, all generated results must be presented in a format that allows for rapid interpretation and correlation with important physiologic values obtained from other tests.

Physiologic sounds may be captured electronically, processed, and transmitted back to the clinician thus enabling the human auditory system to obtain greater information conveyed by the signal. For example, U.S. Pat. No. 5,774,563 discloses a device for acquiring physiologic sounds. Electronic circuitry embedded in the device enables the operator to filter and amplify the incoming signal. Furthermore, this device also allows the user to listen to the post-processed signal through implementation of earpieces. However, no plan is described for enabling clinicians of ordinary ability to modify the system. Thus, the effective frequency range measured by this device is 70-480 Hz, which is essentially unalterable, has minimal clinical applications. In addition, this system does not provide a means for digital acquisition/display/analysis of the recorded signal, which serves to severely limit the use of this device in a clinical setting. Other forms of analogous art, which are based on these same principles, share similar disadvantages.

Analogous inventions in the art have depicted devices capable of acquiring, processing and digitally recording/analyzing physiologic signals. U.S. Pat. No. 6,139,505 discloses an electronic stethoscope for the digital acquisition and analysis of physiologic sounds. The device consists of a microphone, which can be embedded inside conventional chest pieces. After amplification and filtering, the signal is transferred to an analogue to digital converter (A/D converter) for computer analysis. The system disclosed contains a modifiable number of independent transducers to record physiologic sounds at any particular location, which the operator desires. The device allows for amplification/filtering of the recorded signal, store these recordings in memory, perform root mean square (RMS) and time expanded waveform analysis, and display data on a monitor for visual analysis/printing. This device is also fairly easy to modify/upgrade/repair and includes a built in program for analyzing respiratory sounds and generating a probable diagnosis based on this information.

However, this device does not disclose a method to enable the physicians to listen to the sound as it is being recorded, but instead, requires them to discern phases of the respiratory cycle simply by inspection of the time expanded waveform. The patent describes a method by which physiologic sound may be processed and transmitted to a computer workstation using analogue circuitry which is bulky and not easily customized thus limiting the device's practical application. Further, no information is given about how this device can be used for higher level analysis (such as performance of Fourier Transformation or wavelet) of the desired signal, only time expanded waveform analysis and RMS of the complete spectrum are illustrated. These quantities give incomplete information regarding the sound and the program is not easily operated/modified by a clinician of ordinary skill. Lastly, no method is outlined by the inventors for reducing the corruption of the data from inadvertent pickup of ambient noise or superimposed signals emitted from other organs in close proximity to the transducer. The probable diagnosis product available with this device is also extremely limited since it provides no quantitative information regarding the degree of functionality of the desired organ system. Although Murphy's electronic stethoscope represents significant improvement from analogous art as a system for the display and analysis of physiologic sounds, the limitations of this device as described above decrease its usefulness in a clinical setting.

Additional devices have been patented which attempt to provide more sophisticated means for mathematically analyzing physiologic sounds and transmitting results to remote locations. One such example can be found in U.S. Pat. No. 6,699,204, which illustrates a device for recording physiologic sound using multiple sensors that are secured to a patient via a harness. Physiologic sound can be recorded by the sensors and relayed to a processing station for filtering/amplification using analogue circuits. The signal is then transferred to a sampler Ech (sound card) for digital recording via analogue circuitry or modem (not shown). With the aid of a specialized calculation manager (Matlab®) for example), the device can evaluate a set of transformed intensity levels, each associated with a predetermined sound frequency and means for storing each transformed intensity level in correspondence with an associated frequency for the purpose of displaying these intensity levels, transformed on the basis of frequencies as a spectral representation of the auscultation sound.

The device depicted by Kehyayan et al. is a further improvement over analogous art since it provides an accurate spectral representation of the auscultation sound as the intensity varies with time. However, a physician of ordinary ability cannot be expected to have the technical expertise necessary to easily operate and/or modify this analysis program in order to examine a wide array of physiologic sounds. Also, no plan is outlined by the inventor for preventing extraneous sounds (from ambient noise or sound emitted from other organs) from influencing the results displayed on the spectral plots. Lastly, the spectral plots contain too much information for a clinician to interpret in a timely manner. Thus, it is unlikely that the invention proposed by Kehyayan will be useful in a practical setting, and thereby widely embraced by the medical community.

SUMMARY

Various embodiments of the present invention are generally directed to acquiring, processing and transmitting acoustic energy data.

In accordance with various embodiments, acquiring, processing and transmitting acoustic energy data is provided. A sensor for acoustic energy is utilized to convert analogue signals into an electrical output. The electrical output is converted to digital data. The digital data is processed by use of a processing unit. Transmission of the digital data is initiated over a wireless network. Electrical current is supplied to the processing unit through a battery.

These and other features and advantages which characterize the various embodiments of the present invention can be understood in view of the following detailed discussion and the accompanying drawings.

BRIEF DESCRIPTION OF THE DRAWINGS

FIGS. 4A-4L illustrates a variety of operations which may be performed on the acquired data by the digital signal processor.

FIGS. 7A and 7B represent time expanded waveforms of physiologic sounds.

FIG. 8 is a graphical representation of the power spectrum density calculated using the Fast Fourier transformation from an incoming data stream representative of physiologic sounds received by the transducer positioned over the heart.

FIG. 9 depicts the sequential display of RMS values calculated from the PSD after processing for heart sounds. This data may then be used to assess the degree of functionality of the target organ.

FIG. 10 depicts the PSD calculated from tracheal breath sounds using the FFT.

FIGS. 11A and 11B depict the sequential display of RMS values calculated from the PSD after processing of the tracheal breath sound.

FIGS. 12A-12C depict the sequential display of values corresponding to the maximum frequency 12A and corresponding intensity 12B/12C from the desired portions of the PSD after processing of the incoming signal from the heart. Data is displayed as it is obtained from each incoming block.

DETAILED DESCRIPTION

Figure 1:
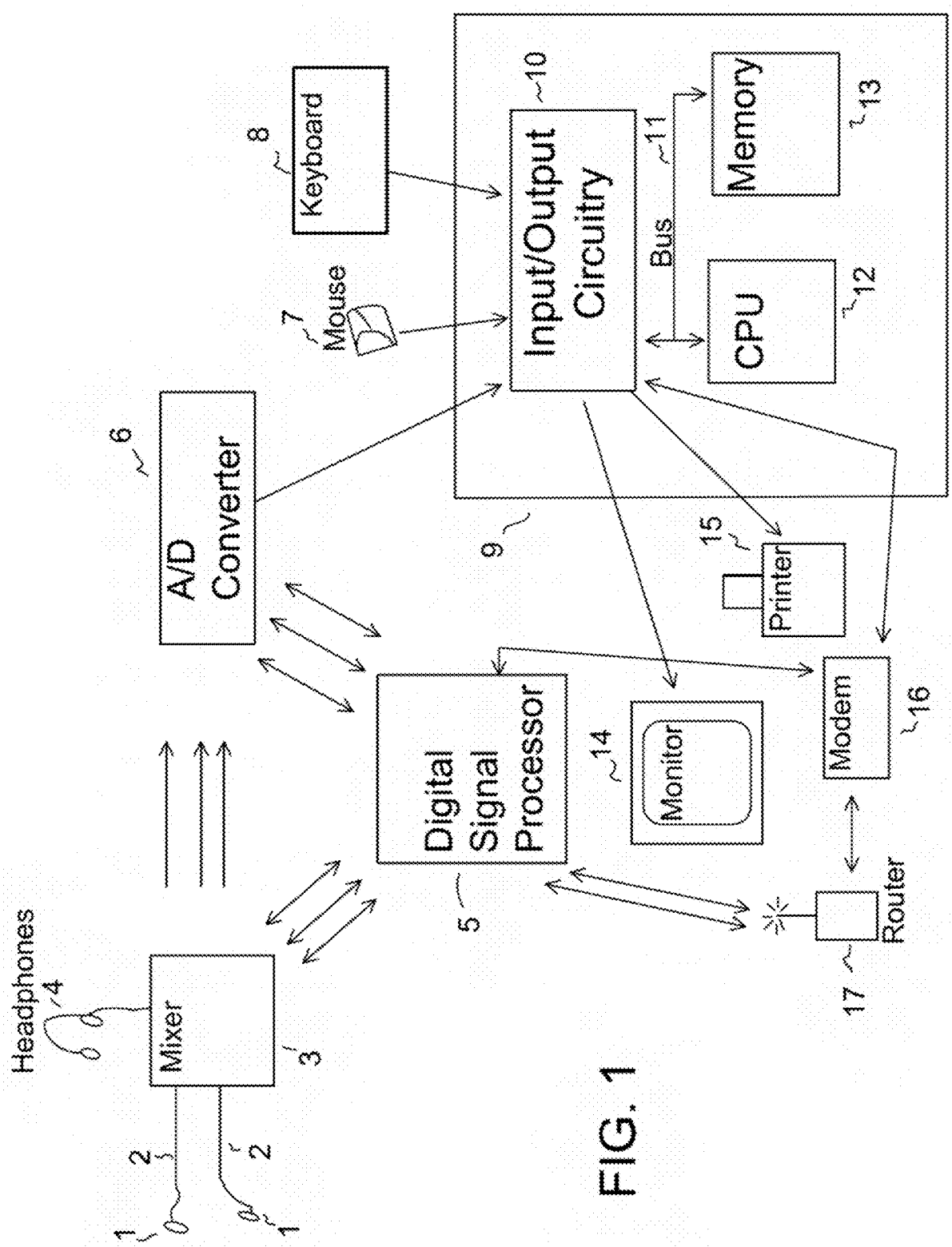
FIG. 1 provides a general overview of an exemplary embodiment disclosed.

It has been proven that organs in the human body emit characteristic physiologic signals when they are functioning in the absence of pathology.

One of the main obstacles to widespread acceptance of electronic stethoscopes is that these devices are too cumbersome, and also, too complicated for health care professionals to operate in a professional setting. A compact, customizable device may be useful. But most important, the device will be an improvement over analogous art by providing a simple interface which allows medical professionals with limited technical background to easily manipulate vital parameters such as block length, overlap, sampling rate, low/high pass filtering, adjusting the Fast Fourier Transformation (FFT) and RMS analysis to cover any component of the frequency spectrum, and applying data windows without the need for computer programming knowledge.

It may be useful to boost the accuracy of recording physiological sounds by providing the physician with an efficient method of eliminating background noise (which is either present in the ambient environment and/or emitted by other body organs in the vicinity of the transducer) from the desired signal in real time. Accomplishing this task will not only lead to greater accuracy in the measurement of physiologic sounds, but it will also allow the device to operate with a greater degree of autonomy when compared to analogous art.

Lastly, acoustic signals from human organs occur over many different frequency ranges (depending on the specific organ and any pathology present) and are often of minimal intensity. Therefore, detecting differences in these signals between normal physiologic and pathologic states over a finite time interval for any given organ requires a system of mathematical analysis with greater sensitivity than that described in many versions of analogous art. The device may provide a means for adjusting the frequency band in the Power Spectrum Density (PSD), which the RMS values are calculated from. The PSD results from performing the FFT on the digital data corresponding to the audio signal.

As noted above, this disclosure relates to a system for recording and analyzing physiologic sounds to provide the clinician with information relating to functional status of the organ being examined. This information may provide clues, that when combined with other elements of a diagnostic workup (history, physical exam, lab tests, medical imaging, etc.) may facilitate the diagnosis of various disease states (pulmonary disease for example). Consistent with other forms of analogous art, the system includes a plurality of transducers, such as microphones embedded in small rubber tubes coupled to a thin plastic diaphragm(s) which may be placed at pre-selected sites on the patient using either light pressure or a harness of some type. Physiologic signals of interest vibrate the plastic diaphragm, which transmits the sound by moving air molecules in the tube. The transducers detect these sounds and convert them into electrical signals. The system contains a preamplifier that not only increases the intensity of the incoming electrical signal, but also polarizes the transducers with an electromotive force (preferably 48 Volts) applied equally to both inputs to the sensor with respect to ground (phantom power). In order to provide this polarizing potential high voltage commercial alternating current is converted to high voltage direct current. This voltage is applied to same wires that carry the audio signal. Since the preamplifier can supply such high voltage (unlike many computer sound cards available commercially) the apparatus and method disclosed can make use of transducers with higher signal to noise ratios than those used in analogous art. Furthermore, portability may be maximized by supplying the phantom power through a alkaline, lithium-ion or other rechargable battery.

The system also includes a digital signal processor for conditioning the signal (filtering, gating, limiting, or excluding background noise). In an embodiment of the invention, analogue circuitry or a digital signal processor employing Super Harvard Architecture (SHARC) can be added for additional filtering, expansion, compression or conversion of the processed signal back to sound energy thereby enabling the operator to hear the altered sound in real time. After processing, the analogue signals generated by the transducers are converted into digital data and transferred to a computer workstation. In order to increase the portability of this device, digital data may be transmitted to the workstation over wireless internet. A further advantage of utilizing a SHARC processor is that optimal settings for detecting sound from a variety of sources may be stored in memory for instantaneous recall by the operator. These aforementioned settings which are programmed into the SHARC processor may enable the claimed invention to acquire properties of sound transmission which are identical to a conventional acoustic stethoscope. This is important because acoustic stethoscopes remain popular in clinical settings due to the fact that a tremendous amount of research has already been done with them and the steadfast hesitancy among healthcare professionals to abandon their use of these devices.

The computer station includes a microprocessor, input/output circuitry, and random access memory for data storage, one or more input devices (such as a keyboard or mouse), a modular interface with many different graphical displays of incoming data, and one or more output devices (such as a printer, monitor or modem for transmission over the Internet).

Executing on the computer is an application program constructed from a set of modular elements synthesized using a graphical programming language. The application program collects the data and organizes it into discrete sections (blocks) before moving it through a series of modules. By clicking on any specific module with the mouse, the operator can set the sampling rate, block size and overlap. Furthermore, the operator may elect to further high/low pass filter the data digitally or apply a mathematical window analogous to FFT processing in order to minimize distortion of calculated results.

After breaking the signal into multiple blocks (which correspond to discrete time intervals) and then pre-processing these blocks, the program calculates the power spectrum density of the portion of the signal contained in each block using the FFT. After calculation the computer displays the results graphically as a plot of Intensity vs. Frequency. These results are updated continuously as the PSD is calculated anew for each incoming block and the results of the previous block are saved in memory.

As the PSD is calculated for each incoming block, the computer may exclude portions of the PSD that are outside the selected thresholds specified by the operator. This is possible because the program may contain a trigger, which enables the operator to exclude portions of the spectrum, which are not of interest with a simple mouse click. Once the PSD is determined, the program calculates the root mean square (RMS) value of the signal in the frequency band(s) chosen by the operator. The computer performs this calculation on each incoming block and displays the data as a list during the time of operation. This method is highly advantageous to the clinician since it takes a very complicated quantity (the PSD of each block that gives information about the power of all frequency components in the block) and converts it into a simple quantity (RMS), while still relaying the necessary information about the signal to the clinician. Secondly, by performing these calculations on each incoming block of the data, the properties of the signal outlined above can be analyzed as they vary over time. The clinician can then use this information about an organ's spectral characteristics to assess its degree of functionality in a quick, inexpensive, accurate and non-invasive manner. The analysis program illustrated can be used either as a stand alone application or in combination with a number of additional program elements which may include patient's electronic medical records. As a result, this system has the potential to dramatically improve efficiency in the healthcare system and clinical outcomes for patients.

FIG. 1 provides an overview of the sound recording and analysis system of the present invention. This system includes a transducer 1, such as an analogue condenser microphone, which can be placed at various sites around the patient to listen to sounds emitted by different organs. It should be understood that the system could be expanded to include additional transducers 1 if desired so that data from multiple sites can be collected concurrently. To isolate the sensors from external sounds (and thereby improve signal to noise), they may be embedded in the tubing/chest pieces of conventional stethoscopes. The transducer(s) 1 may be held against the surface of the patient with mechanical pressure applied by the operator, adhesive tape or suitable strapping to prevent movement during the data acquisition process.

Leads 2 extending from the sensors are balanced cables with XLR inputs 97 that connect to a signal conditioning station. A suitable signal conditioning circuit could be the Eurorack 1202, a sound mixer 3 made by Behringer. This station performs many important functions. First, it supplies the electromotive force needed to polarize the transducer 1. In the preferred embodiment, the mixer 3 converts standard alternating current (120 volts) into direct current (48 volts). It has been proven that to accurately record physiologic sounds, it is important to have a transducer 1 with a high signal to noise ratio and a flat frequency response. These types of sensors may demand high voltages, which are not readily supplied by analogous art that utilizes sound cards built into most commercially available personal computers 9 or batteries.

The voltage is then supplied to the sensor through both XLR inputs 97 equally with respect to ground (phantom power) 93. The audio signal is transmitted through these same inputs approximately 180 degrees out of phase of each other thereby ensuring a balanced signal. Balanced signals are less corrupted by ambient noise relative to unbalanced ones. Inside the stethoscope tube, sound energy generated from organs inside the body is converted into an electrical signal by the microphone. This electrical signal (which is a representation of the sound) is then transmitted to the mixer 3 though the same leads 2 that supply the voltage in the manner described previously. To further prevent this desired signal from being corrupted by external electric/magnetic fields, the cables may be shielded. The mixer 3 may have additional ports to receive electrical signal from additional sensors. In addition, phantom power 93 may be supplied via alkaline (such as the ART Phantom Power Adapter), lithium-ion or other rechargeable 9 volt batteries.

Figure 3A:
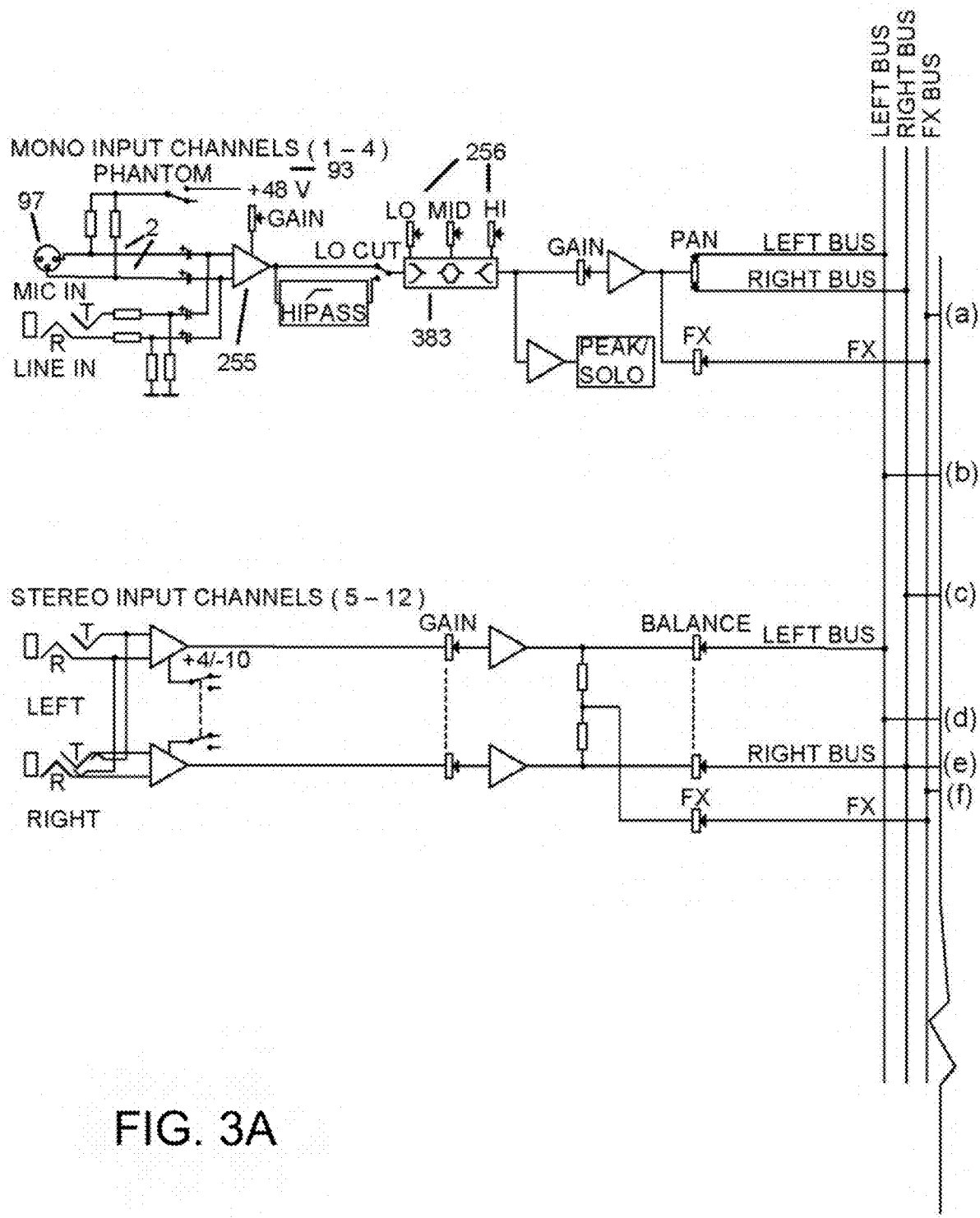
FIG. 3A illustrates a block diagram of an embodiment of the signal conditioning station.
Figure 3A:
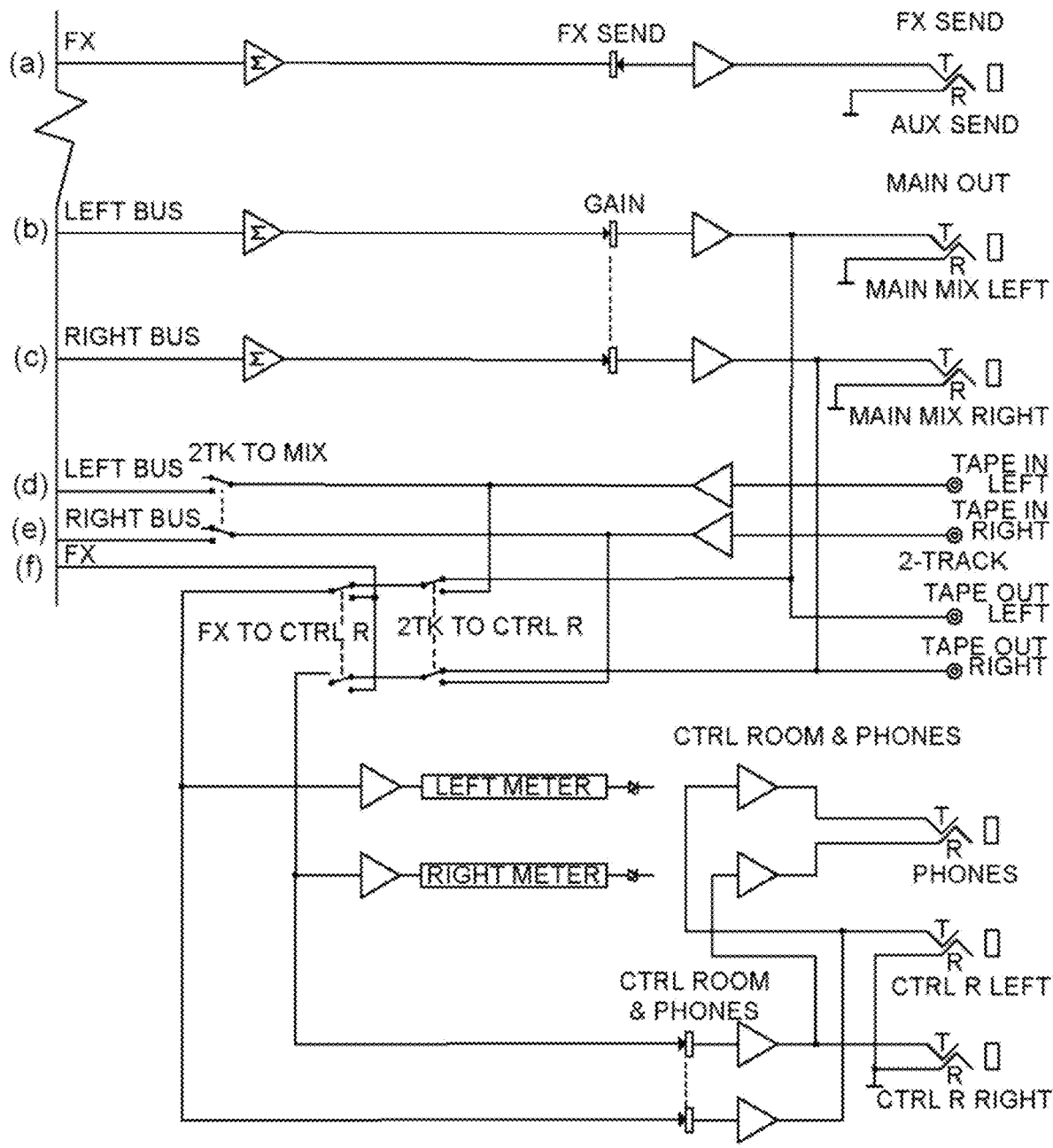
Figure 3B:
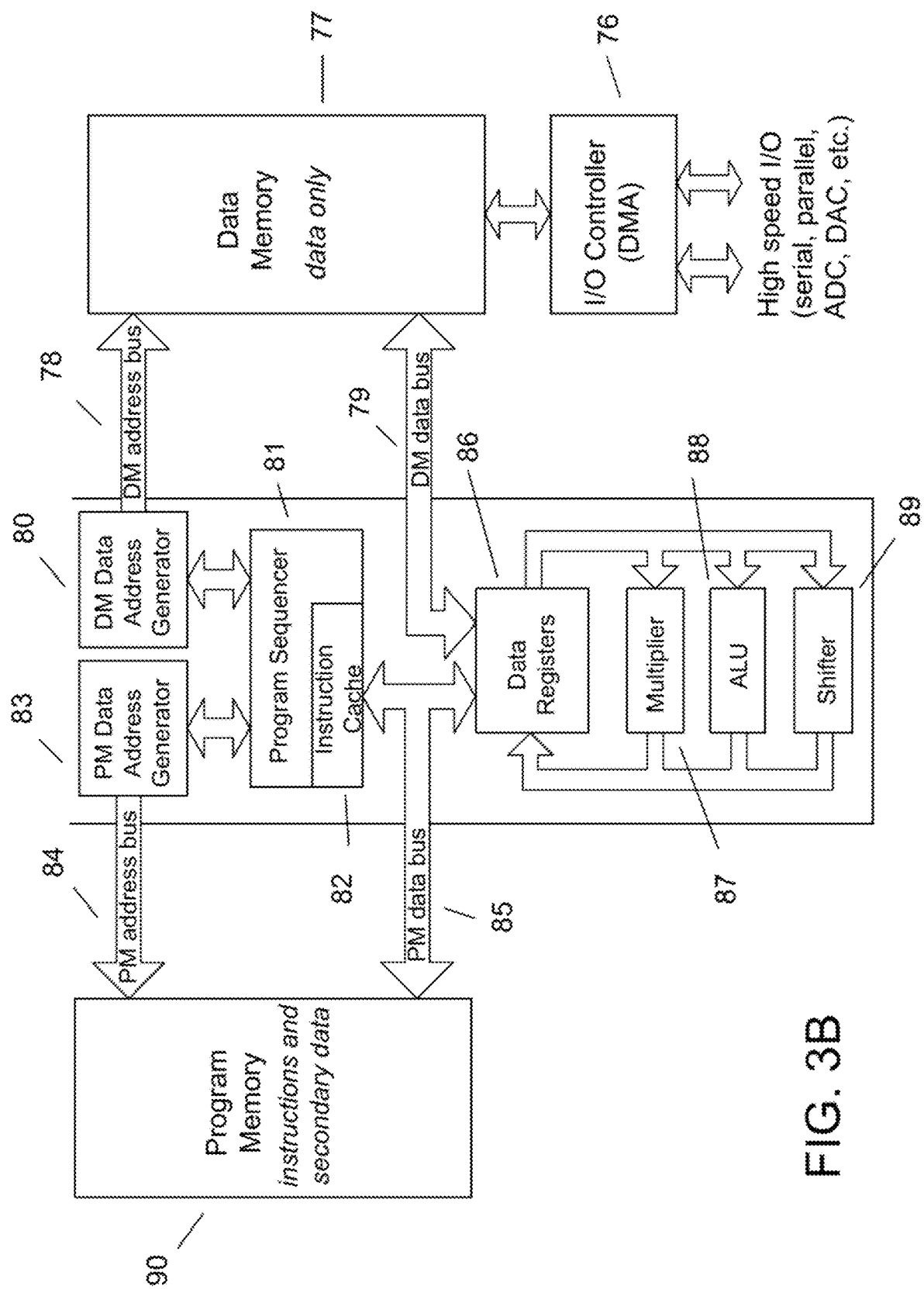
FIG. 3B illustrates a block diagram of the digital signal processor described.

Once the electrical signal is received by the mixer 3, it may be amplified 255 and/or filtered 256. In the preferred embodiment the mixer contains circuitry 383, which can act as a high pass filter (80 Hz) 256 and/or low pass filter (12 kHz) 256, although other frequencies are possible. It should be noted that the invention gives the operator the ability to bypass this processing if they choose. After amplification/filtering, the signal may be sent to a headset 4 where it is converted back to sound energy, thereby enabling the operator to listen to the sound as it is recorded. The signal may also be sent for recording on cassette tapes or it can be sent to a digital signal processor (DSP) 5. One such example is the DEQ 2496, a digital equalizer with Super Harvard Architecture (SHARC) signal processors 76,77,78,79,80,81, 82,83,84,85,86,87,88,89,90 and specialized software, made by Behringer which is depicted in FIGS. 3A and 3B.

The digital processor 5 performs the fast Fourier transformation on the signal and displays both the discrete frequency bands and the power of the signal in each band (power spectrum density) 621, as shown in FIGS. 8 and 10, for example. One of ordinary skill in the art will understand that the waveforms shown in FIGS. 8 and 10 (as well as other waveforms, such as FIG. 12A) are merely exemplary, and that the ordinate or Y-axis demonstrates relative values, such as decibel (dB) shown, as well as other measures of PSD, such as, but not limited to, RMS. From here, the operator can selectively amplify/attenuate components of the signal in any frequency band from 20-20000 Hz (similar to an equalizer) 612-615. Unwanted signal can be excluded by compressing 615 (the processor reduces the intensity of all signal components with a volume that is greater than desired) or expanding 615 (reducing the intensity of all frequency components with an intensity less than that desired by the operator) frequencies detected by the transducer 1. Of note, the device can function as a noise gate and/or limiter if compression/expansion is performed to a maximum degree. All operations undertaken by the digital signal processor 5 to alter the incoming audio signal can be displayed via LCD, and device operations 612-620 and 622-623 may be saved in memory by device operation 620 for instant recall by the operator at some future time. The adjustment of stereo width function 623 may or may not be necessary. It is understood that specific operations 612-619 of the digital signal processor 5 may cause the invention to acquire properties of sound transmission similar to conventional acoustic stethoscopes. This characteristic of the claimed invention is a valuable attribute, since a tremendous body of research has already been conducted in the analysis of physiologic auditory signals using said acoustic stethoscopes. Secondly, it is well known that such conventional stethoscopes are still widely popular in the market place. Specifically, settings contained in the digital signal processor 5 may allow clinicians to measure blood pressure values, grade cardiac murmurs (I-VI) and listen to other physiological sounds in a manner which correlates well with findings obtained from a conventional acoustic stethoscope. The ability to perform compression/expansion is an improvement over other forms of analogous art since it allows the device to record physiologic sounds from the human body without having to constantly be directed to by the operator. However, it should be noted that the device might set up so that it is required to be directed by the operator before making recordings.

Figure 5:
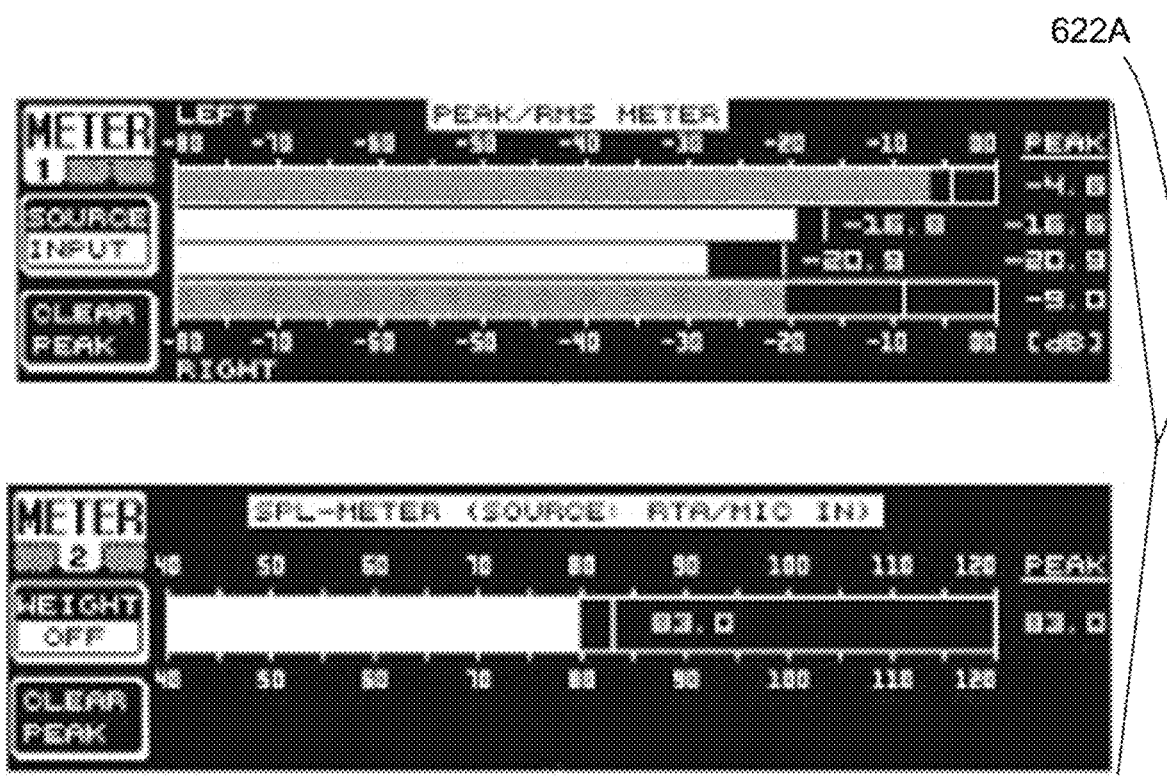
FIG. 5 illustrates a display of the RMS values for the incoming signal (ambient noise) received from the test microphone. These values can be helpful in quantifying the effect of ambient noise on the calculation of the RMS values of the desired signal.

Furthermore, the digital signal processor 5 contains a test transducer 1, which can be deployed by the operator if desired. This test transducer 1 may be affixed to body surface or exposed to the ambient environment. The test transducer 1 records sounds from sources that might corrupt the signal being recorded from the organ of interest. This may include noise present in the ambient environment or sound emitted from other organs in the vicinity of the target organ. The power spectrum density 621 of these ambient signals can be used to calculate and display 622A the corresponding RMS values for the signal as demonstrated in FIG. 5. The components of the undesired signal, which interfere with the signal of interest, are effectively quantified in real time. The DSP 5 may transmit data directly to a computer workstation 9 for further analysis via cable or wireless internet connection 16, 17. This is a significant improvement over analogous art because it can be used to remove ambient noise that contains identical frequency components to those of the target organ, thus producing a much clearer signal from the target organ in addition to enabling the clinician to obtain standardized measurements regardless of the noise level present in the ambient environment at the time of measurement. The processing methods may include (but is not limited to) graphic 612, parametric 613, digital 614 and/or dynamic equalizers 615, as well as signal compression/expansion/boosting/cutting and feedback destruction 622 or bypassed altogether 616.

After this additional processing, the signal from each analogue output is transmitted to an analog-to-digital converter (A/D converter) 6, which may or may not be part of the computer station 9. The A/D converter 6 converts the processed audio information into a digital data stream for transmission to the workstation 9. One advantage of employing a SHARC processor 5 is that digital data may be transmitted to the computer workstation 9 over wireless internet 16,17. This process can be achieved by coupling the SHARC processor 5 to a modem 16 with a WiFi PC card (not shown). Digital data acquired during stethoscope operation may be transferred to a WiFi Access Point/Router 17, and afterward, sent to a modem 16 via CAT5 cable or WiFi USB adapter.

Figure 3C:
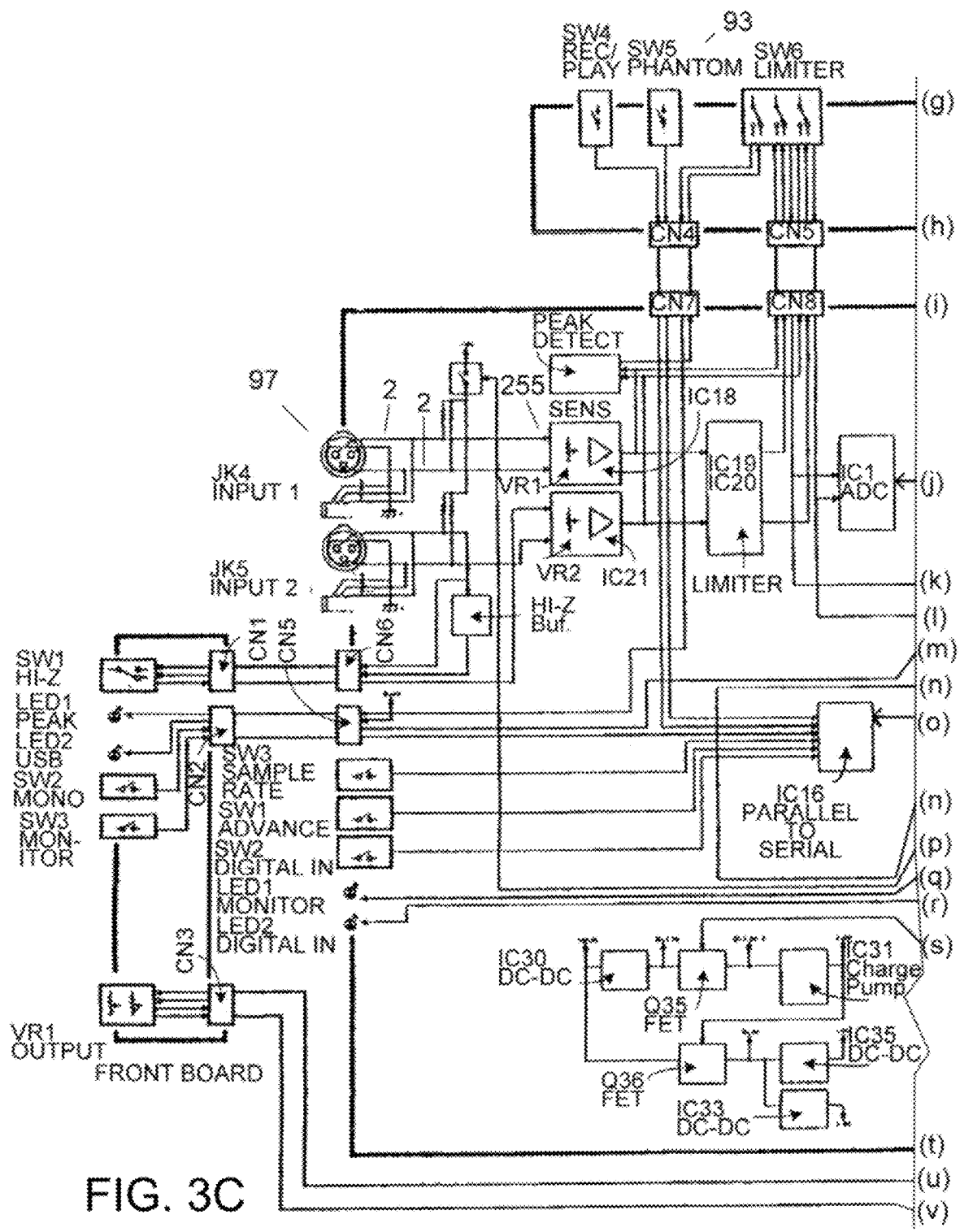
FIG. 3C is a block diagram of elements utilized in data conversion and transfer incorporated within an embodiment.
Figure 3C:
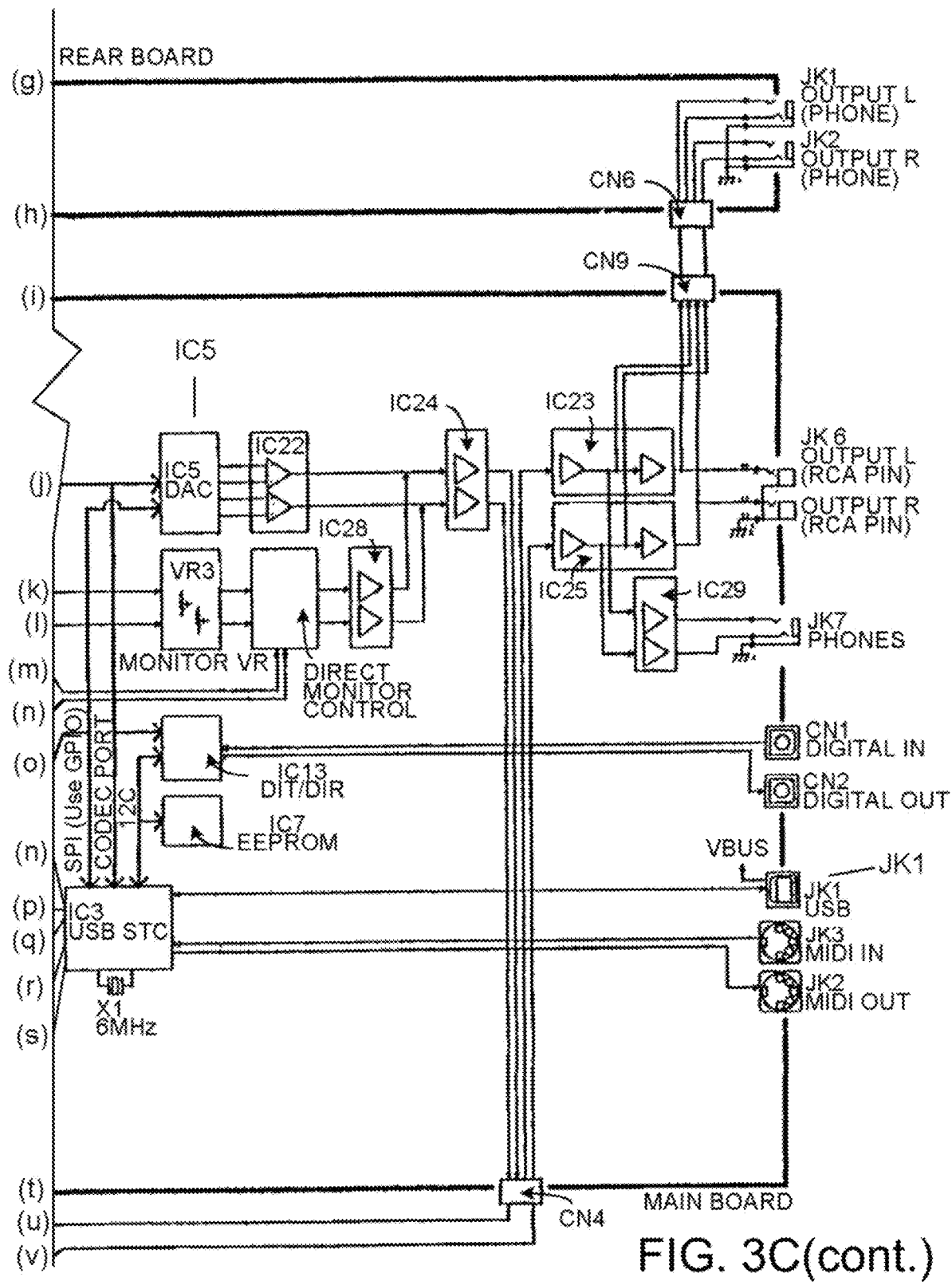
Figure 4A:
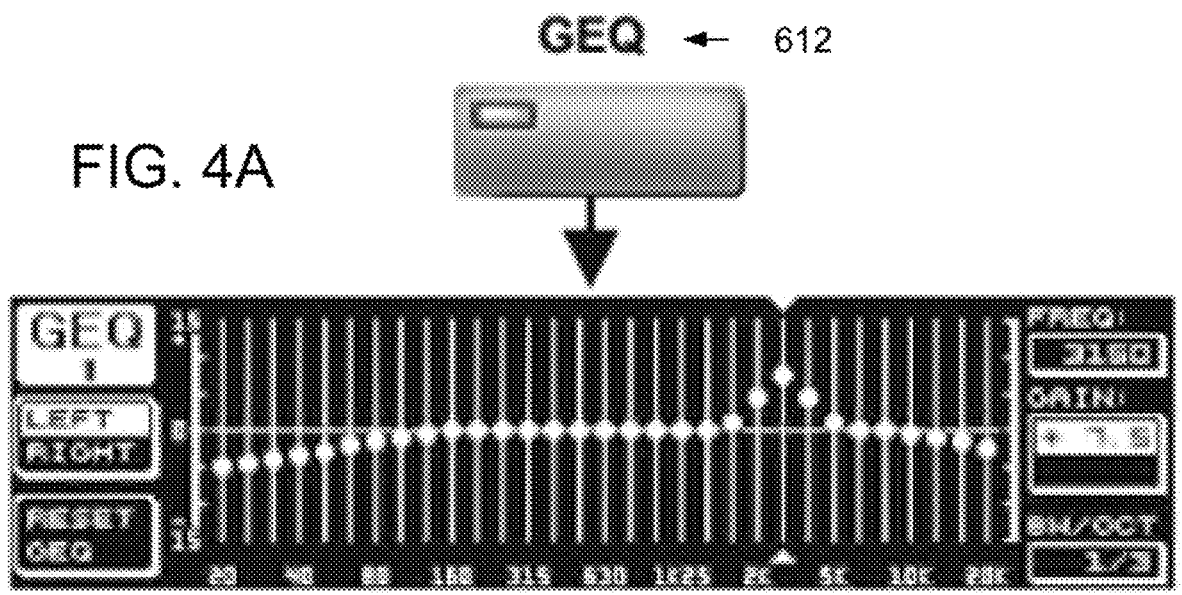
Figure 4B:
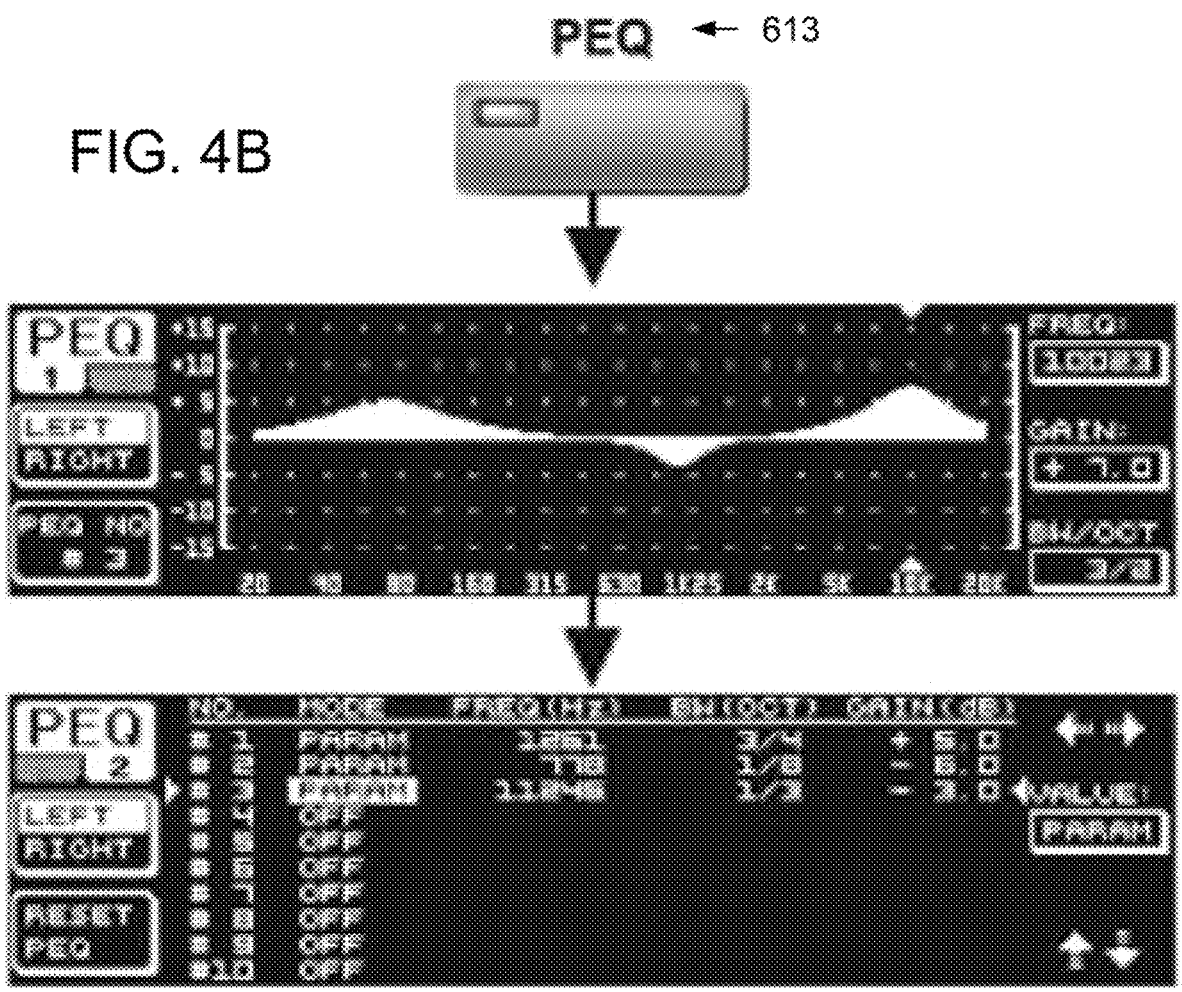
Figure 4C:
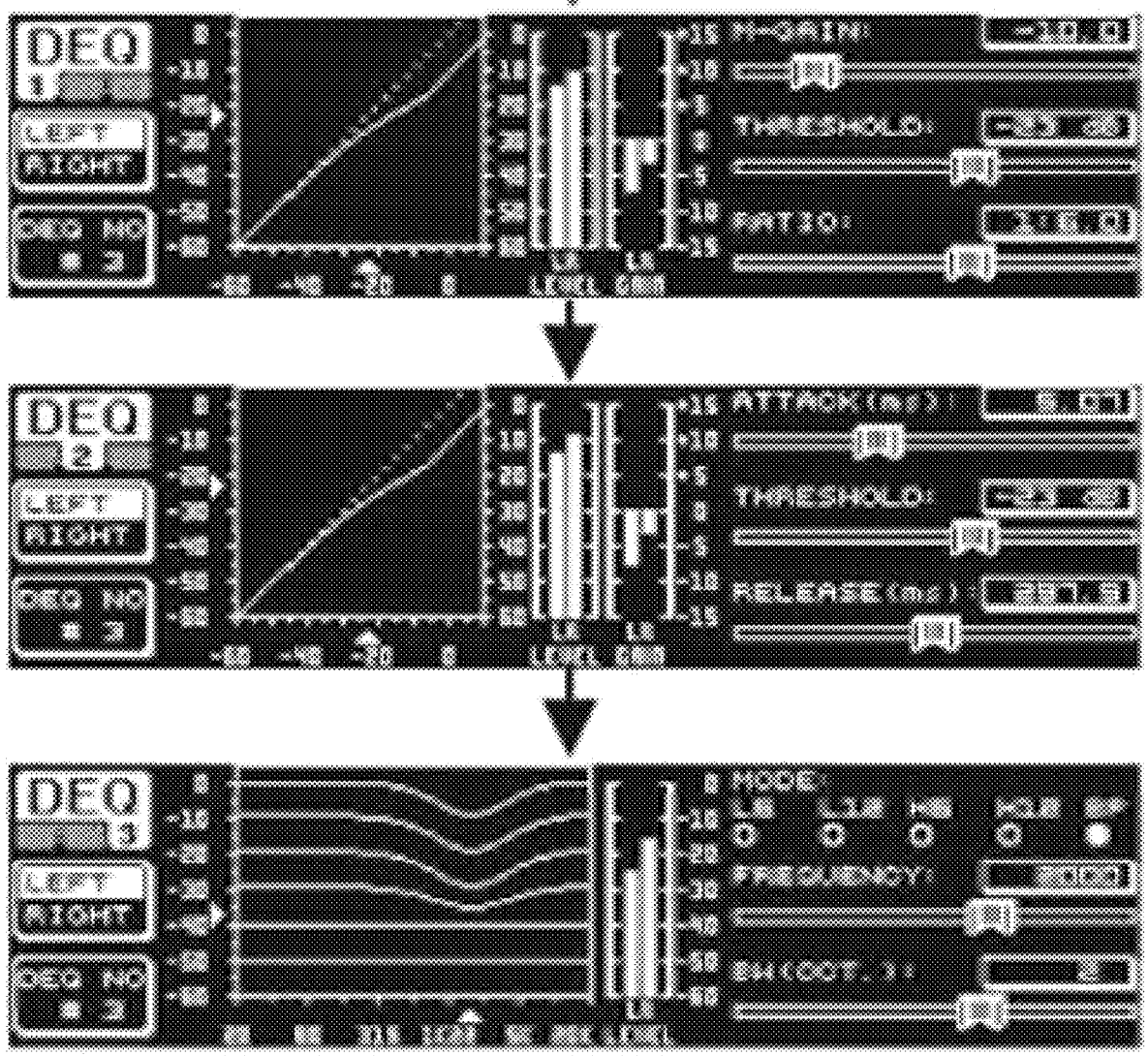
Figure 4E:
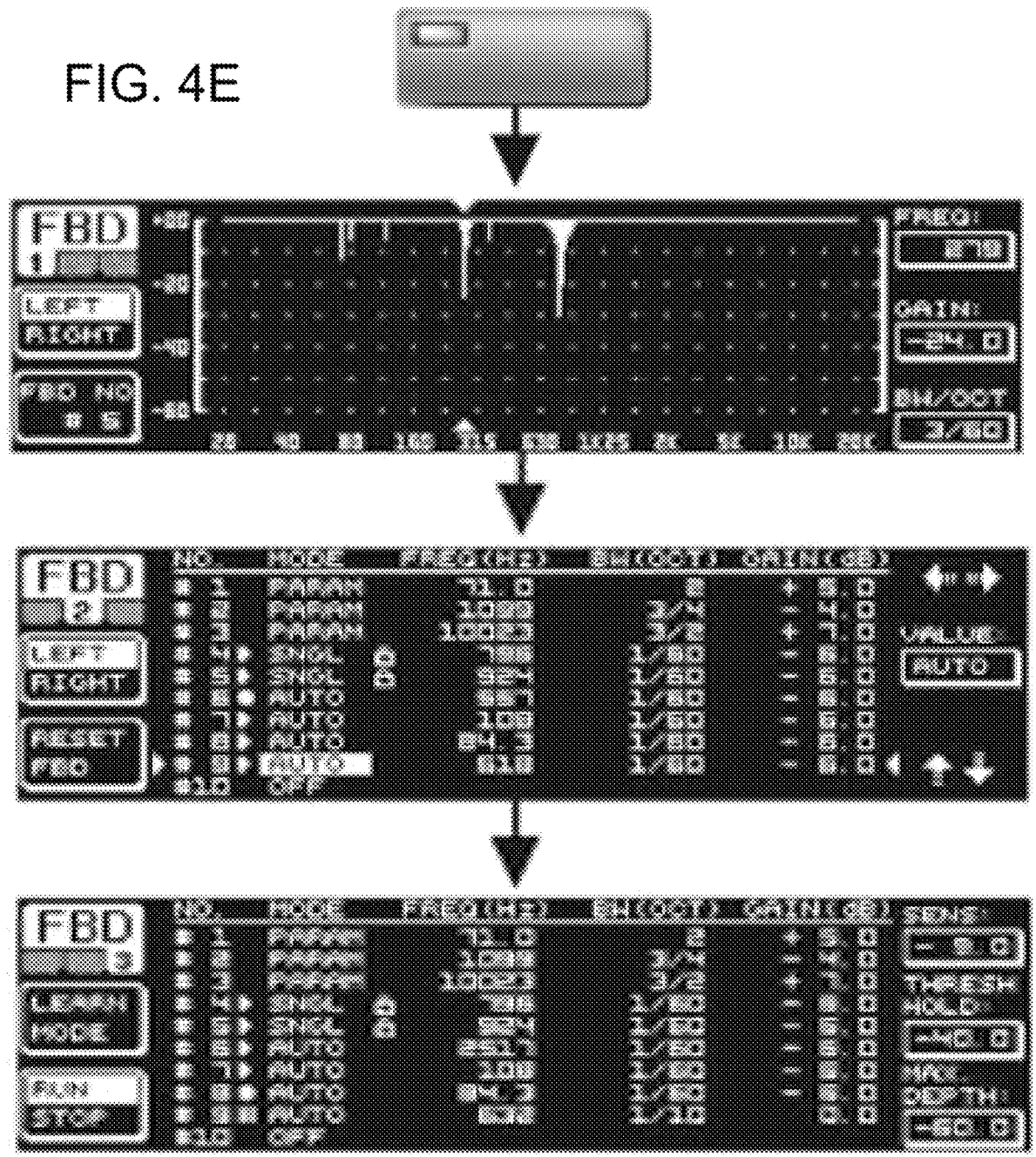
Figure 4F:
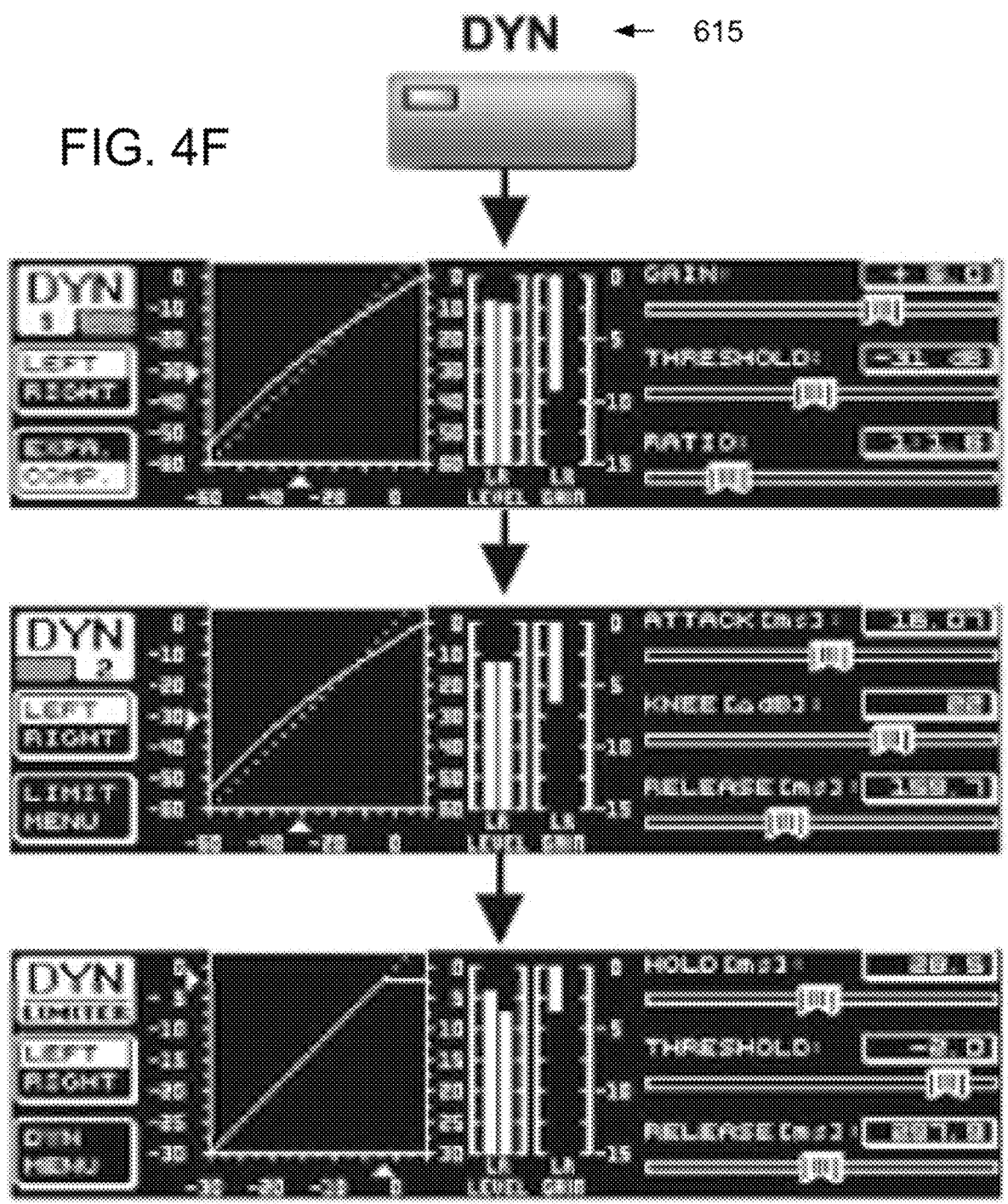
Figure 4H:
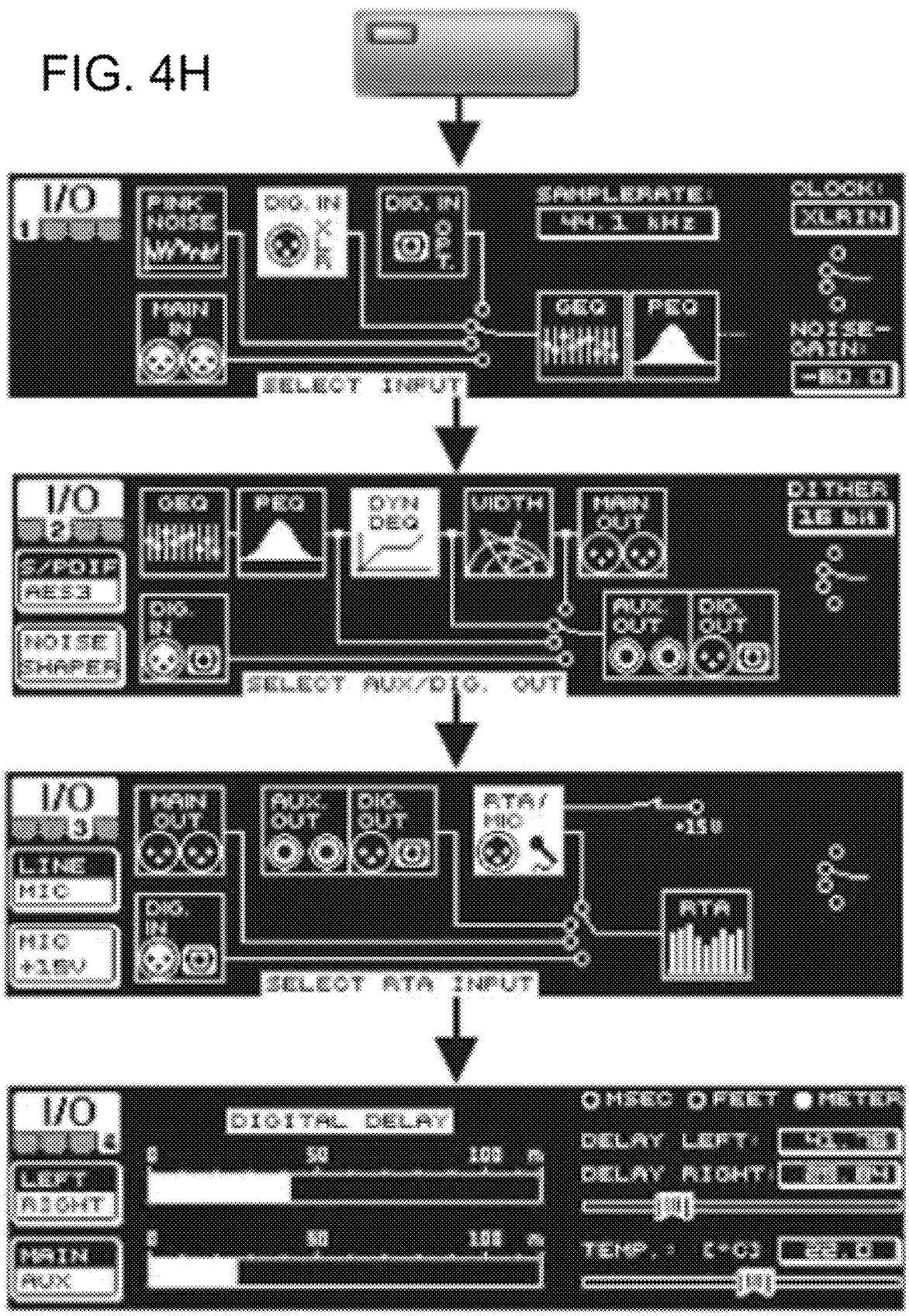
Figure 4I:
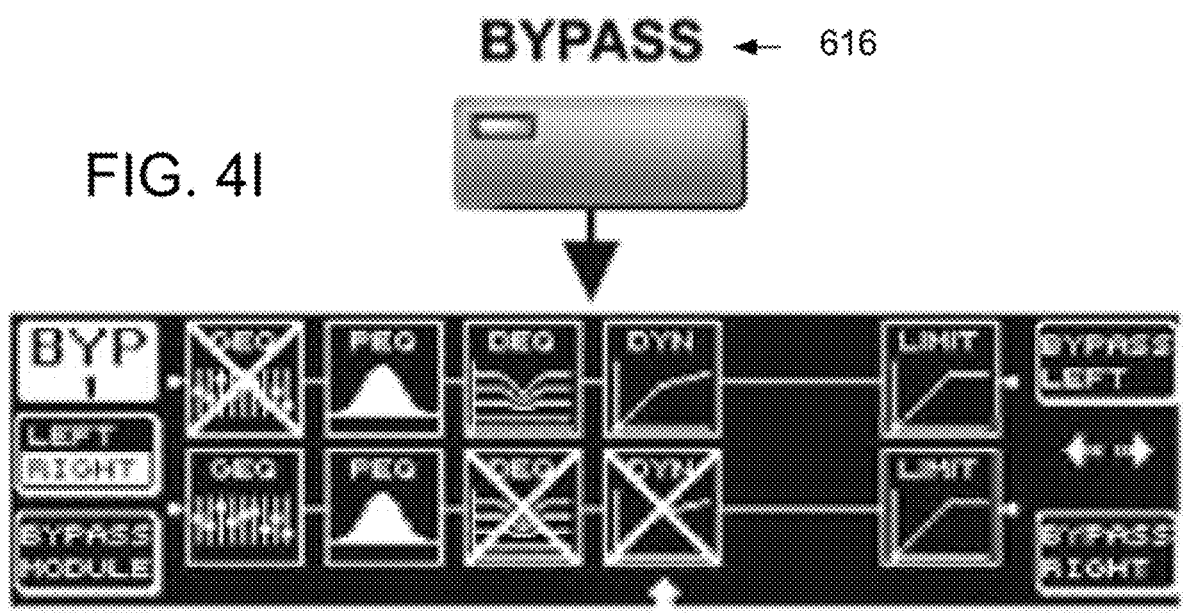
Figure 4J:
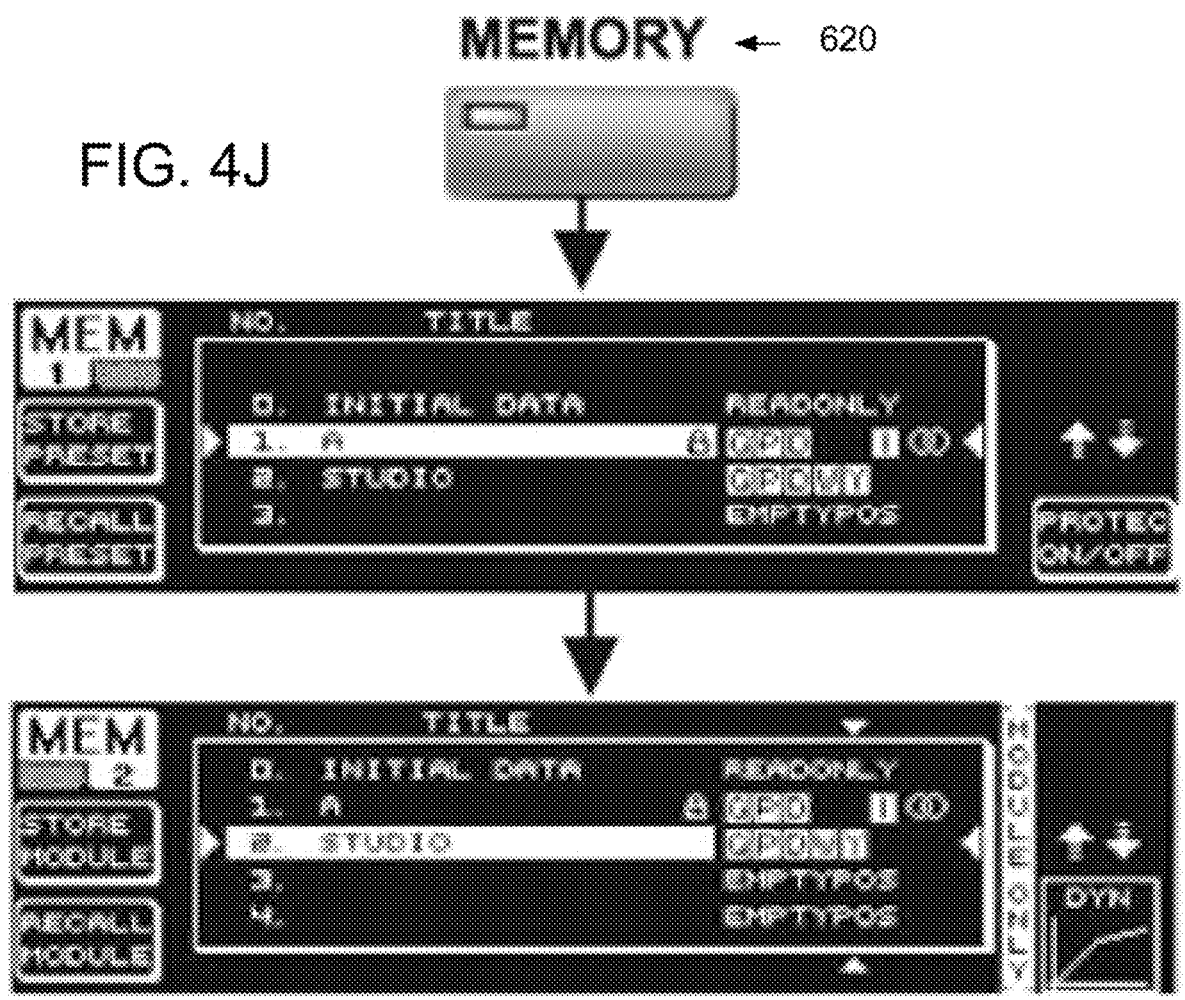
Figure 4K:
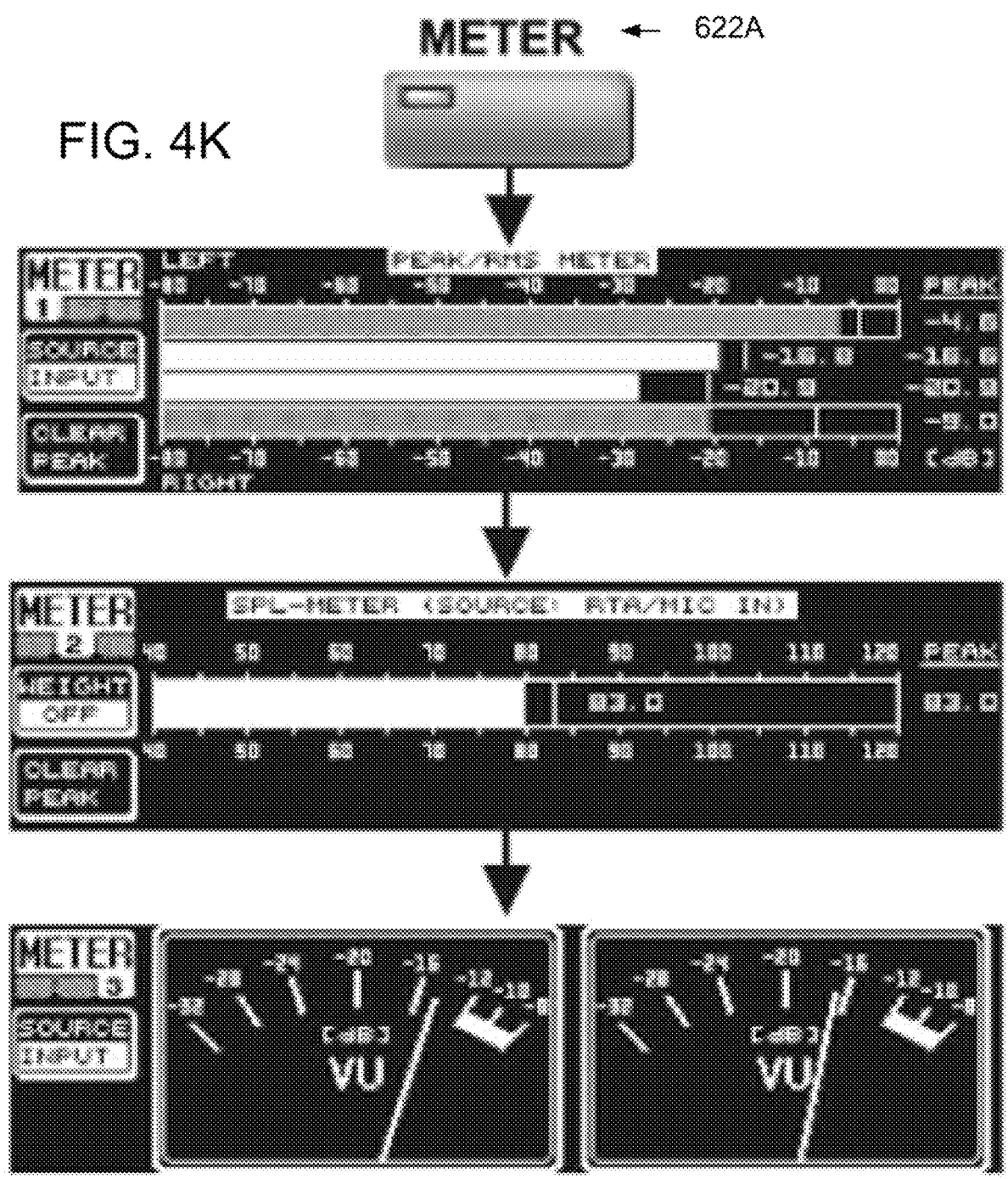
Figure 4L:
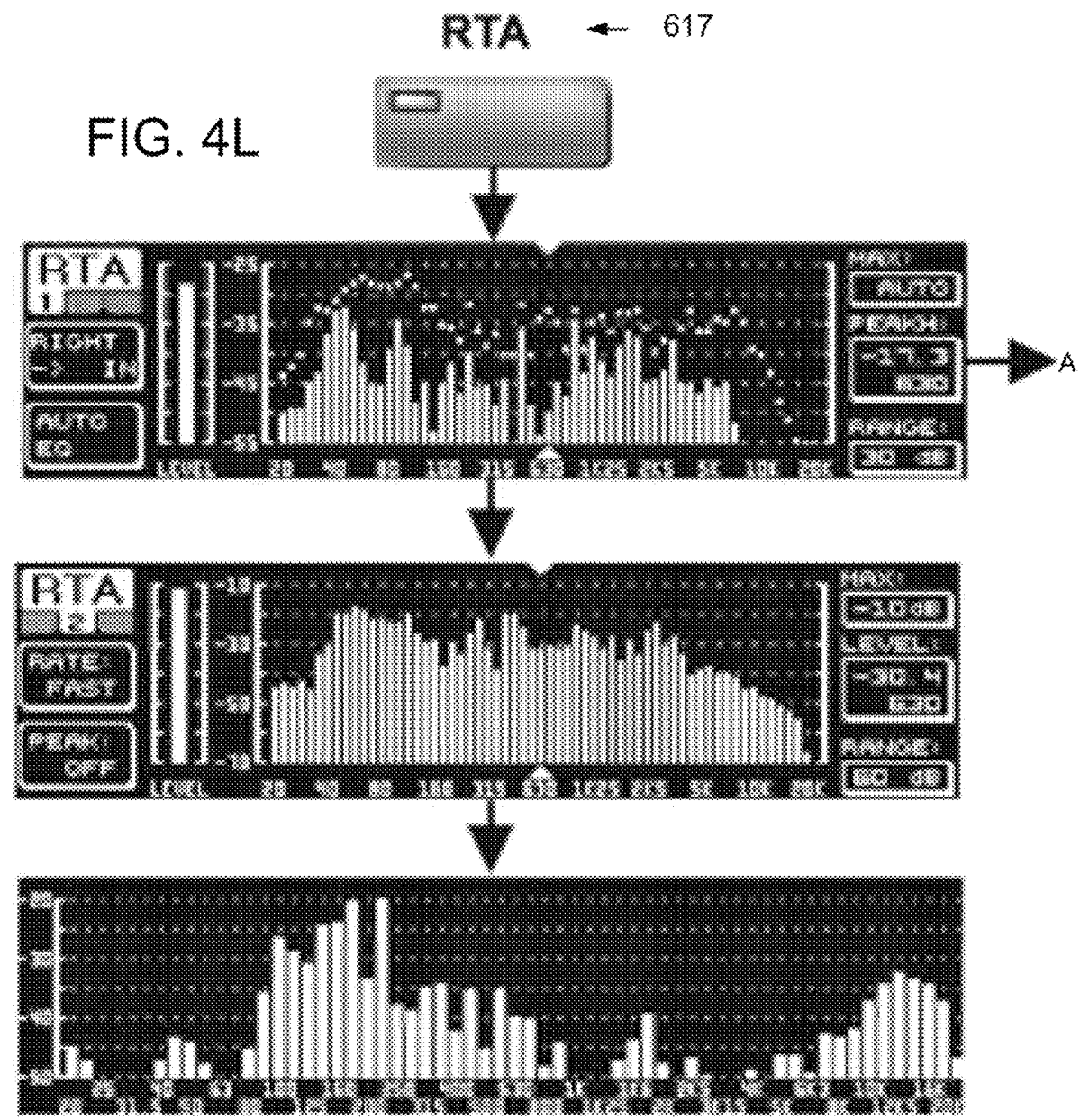
Figure 4L:
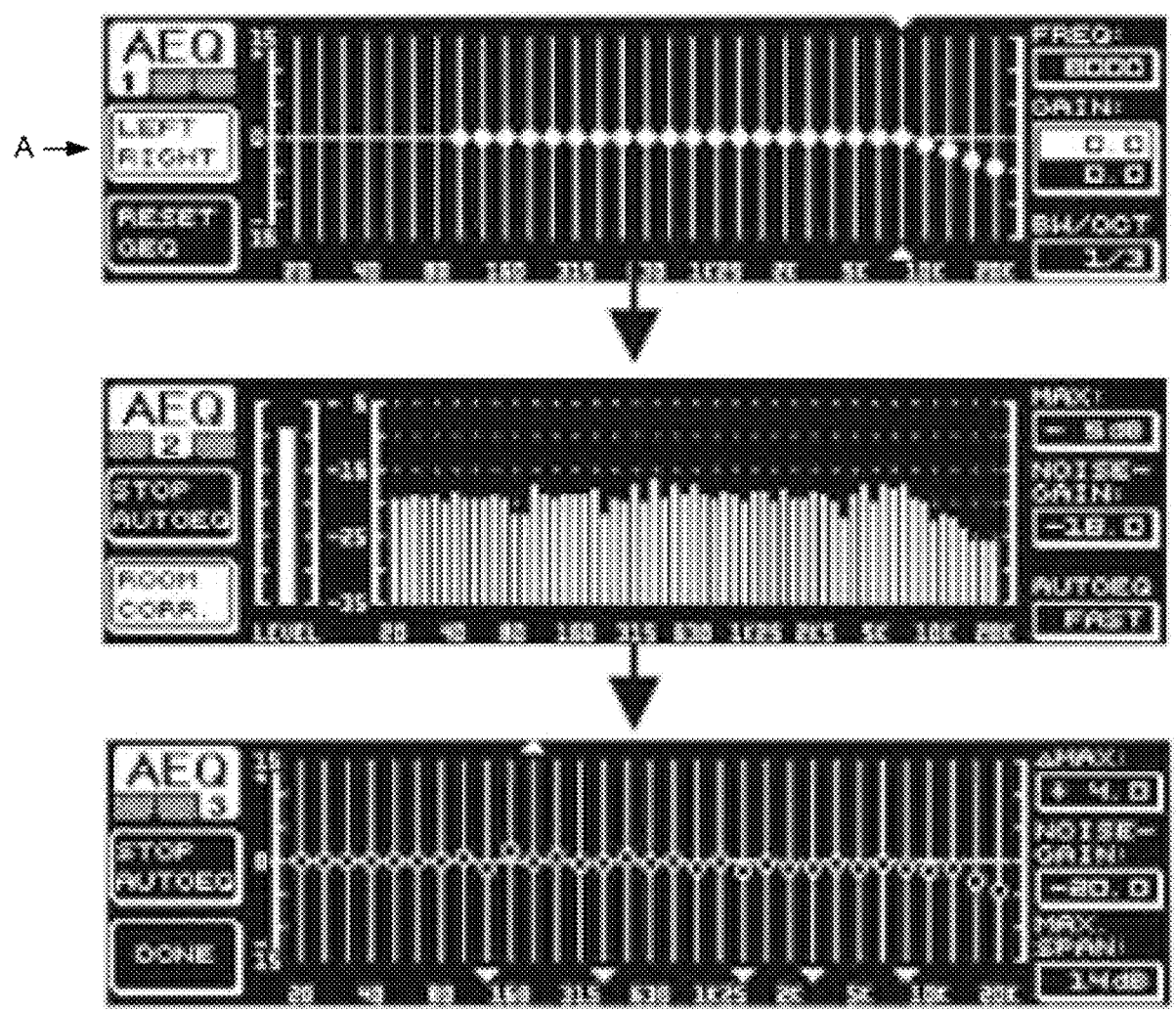
Figure 6:
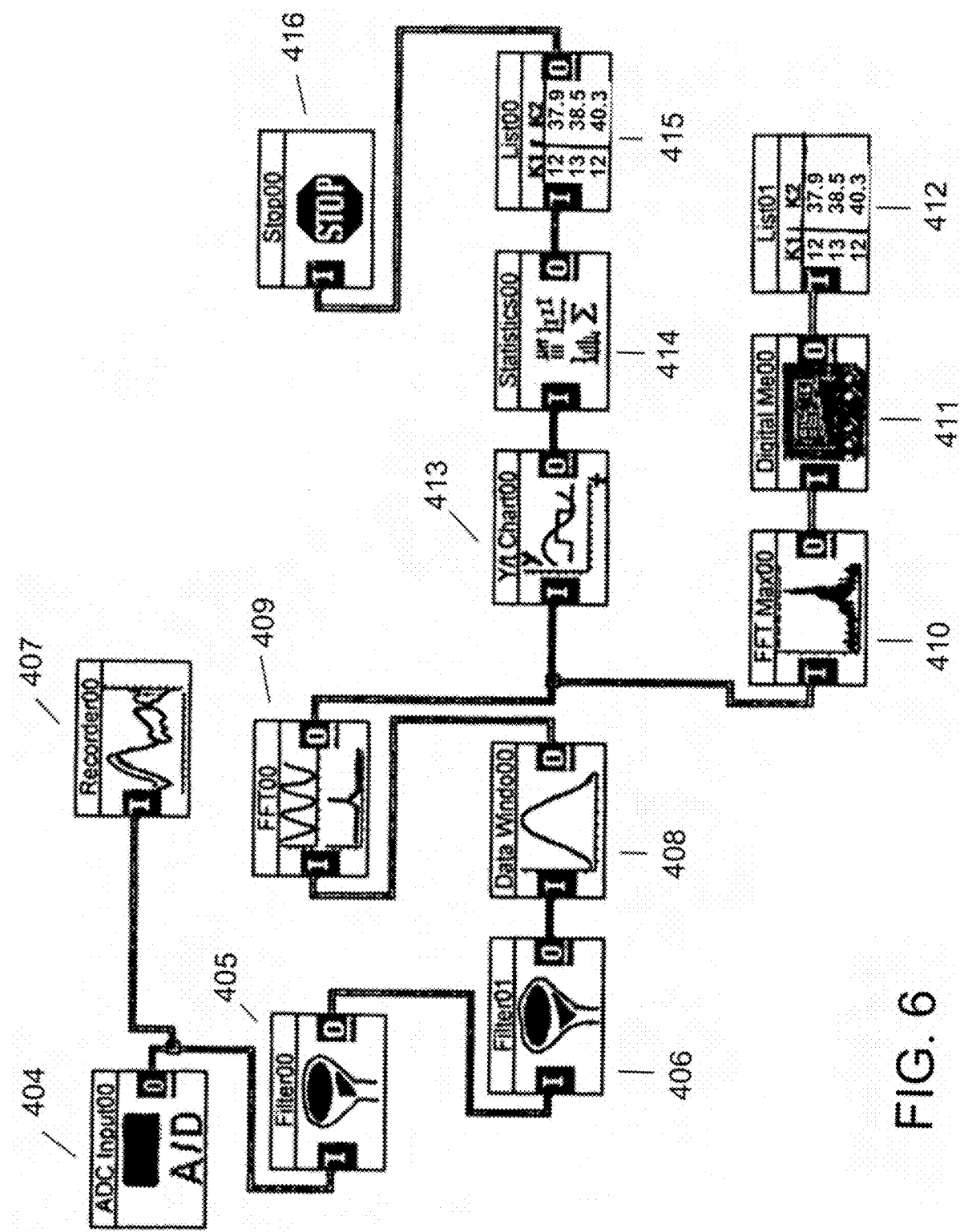
FIG. 6 is a flow chart of the data collection and analysis program. Each icon represents an operation which is performed on incoming data and selecting a corresponding icon can modify these operations.

The sampling rate used in digitizing the data may be adjusted by the operator and should be greater than 44.1 KHz with a bit rate preferably greater than 24 bits per sample. The A/D converter 6 is preferably multi-channel which may contain an additional preamp such as the Edirol UA-25 sold by the Roland Corporation. FIG. 3 is a schematic of all of the hardware components which comprise the preferred embodiment of the invention (components for transmission of data over a wireless network are not shown). FIG. 3A illustrates a first portion of a first schematic connected to a second portion of the first schematic, illustrated in FIG. 3A (cont.), through lines (a)-(f). FIG. 3C illustrates a first portion of a third schematic connected to a second portion of the third schematic, illustrated in FIG. 3C (cont.), through lines (g)-(v). A suitable workstation 9 may be a personal computer of the E-machines series as sold by Lenovo, comprising a microprocessor 12, input/output circuitry 10, and memory for data storage 13, one or more input devices (such as a keyboard 8 or mouse 7), a modular interface with many different graphical displays of incoming data as depicted in FIG. 6, and one or more output devices such as a printer 15, monitor 14 or modem 16 for transmission over the Internet. As shown in FIG. 1, input/output circuitry 10, microprocessor 12, and memory for data storage 13 are interconnected via bus 11. However, it should be understood that other models may be substituted. These computers are controlled and coordinated by operating system 16A, such as Microsoft Windows XP or other system. The operating system 16A may also comprise a window manager 17A, printer manager 18 and additional device managers 21 in addition to one or more device drivers 19,20,22 in order to allow the computer workstation 9 to interface with hardware components.

Figure 2:
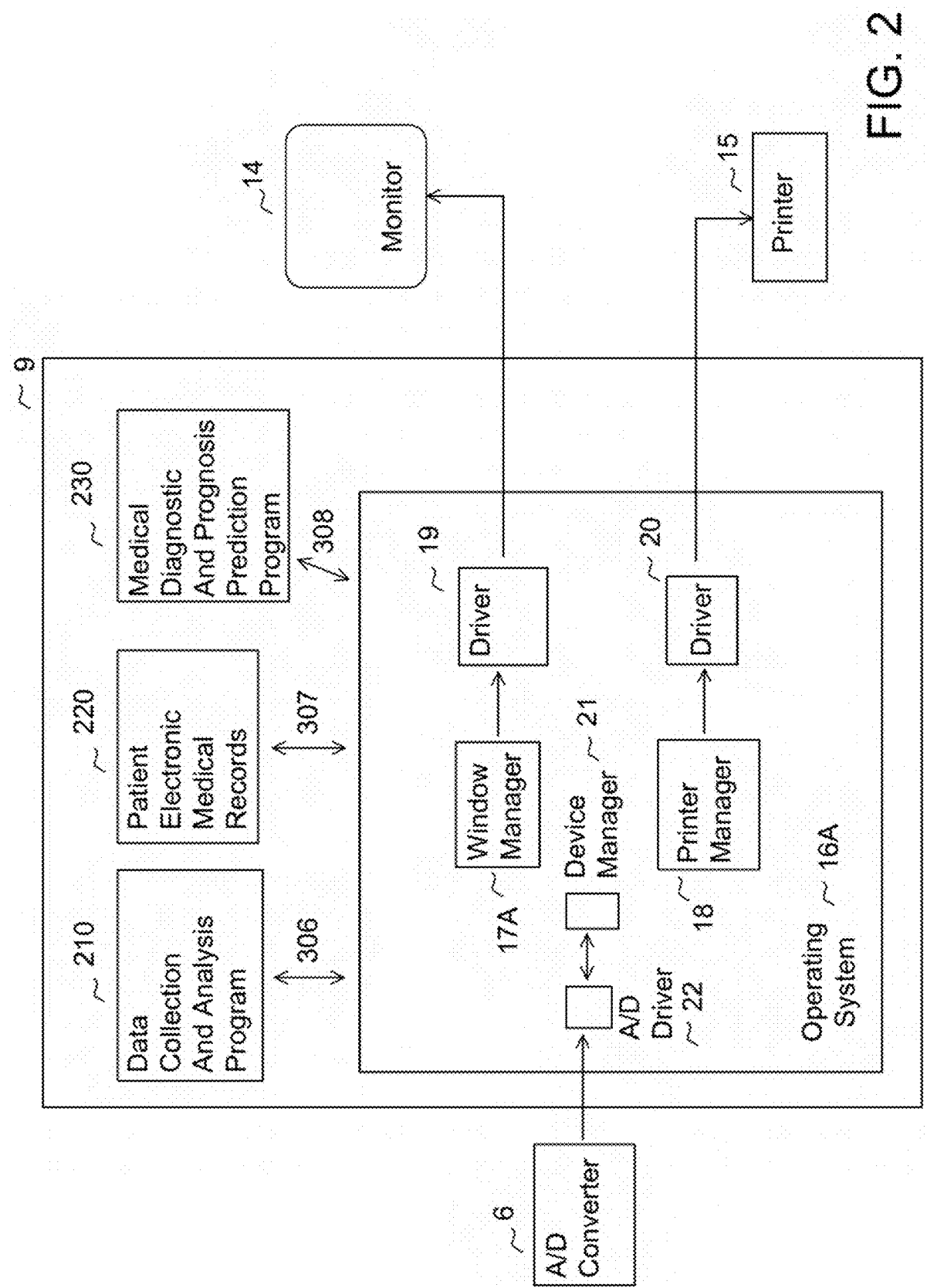
FIG. 2 is an illustration of the computer station component of FIG. 1.

Digital data from the A/D converter 6 is transmitted to input/output (I/O) circuitry 10 of the computer via USB cable JK1. FIG. 2 illustrates the interaction of software elements on the computer workstation 9 with the application programs 210,220,230 and operating system 16A relationships shown by arrows 306,307,308 via system calls. The program (FIG. 6) is organized by a series of graphical icons that are provided via specialized data acquisition software such as DASYLAB 9.0, a product manufactured and sold by Capital Equipment. Each icon, constructed using a graphical programming language, represents a command(s) for the workstation 9 to perform. This program 210 is fully customizable since simply inserting/deleting icons in the flow diagram can make new programs. All commands given to the analysis program by the clinician are accomplished via simple keyboard 8 entries or mouse 7 "clicks". Thus, knowledge of computer programming languages (which many health care personnel do not possess) is not a required prerequisite for proper operation of the instant device.

Prior to first listening to the sound the clinician chooses the sampling rate by clicking on a tab marked "experimental setup." The A/D input icon 404 receives data via I/O circuitry 10. The Recorder Icon 407 displays the time-expanded function of the incoming signal illustrated in FIGS. 7A and 7B in accordance with the description set forth in U.S. Pat. No. 3,990,435. The clinician then clicks the Filter icons 405,406 in order to select frequencies where the signal can be high/low pass filtered digitally. Some examples include digital high/low pass filtering, application of a windowing function to incoming data analogous to PSD calculation, adjustment of sample rate, block size, degree of overlap and recording time. Through the use of these icons, the clinician may also determine the characteristic (Butterworth, Bessel, etc.) and order of the digital filter. The clinician will click the Data Window Icon 408, to select the desired block length, appropriate mathematical window to fit the data with, and determine the degree of overlap (if any) between successive blocks. The FFT icon 409 in the program 210 instructs the computer to calculate the FFT on the portion of the signal represented by each block. The Y/T Icon 413 enables the clinician to view a display of the PSD on a monitor 14 for each block after it is calculated as illustrated in FIGS. 8 and 10. By clicking the FFT max icon 410, the clinician can specify the frequency range within the PSD where both the frequency of maximum intensity and its magnitude may be calculated as illustrated in FIGS. 12A, 12B and 12C. These quantities may be displayed by the icon marked "Digital Meter" 411 or List icon 412. By clicking the Trigger Icon, the clinician can determine which frequency components of the PSD will be excluded from the RMS calculation (not shown).

Since different body organs emit sound in different frequency ranges, the ability to adjust the frequency range is vital if one hopes to construct a single device that can be used to analyze sounds from all of the different organs (not just lung). The Statistics Icon 414 instructs the computer to calculate the RMS value of the signal in the desired frequency range set by the digital high/low pass filters 405,406 or Trigger Icon in the specified range. The List Icon 415 displays the RMS value sequentially as it is calculated from each incoming block as shown in FIGS. 10 and 12. Additional modules may be added to the program 210 for the purpose of determining the magnitude of the change in RMS values with respect to time at a given anatomic position. These RMS values, either as displayed by the List Icon 415 or when combined with additional analysis programs 220, 230 on the workstation 9, give the attending physician a mechanism for comparing the intensity of physiologic sound recorded by the sensor in any desired frequency range and over any duration of time.

In operation, the sensors 1 are affixed to any part of the body surface according to the discretion of the clinician. The system is then initialized and data is transmitted to application program 210, as the patient inhales/exhales, sound is converted to audio signals which may be amplified/filtered/processed before being relayed to both the clinician and the application program 210 in the computer workstation 9. At any instant in time (if the physician hears an interesting sound) the physician can start the digital recording by clicking the Recorder Icon 407, a green arrow in the upper left hand corner of the screen. After the signal of interest is no longer audible, the physician may stop recording by clicking the red square icon or specifying the duration of recording via the "Stop" icon 416. The computer recording may be influenced by the DSP 5 via compression/limiting 615 or equalization 612,613,614 as described above. After recording is complete, the clinician may click the list icon 415 to obtain a columnar display of the desired RMS values. Review of this list may give the clinician valuable information regarding the degree of functionality/pathology present in certain organs (lung, heart, bowel, etc.). The settings and/or outputs of the PSD (calculated from the Y/T icon 413), Time Expanded Waveform 407, FFT Maximum 410, Filters 405,406 and List 412,415 can all be saved in memory 13, printed on paper via printer 15 or transmitted via modem 16 to another computer 9 though the internet. It should be understood that additional icons may be added to the program in FIG. 6 if additional data manipulation is desired. In addition, program settings for analysis of auditory signals from two or more different sources (organs, ambient noise, etc.) such as the heart and trachea (FIGS. 9 and 11) may be combined, thereby enabling the operator to analyze discrete frequency bands within a signal. For instance, if an observed physiologic sound is composed of sounds from the trachea and heart superimposed on each other, the operator may combine modules from FIGS. 9 and 11 into a single program that will separately analyze the signals from each source simultaneously. If there exists overlap, additional methods may be deployed to separate out the overlapping frequency components of the two or more sources.

Lastly, data generated from this analysis program 210 may be integrated with numerical/text data contained in a patient's electronic medical records 220. The integration of data among these programs 210,220,230 can be directed by an operator using a mouse 7, keyboard 8 or other input. U.S. Pat. Nos. 6,944,821 and 6,154,756 demonstrate two such methods for performing said integration of data contained on multiple program elements. Additional software programs 230 may combine data from the analysis program 210 and electronic medical records 220 for the purposes of assessing target organ functionality, characterization of pathology if present, and generating accurate predictions regarding the degree of functionality of the target organ system in the near future.

It is to be understood that even though numerous characteristics and advantages of various embodiments of the present invention have been set forth in the foregoing description, together with details of the structure and function of various embodiments of the invention, this detailed description is illustrative only, and changes may be made in detail, especially in matters of structure and arrangements of parts within the principles of the present invention to the full extent indicated by the broad general meaning of the terms in which the appended claims are expressed.

What is claimed is:

1. A system for acquiring and processing physiological sounds comprising:
   an apparatus comprising:
   a single sensor configured to convert an analogue signal into an electrical output representative of said physiological sounds;
   an analogue to digital converter operatively coupled to said sensor, wherein said analogue to digital converter is configured to convert said electrical output into a stream of digital data;
   a serial to parallel converter operatively coupled to said analogue to digital converter, said serial to parallel converter configured to convert at least a portion of said stream of digital data into a parallel output; and
   a display device configured to display a plurality of icons, wherein said plurality of icons displayed on said display device is configured for customization by a user through insertion of an additional icon in said plurality of icons displayed, and wherein the apparatus is configured to initiate a recording of said physiological sounds by interaction of said user with at least one icon in said plurality of icons displayed.

2. The system of claim 1, said apparatus further comprising:
   a digital to analogue converter operatively coupled to said serial to parallel converter, said digital to analogue converter configured to convert at least a portion of said parallel output into a second analogue signal for transmission over a wireless network.

3. The system of claim 1, said apparatus further comprising: a processing unit operatively coupled to said analogue to digital converter, said processing unit configured to compute a mathematical transform on at least a portion of said parallel output.

4. The system of claim 3, wherein said mathematical transform is a fast Fourier transformation.

5. The system of claim 1, further comprising:
   said display device configured to display information comprising a vital sign.

6. The system of claim 1, wherein said physiological sounds are sounds generated by an organ in a frequency range up to 20,000 Hz, and wherein said sensor is one sensor of a plurality of sensors and at least two sensors of said plurality of sensors are configured to convert said physiological sounds into a plurality of corresponding electrical signals.

7. The system of claim 6, wherein said plurality of sensors comprises at least three sensors.

8. The system of claim 1, wherein said apparatus is characterized as a first apparatus, and further comprising a second apparatus operatively coupled to said first apparatus, said second apparatus comprising:
   an electronic memory configured to store a signal representative of at least a portion of said parallel output; and
   a second processing unit coupled to said electronic memory, said second processing unit configured to retrieve from said electronic memory and process said signal representative of at least a portion of said parallel output into a processed signal.

9. The system of claim 1, wherein the physiological sounds are ambient noise generated by an organ in a frequency range up to 20,000 Hz.

10. The system of claim 6, wherein at least one sensor of said plurality of sensors is configured to be positioned on a body surface.

11. The system of claim 7, wherein at least one sensor of said at least three sensors is configured to be positioned on a body surface and wherein said physiological sounds are sounds generated by an organ in a frequency range up to 20,000 Hz.

12. The system of claim 11, wherein said physiological sounds comprise ambient noise.

13. The system of claim 5, wherein said vital sign is a heart rate.

14. The system of claim 10, further comprising an electronic memory for storing a signal representative of at least a portion of the plurality of electrical outputs generated by the plurality of sensors.

15. An apparatus comprising:
   a port configured to be operatively coupled to a single sensor, wherein said single sensor is configured to convert physiological sounds into an electrical signal;
   a corresponding analogue to digital converter operatively coupled to the sensor, wherein said analogue to digital converter is configured to convert at least a portion of said electrical signal into a stream of digital data;
   a serial to parallel converter configured to convert at least a portion of the stream of digital data into a parallel output;
   a memory configured to store at least a portion of the stream of digital data; and
   a display device configured to display a plurality of icons, wherein each icon of said plurality of icons displayed respectively correspond to at least one operation of a plurality of operations that said apparatus is configured to perform, wherein the plurality of icons displayed on said display device is configured for customization by a user through insertion of an additional icon in said plurality of icons displayed, and wherein the apparatus is configured to initiate a recording of said physiological sounds by interaction of said user with at least one icon in said plurality of icons displayed.

16. The apparatus of claim 15, further comprising a parallel to serial converter operatively coupled to the serial to parallel converter and configured to convert at least a portion of said parallel output into a transmission serial output, wherein said apparatus is configured to send said transmission serial output across a network.

17. The apparatus of claim 16, wherein the network is a wireless network, the apparatus further comprising a digital to analogue converter configured to convert at least a portion of said transmission serial output into an analogue signal for transmission over said wireless network.

18. The apparatus of claim 15, wherein said physiological sounds are sounds generated by an organ and comprise ambient noise, the apparatus further comprising a filter which is configured to filter ambient noise from said at least one stream of digital data prior to conversion of serial output into said parallel output.

19. The apparatus of claim 15, wherein an entirety of the stream of digital data is stored in said memory.

20. The apparatus of claim 15, wherein said memory is configured to store an electronic medical record and said display device is configured to display at least a portion of said electronic medical record.

* * * * *

UNITED STATES PATENT AND TRADEMARK OFFICE
CERTIFICATE OF CORRECTION

| | | |
|---|---|---|
| PATENT NO. | : 11,357,471 B2 | Page 1 of 1 |
| APPLICATION NO. | : 14/524810 | |
| DATED | : June 14, 2022 | |
| INVENTOR(S) | : Michael E. Sabatino | |

It is certified that error appears in the above-identified patent and that said Letters Patent is hereby corrected as shown below:

On the Title Page

In page 2, Column 1, Item (56), U.S. Patent Documents, cite No. 67, delete "Holcman" and insert --Propach et al.--, therefor.

In page 9, Column 1, Item (56), U.S. Patent Documents, cite No. 44, delete "Becking et al." and insert --Bocking et al.--, therefor.

In page 9, Column 1, Item (56), U.S. Patent Documents, cite No. 48, delete "Ai-Aii" and insert --Al-Ali--, therefor.

In page 10, Column 2, Item (56), U.S. Patent Documents, cite No. 75, delete "Ai-Aii" and insert --Al-Ali--, therefor.

In page 14, Column 2, Item (56), Other Publications, cite No. 21, delete "IPod" and insert --iPod--, therefor.

In page 14, Column 2, Item (56), Other Publications, cite No. 22, delete "IPod" and insert --iPod--, therefor.

In page 15, Column 1, Item (56), Other Publications, cite No. 24, delete "Mousdavi Z." and insert --Moussavi Z.--, therefor.

In page 16, Column 2, Item (56), Other Publications, cite No. 35, delete "Chen, D., etaL" and insert --Chen, D., et al.--, therefor.

Signed and Sealed this
Sixteenth Day of August, 2022

Katherine Kelly Vidal
*Director of the United States Patent and Trademark Office*